(12) United States Patent
Sakuraba et al.

(10) Patent No.: US 7,566,781 B2
(45) Date of Patent: Jul. 28, 2009

(54) IMIDAZOPYRIDINE COMPOUND

(75) Inventors: Shunji Sakuraba, Tsukuba (JP);
Minoru Moriya, Tsukuba (JP);
Hidekazu Takahashi, Tsukuba (JP);
Hiroyuki Kishino, Tsukubamirai (JP);
Makoto Jitsuoka, Moriya (JP); Minoru Kameda, Adachi (JP); Akio Kanatani, Ushiku (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 161 days.

(21) Appl. No.: 11/579,570

(22) PCT Filed: May 9, 2005

(86) PCT No.: PCT/JP2005/008819

§ 371 (c)(1),
(2), (4) Date: Nov. 6, 2006

(87) PCT Pub. No.: WO2005/108399

PCT Pub. Date: Nov. 17, 2005

(65) Prior Publication Data

US 2007/0249659 A1    Oct. 25, 2007

(30) Foreign Application Priority Data

May 10, 2004    (JP) .................. 2004-139909

(51) Int. Cl.
*C07D 491/02*  (2006.01)
*C07D 237/02*  (2006.01)
*C07F 9/02*    (2006.01)
*A61K 31/519*  (2006.01)

(52) U.S. Cl. .................. 544/281; 544/229; 544/244; 514/258; 514/259; 514/300; 514/43; 514/80; 546/121

(58) Field of Classification Search .................. 424/490, 424/452, 457, 458, 465, 474, 489, 494, 495, 424/497, 498; 514/152
See application file for complete search history.

(56) References Cited

U.S. PATENT DOCUMENTS

| 6,930,185 | B2 | 8/2005 | Ishihara et al. |
| 7,115,750 | B1 | 10/2006 | Kato et al. |
| 2005/0222161 | A1 | 10/2005 | Moriya et al. |
| 2005/0261303 | A1 | 11/2005 | Taniguchi et al. |
| 2006/0287340 | A1 | 12/2006 | Moriya et al. |
| 2007/0208046 | A1 | 9/2007 | Otake et al. |

FOREIGN PATENT DOCUMENTS

| JP | 2001-226269 | | 8/2001 |
| JP | 2001226269 A | | 8/2001 |
| JP | 2003-313126 | | 11/2003 |
| JP | 2003313126 A | | 11/2003 |
| WO | WO 01/21577 | | 3/2001 |
| WO | WO2002042273 | * | 3/2002 |
| WO | WO 02/42273 | | 5/2002 |
| WO | WO 2004/011440 | | 2/2004 |
| WO | WO 2004/031177 | | 4/2004 |
| WO | WO 2004/103992 | | 12/2004 |
| WO | WO 2005/035526 | | 4/2005 |
| WO | WO 2005/085200 | | 9/2005 |
| WO | WO2004031177 A1 | | 2/2006 |
| WO | WO 2006/044293 | | 4/2006 |

OTHER PUBLICATIONS

Patani et al, A Rational Approach in Drug Design, Chemical Reviews, vol. 96, pp. 3147-3176, 1996.*
Shimada et al., Nature, vol. 396 (1998), pp. 670-674, "Mice lacking melanin-concentrating hormone are hypophagic and lean".
Dyke et al., Exp. Opin. Ther. Patents, vol. 15 (2005), pp. 1303-1313, "Recent developments in the discovery of MCH-1R antagonists for the treatment of obesity—an update".

* cited by examiner

*Primary Examiner*—Ardin Marschel
*Assistant Examiner*—Savitha Rao
(74) *Attorney, Agent, or Firm*—Janet E. Fair; Catherine D. Fitch

(57) ABSTRACT

The present invention provides an imidazopyridine compound represented by formula (I),

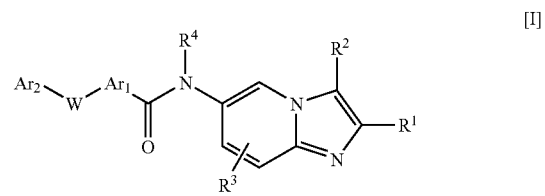

wherein $R^1$ and $R^2$ each independently represent a $C_{1-6}$ alkyl group et al; $R^3$ and $R^4$ each independently represent a hydrogen atom, a methyl et al; $Ar_1$ is a divalent substituent representing a monocyclic or bicyclic, 3- to 8-membered aromatic or aliphatic heterocyclic group et al; $Ar_2$ represents an aromatic carbocyclic group, or an aromatic heterocyclic group; W represents —$(CH_2)_m$ et al, and m indicates an integer of from 0 to 10. This compound acts as a melanin concentrating hormone receptor antagonist, and is useful as treating agents for obesity.

18 Claims, No Drawings

IMIDAZOPYRIDINE COMPOUND

CROSS-REFERENCE TO RELATED APPLICATIONS

This application is a U.S. National Phase application under 35 U.S.C. §371 of PCT Application No. PCT/JP2005/008819, filed May 9, 2005, which claims priority under 35 U.S.C. §365(b) from Japanese patent application No. JP2004-139909, filed May 10, 2004.

TECHNICAL FIELD

The present invention relates to imidazopyridine compounds useful in the field of medicines. The compounds act as a melanin concentrating hormone receptor antagonist, and are useful as preventing or treating agents for various circular system diseases, nervous system diseases, metabolic diseases, genital diseases, respiratory diseases, digestive diseases, etc.

BACKGROUND ART

Melanin concentrating hormone (hereafter abbreviated as "MCH") is a cyclic peptide hormone/neuro-peptide, which was for the first time isolated by Kawauchi, et al., in 1983 from sermon hypophysis [Nature, Vol. 305, 321 (1983)]. The hormone is known to functionally antagonize to melanin cell stimulating hormone in fishes, to cause concentration of melanin granules in melanophore and participate in body color change [International Review of Cytology, Vol. 126, 1 (1991); Trends in Endocrinology and Metabolism, Vol. 5, 120 (1994)]. Also in mammals, MCH-containing neuron nerve cells are localized in the hypothalamus lateral field and uncertain zone, but their nerve fibers are projecting over a very wide scope in the brain [The Journal of Comparative Neurology, Vol. 319, 218 (1992)], and MCH is considered to preside over various central functions in living bodies.

Hypothalamus lateral field is known of old as feeding center, and furthermore, recently molecular biological and pharmacological knowledges suggesting participation of MCH in controlling energetic homeostasis are being accumulated. That is, it has been reported that expression of mRNA, which is an MCH precursor, was accelerated in the brains of ob/ob mice, db/db mice, $A^y$/a mice and Zucker fatty rats which are model animals of hereditary obesity, and in the brains of fasted mice [Nature, Vol. 380, 243 (1996); Diabetes, Vol. 47, 294 (1998); Biochemical and Biophysical Research Communications, Vol. 268, 88 (2000); Molecular Brain Research, Vol. 92, 43 (2001)].

Acute ventricular administration of MCH to rats was observed to induce accelerated feeding activity [Nature, Vol. 380, 243 (1996)] and chronic administration invites obesity accompanied by polyphagy [Proceedings of the National Academy of Sciences of the United States of America, Vol. 99, 3240 (2002)]. Moreover, MCH precursor gene-deficient mice show reduced food ingestion or rise in oxygen consumption per body weight compared to wild type mice. Their low body weight due to decrease in body fat was observed [Nature, Vol. 396, 670 (1998)].

On the contrary, transgenic mice which express excessive MCH precursor develop obesity accompanied by polyphagy and insulin resistance [The Journal of Clinical Investigation, Vol. 107, 379 (2001)]. Consequently, it is suggested that MCH is an important factor for developing obesity and participates in diseases induced by metabolic disorders or respiratory diseases of which one of risk factors is obesity.

Besides, MCH is known to participate also in anxiety-causing action, epilepsy, memory, learning, diuretic action, excretory action of sodium and potassium, oxytocin secreting action, reproduction and reproductive function [Peptides, Vol. 17, 171 (1996); Peptides, Vol. 18, 1095 (1997); Peptides, Vol. 15, 757 (1994); Journal of Neuroendocrinology, Vol. 8, 57 (1996); Critical Reviews in Neurobiology, Vol. 8, 221 (1994)].

MCH causes versatile pharmacological actions through MCH receptors which are present mainly in the central nervous system. As receptors of MCH, at least two types of type 1 receptors (MCH-1R or SLC-1) and type 2 receptors (MCH-2R or SLT) are known [Nature, Vol. 400, 261 (1999); Nature, Vol. 400, 265 (1999); Biochemical and Biophysical Research Communications, Vol. 261, 622 (1999); Nature Cell Biology, Vol. 1, 267 (1999); FEBS Letters, Vol. 457, 522 (1999); Biochemical and Biophysical Research Communications, Vol. 283, 1013 (2001); The Journal of Biological Chemistry, Vol. 276, 20125 (2001); Proceedings of the National Academy of Sciences of the United States of America, Vol. 98, 7564 (2001); Proceedings of the National Academy of Sciences of the United States of America, Vol. 98, 7576 (2001); The Journal of Biological Chemistry, Vol. 276, 34664 (2001); Molecular Pharmacology, Vol. 60, 632 (2001)].

Of those, the pharmacological action observed on rodents is induced mainly via MCH-1R [Genomics, Vol. 79, 785 (2002)]. Because MCH-1R gene-deficient mice chronically administered with MCH do not develop polyphagy or obesity, it is known that controlling of energy exchange by MCH is induced via MCH-1R. Furthermore, the deficiency of MCH-1R is known to promote the activity amount of mice [Proceedings of the National Academy of Sciences of the United States of America, Vol. 99, 3240 (2002)], and its participation in central diseases accompanied by behavioral disorders, for example, attention-deficit hyperactivity disorder, schizophrenia, depression and the like also is strongly suggested [Molecular Medicine Today, Vol. 6, 43 (2000); Trends in Neuroscience, Vol. 24, 527 (2001)].

It is also reported that an autoantibody to MCH-1R is present in serum of vitiligo vulgaris patients [The Journal of Clinical Investigation, Vol. 109, 923 (2002)]. Furthermore, expression of MCH-1R in certain species of cancer cells was reported, and in vivo expression sites of MCH and MCH-1R also suggest MCH's participation in cancer, sleep, vigil, drug dependence and digestive disorders [Biochemical and Biophysical Research Communications, Vol. 289, 44 (2001); Neuroendocrinology, Vol. 61, 348 (1995); Endocrinology, Vol. 137, 561 (1996); The Journal of Comparative Neurology, Vol. 435, 26 (2001)].

Functions of MCH are expressed upon it binding to MCH receptors. Therefore, when its binding to MCH receptor is inhibited, then expression of MCH action can be inhibited. In consequence, substances which are antagonists to binding of MCH with its receptor are useful as preventing or treating agents of those various diseases in which MCH participates, for example, metabolic disorders represented by obesity, diabetes, hormone disorder, hyperlipidemia, gout, fatty liver, hepatitis, cirrhosis; cardiovascular disorders represented by stenocardia, acute or congestive heart failure, myocardial infarction, coronary atherosclerosis, hypertension, renal diseases, electrolyte abnormality; central nervous system or peripheral nervous system disorders represented by bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence, alcoholism; reproductive disorders represented by infertility, preterm labor and sexual dysfunction; and digestive disorders, respiratory disorders, cancer or pigmentation et al.

Conventional known melanin concentrating hormone receptor antagonists are described, for example, in WO01/21577 and WO01/82925. In particular, WO01/82925 discloses the following compounds as a melanin concentrating hormone receptor antagonist.

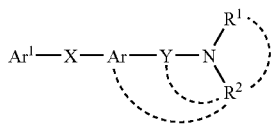

In this reference, an imidazopyridine ring is not exemplified for Ar, and compounds having a specific substituent in a specific site of an imidazopyridine ring as well as their production methods are not concretely disclosed therein. Accordingly, even those skilled in the art who have seen WO01/82925 could not readily reach the knowledge that the imidazopyridine compounds of the invention would have an excellent effect as a melanin concentrating hormone receptor antagonist.

Patent Reference 1: WO01/82925

Patent Reference 2: WO01/21577

The invention is to provide imidazopyridine compounds having an antagonistic effect to the binding of MCH to MCH-1R, and to provide preventing or treating agents comprising the compound for metabolic disorders such as obesity, diabetes, hormone disorder, hyperlipidemia, gout, fatty liver, hepatitis, cirrhosis; cardiovascular disorders such as stenocardia, acute or congestive heart failure, myocardial infarction, coronary atherosclerosis, hypertension, renal diseases, electrolyte abnormality; central nervous system or peripheral nervous system disorders such as bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence, alcoholism; reproductive disorders such as infertility, preterm labor and sexual dysfunction; and other digestive disorders, respiratory disorders, cancer or pigmentation.

DISCLOSURE OF THE INVENTION

We, the present inventors have assiduously studied for developing compounds capable of inhibiting the binding of MCH to MCH-1R, and have found that imidazopyridine compounds which are characterized by having a specific substituent at the 2-, 3- and 6-positions of an imidazopyridine skeleton are novel substances not described in literature, and that the compounds are effective as an MCH-1R antagonist, and on the basis of these findings, we have completed the present invention.

Specifically, the invention provides the following:

(1) An imidazopyridine compound of the following formula [I] or its pharmaceutically-acceptable salt:

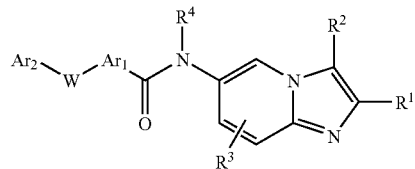

[wherein:

$R^1$ and $R^2$ each independently represent a substituent selected from a group consisting of the following:
1) a hydrogen atom,
2) a halogen atom,
3) a $C_{1-6}$ alkyl group,
4) a $C_{2-6}$ alkenyl group,
5) a $C_{3-8}$ cycloalkyl-$C_{0-4}$ alkyl group,
6) a $C_{1-6}$ alkylamino group,
7) a di-$C_{1-6}$ alkylamino group,
8) a $C_{1-6}$ alkylcarbonylamino group,
9) a $C_{1-6}$ alkylcarbonyl-($C_{1-6}$ alkyl)amino group,
10) a 3- to 8-membered heterocycloalkyl-$C_{0-4}$ alkyl group, and
11) a pyrazolyl-$C_{1-4}$ alkyl group, wherein any hydrogen atom in the alkyl moiety may be optionally substituted with $R^5$, any hydrogen atom in the cycloalkyl or heterocycloalkyl moiety may be optionally substituted with $R^6$, and $R^1$ and $R^2$ must not be hydrogen atoms at the same time, or $R^1$ and $R^2$ together form, along with the carbon atom bonding thereto, a 5- to 8-membered carbon ring optionally substituted with $R^6$;

$R^3$ represents a hydrogen atom, a halogen atom, a $C_{1-6}$ alkyl group, or a $C_{1-6}$ alkyloxy group;

$R^4$ represents a hydrogen atom, or a $C_{1-6}$ alkyl group;

$R^5$ represents a substituent selected from a group consisting of a halogen atom, a cyano group, a hydroxyl group, an amino group, a $C_{1-6}$ alkyl group optionally substituted with a fluorine atom or a hydroxyl group, a mono-$C_{1-6}$ alkylamino group, a di-$C_{1-6}$ alkylamino group, a $C_{1-6}$ alkyloxy group optionally substituted with a fluorine atom, a $C_{1-6}$ alkyloxy-$C_{1-6}$ alkyl group, a $C_{1-6}$ alkyloxycarbonyl group, a $C_{1-6}$ alkyloxycarbonylamino group, a $C_{1-6}$ alkyloxycarbonyl($C_{1-6}$ alkyl)amino group, a $C_{1-6}$ alkylcarbonyl group, a $C_{1-6}$ alkylcarbonyloxy group, a $C_{1-6}$ alkylcarbonylamino group, a $C_{1-6}$ alkylcarbonyl($C_{1-6}$ alkyl)amino group, a carbamoyl group, a mono-$C_{1-6}$ alkylcarbamoyl group, a di-$C_{1-6}$ alkylcarbamoyl group, a carbamoylamino group, a mono-$C_{1-6}$ alkylcarbamoylamino group, a di-$C_{1-6}$ alkylcarbamoylamino group, a mono-$C_{1-6}$ alkylcarbamoyl($C_{1-6}$ alkyl)amino group, a di-$C_{1-6}$ alkylcarbamoyl($C_{1-6}$ alkyl)amino group, a carbamoyloxy group, a mono-$C_{1-6}$ alkylcarbamoyloxy group, a di-$C_{1-6}$ alkylcarbamoyloxy group, a $C_{1-6}$ alkylsulfonyl group, a $C_{1-6}$ alkylsulfonylamino group, a $C_{1-6}$ alkylsulfonyl($C_{1-6}$ alkyl)amino group, a sulfamoyl group, a mono-$C_{1-6}$ alkylsulfamoyl group, a di-$C_{1-6}$ alkylsulfamoyl group, a sulfamoylamino group, a mono-$C_{1-6}$ alkylsulfamoylamino group, a di-$C_{1-6}$ alkylsulfamoylamino group, a mono-$C_{1-6}$ alkylsulfamoyl($C_{1-6}$ alkyl)amino group, and a di-$C_{1-6}$ alkylsulfamoyl($C_{1-6}$ alkyl)amino group;

$R^6$ is $R^5$ or an oxo group;

W represents the following:
a) —$(CH_2)_{m+1}$—,
b) —$(CH_2)_m$—CH=CH—$(CH_2)_n$—, c) —(CH$_2$)$_m$—O—(CH$_2$)$_n$—,
d) —O—(CH$_2$)$_{m+1}$—O—,
e) —(CH$_2$)$_m$—S(O)$_{y1}$—(CH$_2$)$_n$—,
f) —(CH$_2$)$_m$—C(O)—(O)$_{y2}$—(CH$_2$)$_n$—,
g) —(CH$_2$)$_m$—C(O)—NH—(CH$_2$)$_n$—,
h) —(CH$_2$)$_m$—NH—C(O)—(CH$_2$)$_n$—, or
i) —(CH$_2$)$_m$—NH—(CH$_2$)$_n$—, wherein any hydrogen atom in the alkylene moiety of the substituent may be optionally substituted with R$^5$;

m and n each independently indicates an integer of from 0 to 10, satisfying 0≦m+n≦10;

y1 indicates 0, 1 or 2; y2 indicates 0 or 1;

Ar$_1$ is a divalent substituent, representing a) a monocyclic or bicyclic, 3- to 8-membered aromatic or aliphatic heterocyclic group optionally substituted with R$^5$, or b) a monocyclic or bicyclic, 3- to 8-membered aromatic or aliphatic carbocyclic group optionally substituted with R$^5$;

Ar$_2$ represents a 5- or 6-membered aromatic carbocyclic group optionally having a substituent, or a 5- or 6-membered aromatic heterocyclic group optionally having a substituent].

The invention also provides the following:

(2) A method for producing a compound of formula [I], which comprises:

1) a step of amidating a compound of a formula [II]:

[wherein Ar$_{1P}$ represents Ar$_1$ optionally having a protective group; Ar$_{2P}$ represents Ar$_2$ optionally having a substituent; Ar$_1$, Ar$_2$ and W have the same meanings as above], with a compound of a formula [III]:

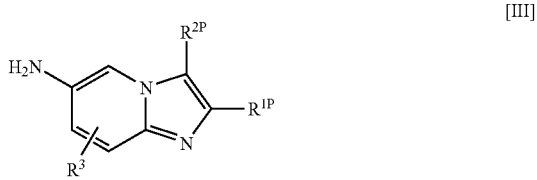

[wherein R$^{1P}$ represents R$^1$ optionally having a protective group; R$^{2P}$ represents R$^2$ optionally having a protective group; R$^1$, R$^2$ and R$^3$ have the same meanings as above];

2) when R$^4$ is not a hydrogen atom, a step of condensing the compound obtained in the previous step with a compound of a formula [IV]:

[wherein X$_1$ represents a leaving group; R$^4$ has the same meaning as above], and 3) optionally a step of removing the protective group;

(3) A melanin concentrating hormone receptor antagonist comprising a compound of (1) as the active ingredient thereof;

(4) A pharmaceutical composition comprising a compound of (1) and a pharmaceutically-acceptable carrier;

(5) A preventing or treating agent comprising a compound of (1) as the active ingredient thereof, for metabolic disorders such as typically obesity, diabetes, hormone disorder, hyper- lipidemia, gout, fatty liver, hepatitis, cirrhosis; cardiovascular disorders such as typically stenocardia, acute or congestive heart failure, myocardial infarction, coronary atherosclerosis, hypertension, renal diseases, electrolyte abnormality; central nervous system or peripheral nervous system disorders such as typically bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence, alcoholism; reproductive disorders such as typically infertility, preterm labor and sexual dysfunction; digestive disorders; respiratory disorders; cancer or pigmentation.

The symbols and the terms used in this description are described below.

"Halogen atom" includes a fluorine atom, a chlorine atom, a bromine atom and an iodine atom.

"C$_{1-6}$ alkyl group" means an alkyl group having from 1 to 6 carbon atoms, or that is, a linear alkyl group having from 1 to 6 carbon atoms or a branched alkyl group having from 3 to 6 carbon atoms, and concretely includes a methyl group, an ethyl group, an n-propyl group, an isopropyl group, an n-butyl group, an isobutyl group, a sec-butyl group, a tert-butyl group, an n-pentyl group, an isopentyl group, a neopentyl group, a tert-pentyl group, a 1-methylbutyl group, a 2-methylbutyl group, a 1,2-dimethylpropyl group, a 1-ethylpropyl group, an n-hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1-ethylbutyl group, a 1,1,2-trimethylpropyl group, a 1,2,2-trimethylpropyl group, a 1-ethyl-2-methylpropyl group, a 1-ethyl-1-methylpropyl group.

"C$_{3-6}$ cycloalkyl group" means a cycloalkyl group having from 3 to 6 carbon atoms, concretely including a cyclopropyl group, a cyclobutyl group, a cyclopentyl group and a cyclohexyl group.

"Oxo group" means a group of forming a carbonyl group along with the carbon atom in organic compounds. For example, for R$^5$, it means a case where two R$^5$'s and the carbon atom bonding to them form a carbonyl group.

"C$_{1-6}$ alkyl group optionally substituted with a fluorine atom" includes a C$_{1-6}$ alkyl group, and a C$_{1-6}$ alkyl group in which a part or all of the hydrogen atoms constituting it are substituted with a fluorine atom. Concretely, the latter C$_{1-6}$ alkyl group substituted with a fluorine atom includes a fluoromethyl group, a difluoromethyl group, a trifluoromethyl group, a 1,2-difluoroethyl group.

"C$_{1-6}$ alkyl group optionally substituted with a hydroxyl group" includes a C$_{1-6}$ alkyl group, and a C$_{1-6}$ alkyl group in which a part of the hydrogen atoms constituting it are substituted with a hydroxyl group. Concretely, the latter C$_{1-6}$ alkyl group substituted with a hydroxyl group includes a hydroxymethyl group, a 2-hydroxyethyl group, a 3-hydroxypropyl group.

"C$_{1-6}$ alkyloxy group optionally substituted with a fluorine atom" includes a C$_{1-6}$ alkyl group or a C$_{1-6}$ alkyl group substituted with a fluorine atom, each bonding to an oxygen atom. Concretely, the C$_{1-6}$ alkyloxy group includes a methoxy group, an ethoxy group, an n-propyloxy group, an isopropyloxy group, an n-butyloxy group, an isobutoxy group, a tert-butoxy group, an n-pentyloxy group; and the C$_{1-6}$ alkyloxy group substituted with a fluorine atom includes a fluoromethoxy group, a difluoromethoxy group, a trifluoromethoxy group, a 1,2-difluoroethoxy group. "Mono-C$_{1-6}$ alkylamino group" means an amino group in which one hydrogen atom is substituted with a C$_{1-6}$ alkyl group. Concretely, it includes a methylamino group, an ethylamino group, an n-propylamino group, an isopropylamino group, an n-butylamino group, a sec-butylamino group, a tert-butylamino group.

"Di-$C_{1-6}$ alkylamino group" means an amino group in which two hydrogen atoms are substituted with a $C_{1-6}$ alkyl group. Concretely, it includes a dimethylamino group, a diethylamino group, an ethylmethylamino group, a di-(n-propyl)amino group, a methylpropylamino group, a diisopropylamino group.

"$C_{1-6}$ alkyloxy-$C_{1-6}$ alkyl group" means a $C_{1-6}$ alkyl group in which one hydrogen atom is substituted with a $C_{1-6}$ alkyloxy group. Concretely, it includes a methoxymethyl group, an ethoxymethyl group, an n-propyloxymethyl group, an ethoxymethyl group, an ethoxyethyl group.

"$C_{1-6}$ alkyloxycarbonyl group" is a $C_{1-6}$ alkyloxy group bonding to a carbonyl group. Concretely, it includes a methoxycarbonyl group, an ethoxycarbonyl group, an n-propyloxycarbonyl group, an isopropyloxycarbonyl group, an n-butyloxycarbonyl group, an isobutoxycarbonyl group, a tert-butoxycarbonyl group, an n-pentyloxycarbonyl group.

"($C_{1-6}$ alkyloxycarbonyl)amino group" is a $C_{1-6}$ alkyloxycarbonyl group bonding to an amino group. Concretely, it includes a methoxycarbonylamino group, an ethoxycarbonylamino group, an n-propyloxycarbonylamino group, an isopropyloxycarbonylamino group, an n-butoxycarbonylamino group, an isobutoxycarbonylamino group, a tert-butoxycarbonylamino group, an n-pentyloxycarbonylamino group.

"($C_{1-6}$ alkyloxycarbonyl)$C_{1-6}$ alkylamino group" is a mono-$C_{1-6}$ alkylamino group in which the hydrogen atom on the nitrogen atom is substituted with a $C_{1-6}$ alkyloxycarbonyl group. Concretely, it includes a (methoxycarbonyl)methylamino group, an (ethoxycarbonyl)methylamino group, an (n-propyloxycarbonyl)methylamino group.

"$C_{1-6}$ alkylcarbonyl group" is a $C_{1-6}$ alkyl group bonding to a carbonyl group. Concretely, it includes an acetyl group, a propionyl group, a butyryl group, an isobutyryl group, a valeryl group, an isovaleryl group, a pivaloyl group.

"$C_{1-6}$ alkylcarbonyloxy group" is a $C_{1-6}$ alkylcarbonyl group bonding to an oxygen atom. Concretely, it includes an acetoxy group, a propionyloxy group, valeryloxy group, an isovaleryloxy group, a pivaloyloxy group.

"$C_{1-6}$ alkylcarbonylamino group" is an amino group in which one hydrogen atom is substituted with a $C_{1-6}$ alkylcarbonyl group. Concretely, it includes an acetamido group, an propionylamino group, an isobutyrylamino group, a valerylamino group, an isovalerylamino group, a pivaloylamino group.

"($C_{1-6}$ alkylcarbonyl)-$C_{1-6}$ alkylamino group" is a mono-$C_{1-6}$ alkylamino group in which the hydrogen atom on the nitrogen atom is substituted with a $C_{1-6}$ alkylcarbonyl group, including a (methylcarbonyl)methylamino group, an (ethylcarbonyl)methylamino group, an (n-propylcarbonyl)methylamino group.

"Mono-$C_{1-6}$ alkylcarbamoyl group" is a carbamoyl group in which one hydrogen atom is substituted with a $C_{1-6}$ alkyl group. Concretely, it includes a methylcarbamoyl group, an ethylcarbamoyl group, an n-propylcarbamoyl group, an isopropylcarbamoyl group, an n-butylcarbamoyl group, a sec-butylcarbamoyl group, a tert-butylcarbamoyl group.

"Di-$C_{1-6}$ alkylcarbamoyl group" is a carbamoyl group in which two hydrogen atoms are substituted with a $C_{1-6}$ alkyl group. Concretely, it includes a dimethylcarbamoyl group, a diethylcarbamoyl group, an ethylmethylcarbamoyl group, a di(n-propyl)carbamoyl group, a methylpropylcarbamoyl group, a diisopropylcarbamoyl group.

"Mono-$C_{1-6}$ alkylcarbamoylamino group" is an amino group in which one hydrogen atom is substituted with a $C_{1-6}$ alkylcarbamoyl group. Concretely, it includes a methylcarbamoylamino group, an ethylcarbamoylamino group, an n-propylcarbamoylamino group, an isopropylcarbamoylamino group, an n-butylcarbamoylamino group, a sec-butylcarbamoylamino group, a tert-butylcarbamoylamino group.

"Di-$C_{1-6}$ alkylcarbamoylamino group" is an amino group in which one hydrogen atom is substituted with a di-$C_{1-6}$ alkylcarbamoyl group. Concretely, it includes a dimethylcarbamoylamino group, a diethylcarbamoylamino group, a di(n-propyl)carbamoylamino group, a diisopropylcarbamoylamino group, a di(n-butyl)carbamoylamino group, a di(sec-butyl)carbamoylamino group, a di(tert-butyl) carbamoylamino group.

"Mono-$C_{1-6}$ alkylcarbamoyl($C_{1-6}$ alkyl)amino group" is a mono-$C_{1-6}$ alkylamino group in which the hydrogen atom on the nitrogen atom is substituted with a mono-$C_{1-6}$ alkylcarbamoyl group. Concretely, it includes a monomethylcarbamoyl(methyl)amino group, a monoethylcarbamoyl(methyl)amino group, a mono(n-propyl)carbamoyl(methyl)amino group.

"Di-$C_{1-6}$ alkylcarbamoyl($C_{1-6}$ alkyl)amino group" is a mono-$C_{1-6}$ alkylamino group in which the hydrogen atom on the nitrogen atom is substituted with a di-$C_{1-6}$ alkylcarbamoyl group. Concretely, it includes a dimethylcarbamoyl(methyl)amino group, a diethylcarbamoyl(methyl)amino group, a di(n-propyl)carbamoyl(methyl)amino group.

"Mono-$C_{1-6}$ alkylcarbamoyloxy group" is a $C_{1-6}$ alkylcarbamoyl group bonding to an oxygen atom. Concretely, it includes a methylcarbamoyloxy group, an ethylcarbamoyloxy group, an n-propylcarbamoyloxy group, an isopropylcarbamoyloxy group, an n-butylcarbamoyloxy group, a sec-butylcarbamoyloxy group, a tert-butylcarbamoyloxy group.

"Di-$C_{1-6}$ alkylcarbamoyloxy group" is a di-$C_{1-6}$ alkylcarbamoyl group bonding to an oxygen atom. Concretely, it includes, a dimethylcarbamoyloxy group, a diethylcarbamoyloxy group, an ethylmethylcarbamoyloxy group, a di(n-propyl)carbamoyloxy group, a methylpropylcarbamoyloxy group, a diisopropylcarbamoyloxy group.

"$C_{1-6}$ alkylsulfonyl group" is a $C_{1-6}$ alkyl group bonding to a sulfonyl group, concretely including a methylsulfonyl group, an ethylsulfonyl group, an n-propylsulfonyl group, an isopropylsulfonyl group, an n-butylsulfonyl group, a sec-butylsulfonyl group, a tert-butylsulfonyl group.

"$C_{1-6}$ alkylsulfonylamino group" is an amino group in which one hydrogen atom is substituted with a $C_{1-6}$ alkylsulfonyl group. Concretely, it includes a methylsulfonylamino group, an ethylsulfonylamino group, an n-propylsulfonylamino group, an isopropylsulfonylamino group, an n-butylsulfonylamino group, a sec-butylsulfonylamino group, a tert-butylsulfonylamino group.

"$C_{1-6}$ alkylsulfonyl($C_{1-6}$ alkyl)amino group" is a $C_{1-6}$ alkylamino group in which the hydrogen atom on the nitrogen atom is substituted with a $C_{1-6}$ alkylsulfonyl group. Concretely, it includes a methylsulfonyl(methyl)amino group, an ethylsulfonyl(methyl)amino group, an (n-propyl)sulfonyl(methyl)amino group.

"Mono-$C_{1-6}$ alkylsulfamoyl group" is a sulfamoyl group with a $C_{1-6}$ alkyl group bonding thereto. Concretely, it includes a monomethylsulfamoyl group, a monoethylsulfamoyl group, a mono(n-propyl)sulfamoyl group, a monoisopropylsulfamoyl group, a mono(n-butyl)sulfamoyl group, a mono(sec-butyl)sulfamoyl group, a mono(tert-butyl)sulfamoyl group.

"Di-$C_{1-6}$ alkylsulfamoyl group" is a sulfamoyl group with a di-$C_{1-6}$ alkyl groups bonding thereto. Concretely, it includes a dimethylsulfamoyl group, a diethylsulfamoyl group, a di(n-propyl)sulfamoyl group, a diisopropylsulfamoyl group, a di(n-butyl)sulfamoyl group, a di(sec-butyl)sulfamoyl group, a di(tert-butyl)sulfamoyl group.

"(Mono-$C_{1-6}$ alkylsulfamoyl)amino group" is an amino group in which one hydrogen atom is substituted with a mono-$C_{1-6}$ alkylsulfamoyl group. Concretely, it includes a (monomethylsulfamoyl)amino group, a (monoethylsulfamoyl)amino group, a [mono(n-propyl)sulfamoyl]amino group, a (monoisopropylsulfamoyl)amino group, a [mono(n-butyl)sulfamoyl]amino group, a [mono(sec-butyl)sulfamoyl]amino group, a (tert-butylsulfamoyl)amino group.

"(Di-$C_{1-6}$ alkylsulfamoyl)amino group" is an amino group in which one hydrogen atom is substituted with a di-$C_{1-6}$ alkylsulfamoyl group. Concretely, it includes a (dimethylsulfamoyl)amino group, a (diethylsulfamoyl)amino group, an (ethylmethylsulfamoyl)amino group, a [di(n-propyl)sulfamoyl]amino group, a (methylpropylsulfamoyl)amino group, a (diisopropylsulfamoyl)amino group.

"Mono-$C_{1-6}$ alkylsulfamoyl($C_{1-6}$ alkyl)amino group" is a mono-$C_{1-6}$ alkylamino group in which the hydrogen atom on the nitrogen atom is substituted with a mono-$C_{1-6}$ alkylsulfamoyl group. Concretely, it includes a monomethylsulfamoyl (methyl)amino group, a monoethylsulfamoyl(methyl)amino group, a mono(n-propyl)sulfamoyl(methyl)amino group.

"Di-$C_{1-6}$ alkylsulfamoyl($C_{1-6}$ alkyl)amino group" is a mono-$C_{1-6}$ alkylamino group in which the hydrogen atom on the nitrogen atom is substituted with a di-$C_{1-6}$ alkylsulfamoyl group. Concretely, it includes a dimethylsulfamoyl(methyl) amino group, a diethylsulfamoyl(methyl)amino group, a di(n-propyl)sulfamoyl(methyl)amino group.

"3- to 8-membered heterocycloalkyl group" includes an azetidinyl group, a pyrrolidinyl group, a piperidinyl group, a piperazinyl group, an imidazolidinyl group, a tetrahydrofuranyl group, a tetrahydropyranyl group, a morpholinyl group, a 1-thia-4-azocyclohexyl group, a 2,5-diazabicyclo[2.2.2]octanyl group.

"Pharmaceutically-acceptable salts" of an imidazopyridine compound of formula [I] means ordinary salts that are acceptable as medicines. Their examples are acid-addition salts to the amino group or acid-addition salts to the nitrogen-containing hetero ring, or base-addition salts to the carboxyl group, if any, in the compound.

The acid-addition salts include inorganic acid salts such as hydrochlorides, sulfates, nitrates, phosphates, perchlorates; organic acid salts such as maleates, fumarates, tartrates, citrates, ascorbates, trifluoroacetates; and sulfonates such as methanesulfonates, isethionates, benzenesulfonates, p-toluenesulfonates.

The base-addition salts include alkali metal salts such as sodium salts, potassium salts; alkaline earth metal salts such as calcium salts, magnesium salts; ammonium salts; and organic amine salts such as trimethylamine salts, triethylamine salts, dicyclohexylamine salts, ethanolamine salts, diethanolamine salts, triethanolamine salts, procaine salts, N,N'-dibenzylethylenediamine salts.

For the purpose of more concretely disclosing the imidazopyridine compounds of the invention hereinunder, various symbols used in formula [I] are described in detail with reference to their examples. The position numbering in the imidazopyridine skeleton is as follows:

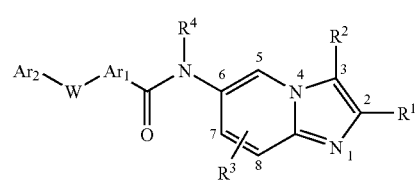

Compounds of Formula [I]

In compounds of formula [I], $R^1$ and $R^2$ each independently represent a substituent selected from a group consisting of the following:
1) a hydrogen atom,
2) a halogen atom,
3) a $C_{1-6}$ alkyl group,
4) a $C_{2-6}$ alkenyl group,
5) a $C_{3-8}$ cycloalkyl-$C_{0-4}$ alkyl group,
6) a $C_{1-6}$ alkylamino group,
7) a di-$C_{1-6}$ alkylamino group,
8) a $C_{1-6}$ alkylcarbonylamino group,
9) a $C_{1-6}$ alkylcarbonyl-($C_{1-6}$ alkyl)amino group,
10) a 3- to 8-membered heterocycloalkyl-$C_{0-4}$ alkyl group, and
11) a pyrazolyl-$C_{1-4}$ alkyl group, wherein any hydrogen atom in the alkyl moiety may be optionally substituted with $R^5$, any hydrogen atom in the cycloalkyl or heterocycloalkyl moiety may be optionally substituted with $R^6$, and $R^1$ and $R^2$ must not be hydrogen atoms at the same time, or $R^1$ and $R^2$ together form, along with the carbon atom bonding thereto, a 5- to 8-membered carbon ring optionally substituted with $R^6$.

$R^5$ includes a halogen atom, a cyano group, a hydroxyl group, an amino group, a $C_{1-6}$ alkyl group optionally substituted with a fluorine atom or a hydroxyl group, a mono-$C_{1-6}$ alkylamino group, a di-$C_{1-6}$ alkylamino group, a $C_{1-6}$ alkyloxy group optionally substituted with a fluorine atom, a $C_{1-6}$ alkyloxy-$C_{1-6}$ alkyl group, a $C_{1-6}$ alkyloxycarbonylamino group, a $C_{1-6}$ alkyloxycarbonyl($C_{1-6}$ alkyl)amino group, a $C_{1-6}$ alkylcarbonyl group, a $C_{1-6}$ alkylcarbonyloxy group, a $C_{1-6}$ alkylcarbonylamino group, a $C_{1-6}$ alkylcarbonyl($C_{1-6}$ alkyl)amino group, a carbamoyl group, a mono-$C_{1-6}$ alkylcarbamoyl group, a di-$C_{1-6}$ alkylcarbamoyl group, a carbamoylamino group, a mono-$C_{1-6}$ alkylcarbamoylamino group, a di-$C_{1-6}$ alkylcarbamoylamino group, a mono-$C_{1-6}$ alkylcarbamoyl($C_{1-6}$ alkyl)amino group, a di-$C_{1-6}$ alkylcarbamoyl ($C_{1-6}$ alkyl)amino group, a carbamoyloxy group, a mono-$C_{1-6}$ alkylcarbamoyloxy group, a di-$C_{1-6}$ alkylcarbamoyloxy group, a $C_{1-6}$ alkylsulfonyl group, a $C_{1-6}$ alkylsulfonylamino group, a $C_{1-6}$ alkylsulfonyl($C_{1-6}$ alkyl)amino group, a sulfamoyl group, a mono-$C_{1-6}$ alkylsulfamoyl group, a di-$C_{1-6}$ alkylsulfamoyl group, a sulfamoylamino group, a mono-$C_{1-6}$ alkylsulfamoylamino group, a di-$C_{1-6}$ alkylsulfamoylamino group, a mono-$C_{1-6}$ alkylsulfamoyl($C_{1-6}$ alkyl)amino group, and a di-$C_{1-6}$ alkylsulfamoyl($C_{1-6}$ alkyl)amino group.

$R^5$ is preferably a hydroxyl group, a cyano group, a dimethylamino group, a fluorine atom, a methoxy group, a methoxycarbonyl group, or an ethoxycarbonyl group.

$R^6$ is $R^5$ or an oxo group, preferably a hydroxyl group, a fluorine atom, a methyl group, a methoxy group, a methoxycarbonyl group, an ethoxycarbonyl group, or an oxo group.

In $R^1$ and $R^2$, the heterocycloalkyl moiety in the 3- to 8-membered heterocycloalkyl-$C_{0-4}$ alkyl group is, for example, preferably a tetrahydrofuranyl group, a tetrahydropyranyl group, a morpholinyl group, a pyrrolidinyl group or a piperidinyl group.

$R^1$ is, for example, preferably a $C_{1-6}$ alkyl group, a $C_{3-8}$ cycloalkyl-$C_{0-4}$ alkyl group, a $C_{1-6}$ alkylamino group, a di-$C_{1-6}$ alkylamino group, a $C_{1-6}$ alkylcarbonyl($C_{1-6}$ alkyl) amino group, or a 3- to 8-member heterocycloalkyl-$C_{0-4}$ alkyl group, in which any hydrogen atom in the alkyl moiety may be optionally substituted with $R^5$, or any hydrogen atom in the cycloalkyl moiety or the heterocycloalkyl moiety may be optionally substituted with $R^6$.

$R^1$ is, for example, more preferably a methyl group, an ethyl group, an n-propyl group, an isopropyl group, an n-butyl group, a t-butyl group, a hydroxymethyl group, a 1-hydroxyethyl group, a 1-methyl-1-hydroxyethyl group, a cyclopropyl group, an N-methylacetaminomethyl group, a 2-ethoxycarbonyl-2-propyl group, a 1H-pyridin-2-onylmethyl group, a pyrrolidon-2-onylmethyl group, an N-methyl-methylsulfonylaminomethyl group, a morpholin-4-ylmethyl group, a tetrahydrofuran-3-yl group, a tetrahydrofuran-2-yl group, a 2-methylcyclopropyl group, a 1-methylcyclopropyl group, a 3-methoxycyclobutyl group, a 3-hydroxycyclobutyl group, a 3-oxocyclobutyl group, a methoxymethyl group, a pyrrolidin-1-ylmethyl group, a pyrrolidin-1-ylpropyl group, a dimethylaminomethyl group, a 3-morpholin-4-ylpropyl group, a 3-hydroxypropyl group, a 3-hydroxyprop-1-en-1-yl group, a 3-hydroxy-3-methylbutyl group, a 3-(3-fluoropyrrolidin-1-yl)propyl group, a 3-(3,3-difluoropyrrolidin-1-yl)propyl group, a 3-(1H-pyrazol-1-yl)propyl group, a (2-pyrrolidin-1-ylethoxy)methyl group, a 3-methoxycyclobutyl group, or a 3-hydroxy-3-methylcyclobutyl group; even more preferably a methyl group, an ethyl group, an isopropyl group, a t-butyl group, a hydroxymethyl group, a 1-ethyl-1-hydroxyethyl group, a cyclopropyl group, a tetrahydrofuran-3-yl group, a 3-oxocyclobutyl group, a 3-methoxycyclobutyl group, a methoxymethyl group, a pyrrolidin-1-ylpropyl group, a 3-morpholin-4-ylpropyl group, a 3-hydroxypropyl group, a 3-hydroxy-3-methylbutyl group, a 3-(3-fluoropyrrolidin-1-yl)propyl group, a 3-(3,3-difluoropyrrolidin-1-yl)propyl group, a 3-hydroxy-3-methylcyclobutyl group.

$R^2$ is, for example, preferably a hydrogen atom, a $C_{1-6}$ alkyl group, a $C_{3-6}$ cycloalkyl group, or a 3- to 8-membered heterocycloalkyl-$C_{0-4}$ alkyl group, in which any hydrogen atom in the alkyl moiety may be optionally substituted with $R^5$, and any hydrogen atom in the cycloalkyl moiety or the heterocycloalkyl moiety may be optionally substituted with $R^6$.

Concretely, $R^2$ is, for example, preferably a hydrogen atom, a methyl group, an ethyl group, a hydroxymethyl group, a 1-hydroxyethyl group, a cyclopropyl group, a methoxymethyl group, a cyanomethyl group, or a pyrrolidin-1-ylmethyl group, more preferably a methyl group or an ethyl group.

Examples of the 5- to 8-membered carbon ring that $R^1$ and $R^2$ together form along with the carbon atom to which they bond are as follows:

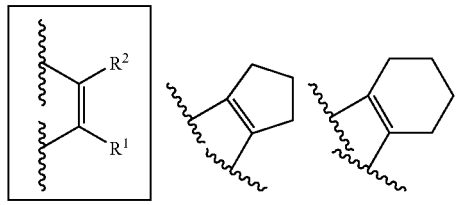

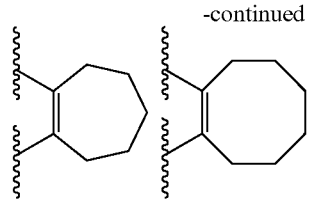
-continued $R^6$ that may bond to the carbon ring is, for example, preferably a halogen atom, (especially a fluorine atom), a hydroxyl group, a $C_{1-6}$ alkyl group or a $C_{1-6}$ alkyloxy group.

$R^3$ includes a hydrogen atom, a halogen atom, a $C_{1-6}$ alkyl group or a $C_{1-6}$ alkyloxy group, concretely, for example, a hydrogen atom, a fluorine atom, chlorine atom, a methyl group, an ethyl group, an n-propyl group, an isopropyl group, an n-butyl group, a t-butyl group, a methoxy group, an ethoxy group, an n-propyloxy group, an isopropyloxy group, or an n-butyloxy group, and preferably a hydrogen atom, a methyl group, or a methoxy group.

$R^4$ is a hydrogen atom or a $C_{1-6}$ alkyl group, concretely including, for example, a hydrogen atom, a methyl group, an ethyl group, an n-propyl group, an isopropyl group, or an n-butyl group; preferably a hydrogen atom, or a methyl group.

W represents the following:
a) $-(CH_2)_{m+1}-$,
b) $-(CH_2)_m-CH=CH-(CH_2)_n-$,
c) $-(CH_2)_m-O-(CH_2)_n-$,
d) $-O-(CH_2)_{m+1}-O-$,
e) $-(CH_2)_m-S(O)_{y1}-(CH_2)_n-$,
f) $-(CH_2)_m-C(O)-(O)_{y2}-(CH_2)_n-$,
g) $-(CH_2)_m-C(O)-NH-(CH_2)_n-$,
h) $-(CH_2)_m-NH-C(O)-(CH_2)_n-$, or
i) $-(CH_2)_m-NH-(CH_2)_n-$.

In W, any hydrogen atom in the alkylene moiety of the substituent of a) to i) may be optionally substituted with $R^5$;
m and n each independently indicates an integer of from 0 to 10, satisfying $0 \leq m+n \leq 10$;
y1 indicates 0, 1 or 2; y2 indicates 0 or 1.

$R^5$ with which the alkylene moiety in W may be optionally substituted includes, for example, a methyl group, an ethyl group, a hydroxyl group, a fluorine atom, a cyclohexyl group, a t-butoxycarbonyl group, preferably a hydroxyl group, a fluorine atom, a methyl group.

In W;
a) includes, for example, $-(CH_2)-$, $-(CH_2)_2-$, $-(CH_2)_3-$, $-(CH_2)_4-$, $-(CH_2)_5-$, $-(CH_2)_6-$, $-(CH_2)_7-$, $-(CH_2)_8-$, $-(CH_2)_9-$, $-(CH_2)_{10}-$, $-CH(OH)-CH_2-$, $-CHF-CH_2-$, $-CF_2CH_2-$, $-CH_2-CH(OH)-$, $-CH_2-CHF-$;
b) includes, for example, $-CH=CH-$, $-CH_2-CH=CH-$, $-(CH_2)_2-CH=CH-$, $-CF=CF-$, $-CF=CH-$, $-CH=CF-$;
c) includes, for example, $-CH_2-O-$, $-CH(CH_3)-O-$, $-O-CH_2-$, $-O-$, $-CH_2-O-CH_2-$, $-(CH_2)_2-O-$;
d) includes, for example, $-O-CH_2-O-$, $-O-(CH_2)_2-O-$, $-O-(CH_2)_3-O-$, $-O-(CH_2)_4-O-$;
e) includes, for example, $-CH_2-S-$, $-CH_2-SO_2-$, $-SO_2-$;
f) includes, for example, $-CO-$, $-CO-CH_2-$, $-CH_2-C(O)-O-$, $-CH_2-C(O)-$;
g) includes, for example, $-CH_2-C(O)-NH-$, $-C(O)-NH-$;

h) includes, for example, —CH$_2$—NH—C(O)—, —NH—C(O)—;

i) includes, for example, —CH$_2$—NH—.

Of those mentioned above, W is, for example, preferably —CH$_2$—CH$_2$—, —CH$_2$—CH$_2$—CH$_2$—, —CH$_2$—CH$_2$—CH$_2$—CH$_2$—, —CH$_2$—CH$_2$—CH$_2$—CH$_2$—CH$_2$—, —CH$_2$—CH(OH)—, —CHF—CH$_2$—, —CH(OH)—CH$_2$—CH$_2$—CHF—, —CF$_2$—CH$_2$—, —CH═CH—, —CF═CH—, —CH═CF—, —CF═CF—, —CH$_2$—O—, —O—CH$_2$—, —O—, —CH(CH$_3$)—O—, —O—(CH$_2$)$_2$—O—, —CH$_2$—S—, —SO$_2$—, —CO—CH$_2$—, —C(O)—NH—, —NH—C(O)—, —CH$_2$—NH—; more preferably —CH═CH—, —O—, —O—CH$_2$—, —CH$_2$—O—, —CH$_2$—S—, —CF═CH—, —CH═CF—, —CHF—CH$_2$—, —CH$_2$—CHF—; even more preferably —CH$_2$—O—, —CH═CH—, —CH═CF—, —O—.

Ar$_1$ is a divalent substituent, representing a) a monocyclic or bicyclic, 3- to 8-membered aromatic or aliphatic heterocyclic group optionally substituted with R$^5$, or b) a monocyclic or bicyclic, 3- to 8-membered aromatic or aliphatic carbocyclic group optionally substituted with R$^5$.

Specifically, Ar$_1$ is a group derived from a monocyclic or bicyclic, 3- to 8-membered aromatic or aliphatic hetero-ring by removing two hydrogen atoms therefrom; or a group derived from a monocyclic or bicyclic, 3- to 8-membered aromatic or aliphatic carbon-ring by removing two hydrogen atoms therefrom.

In Ar$_1$;

the aromatic or aliphatic hetero-ring for a) includes, for example, rings of aziridine, oxaziridine, 2H-aziridine, diaziridine, azetidine, furan, isoxazole, oxazole, isothiazole, thiazole, 1H-imidazole, 1H-[1,2,4]triazole, 2H-[1,2,3]triazole, 1H-pyrazole, 1H-pyrrole, [1,3,4]thiadiazole, [1,2,4]thiadiazole, [1,3,4]oxadiazole, [1,2,4]oxadiazole, 2H-tetrazole, thiophene, pyridine, pyrimidine, pyrazine, pyridazine, [1,2,4]triazine, [1,2,4,5]tetrazine, 2H-1,4-oxazine, 1,2-dihydropyridine, 1,6-dihydropyridazine, 1,6-dihydropyrimidine, 1,2-dihydropyrimidine, 1H-1,2,4-triazepine, 1H-1,2-diazepine, thiepine, oxepine, 1H-azepine, azocine, 1H-indole, 1H-benzimidazole, benzoxazole, benzothiazole, benzofuran, 1-benzothiophene, indolidine, 7H-purine, imidazo[1,2-b]pyridazine, imidazo[1,2-a]pyridine, 2,3-dihydro-1H-isoindole, quinazoline, quinoxaline, quinoline, 3,4-dihydroquinazoline, 2,3-dihydro-1H-indazole, 4H-chromene, pyrrolidine, piperidine, piperazine.

The aromatic or aliphatic carbon-ring for b) includes, for example, rings of cyclopropane, cyclobutane, cyclopentane, cyclohexane, cycloheptane, benzene, indene, naphthalene.

R$^5$ with which Ar$_1$ may be substituted includes, for example, preferably a halogen atom, a hydroxyl group, an amino group, an oxo group, a trifluoromethyl group, a hydroxy-C$_{1-6}$ alkyl group, a C$_{1-6}$ alkyl group, a C$_{1-6}$ alkyloxy group, a C$_{1-6}$ alkyloxy-C$_{1-6}$ alkyl group.

Ar$_1$ is preferably a furan-2,4-diyl group, a thiophene-2,4-diyl group, an isoxazole-3,5-diyl group, an oxazole-2,4-diyl group, an oxazole-2,5-diyl group, an isothiazole-3,5-diyl group, a thiazole-2,4-diyl group, a thiazole-2,5-diyl group, a 2H-[1,2,3]triazole-2,5-diyl group, a 1H-pyrazole-1,4-diyl group, a 1H-pyrazole-1,3-diyl group, a 1H-pyrrole-1,3-diyl group, a [1,2,4]thiadiazole-3,5-diyl group, a [1,2,4]triazine-3,6-diyl group, a benzoxazole-2,6-diyl group, a benzofuran-2,5-diyl group, a benzofuran-2,6-diyl group, 11-benzothiophene-2,5-diyl group, a 1-benzothiophene-2,6-diyl group, an imidazo[1,2-b]pyridazine-2,6-diyl group, an imidazo[1,2-b]pyridazine-2,7-diyl group, an imidazo[1,2-a]pyridine-2,6-diyl group, an imidazo[1,2-a]pyridine-2,7-diyl group, a quinazoline-2,6-diyl group, a quinazoline-2,7-diyl group, a quinoxaline-2,6-diyl group, a quinoxaline-2,7-diyl group, a quinoline-2,6-diyl group, a piperidine-1,4-diyl group, a piperazine-1,4-diyl group, a 2-oxo-1,2-dihydropyridine-1,4-diyl group, a 3-oxo-1,6-dihydropyridazine-2,5-diyl group, a 4-oxo-3,6-dihydropyrimidine-3,6-diyl group, a 2-oxo-1,2-dihydropyrimidine-1,4-diyl group, a 4-oxo-3H-quinazoline-3,7-diyl group, a 3-methyl-4-oxo-3H-quinazoline-2,6-diyl group, a 3-methyl-4-oxo-3H-quinazoline-2,7-diyl group, a 3-oxo-1,2-dihydroindazole-2,6-diyl group, a 2-oxo-pyrrolidine-1,4-diyl group, a 1-oxo-2,3-dihydroisoindole-2,5-diyl group, a 1,4-phenylenediyl group, a 2-methoxy-1,4-phenylenediyl group, a 2-methyl-1,4-phenylenediyl group, a 2-fluoro-1,4-phenylenediyl group, a 2-chloro-1,4-phenylenediyl group, a pyridine-2,5-diyl group, a 6-chloro-pyridine-2,5-diyl group, a pyrimidine-2,5-diyl group, a pyrazine-2,5-diyl group, a pyridazine-3,6-diyl group, a 2,6-naphthalene-diyl group, a 2,7-naphthalene-diyl group, a 1H-imidazole-1,4-diyl group, a [1,3,4]thiadiazole-2,5-diyl group, a [1,3,4]oxadiazole-2,5-diyl group, a 1H-indole-2,5-diyl group, a 1H-benzimidazole-2,5-diyl group, a benzoxazole-2,5-diyl group, a benzothiazole-2,6-diyl group, a benzothiazole-2,5-diyl group, a pyrrolidine-1,3-diyl group, an azetidine-1,3-diyl group, a 1H-[1,2,4]triazole-1,3-diyl group, a 4-methyl-2H-[1,2,3]triazole-2,5-diyl group, a [1,2,4]oxadiazole-3,5-diyl group, a 2H-tetrazole-2,5-diyl group, a 5-methyl-1H-pyrazole-1,4-diyl group, a 1,4-cyclohexylene group, a 1,3-cyclopentylene group; more preferably a 1,4-phenylenediyl group, a thiazole-2,4-diyl group, a 2-oxo-1,2-dihydropyridine-1,4-diyl group, a 2-methoxy-1,4-phenylenediyl group, a 2-methyl-1,4-phenylenediyl group, a piperidine-1,4-diyl group, an azetidine-1,3-diyl group, a 2-fluoro-1,4-phenylenediyl group, a 2-chloro-1,4-phenylenediyl group, a pyridine-2,5-diyl group, a 6-chloro-pyridine-2,5-diyl group, a pyrimidine-2,5-diyl group, a pyrazine-2,5-diyl group, a pyridazine-3,6-diyl group, a 1H-imidazole-1,4-diyl group, a [1,3,4]thiadiazole-2,5-diyl group, a [1,3,4]oxadiazole-2,5-diyl group, a 1H-indole-2,5-diyl group, a 1H-benzimidazole-2,5-diyl group, a benzoxazole-2,5-diyl group, a benzothiazole-2,6-diyl group, a benzothiazole-2,5-diyl group, a pyrrolidine-1,3-diyl group, a 1H-[1,2,4]triazole-1,3-diyl group, a 4-methyl-2H-[1,2,3]triazole-2,5-diyl group, a [1,2,4]oxadiazole-3,5-diyl group, a 2H-tetrazole-2,5-diyl group, a 5-methyl-1H-pyrazole-1,4-diyl group, a 1,4-cyclohexylene group, a 1,3-cyclopentylene group; even more preferably a 1,4-phenylenediyl group, a 2-fluoro-1,4-phenylenediyl group, a pyridine-2,5-diyl group, a pyrimidine-2,5-diyl group, a pyridazine-3,6-diyl group, a [1,3,4]thiadiazole-2,5-diyl group, a 1H-indole-2,5-diyl group, a pyrrolidine-1,3-diyl group, a benzoxazole-2,5-diyl group, a 1H-benzimidazole-2,5-diyl group.

Ar$_2$ represents a 5- or 6-membered aromatic carbocyclic group optionally having a substituent, or a 5- or 6-membered aromatic heterocyclic group optionally having a substituent.

The aromatic carbon-ring or the aromatic hetero-ring for the aromatic carbocyclic group or the aromatic heterocyclic group for Ar₂ includes, for example, benzene, pyridine, pyrimidine, pyridazine, pyrazine, pyrazole, pyrrole, imidazole, triazole, oxazole, isoxazole, oxadiazole, thiazole, isothiazole, thiadiazole, tetrazole.

The substituent that may bond to Ar₂ includes, for example, a halogen atom such as a chlorine atom, a fluorine atom; a $C_{1-6}$ alkyl group such as a methyl group, an ethyl group, an n-propyl group, an isopropyl group; a $C_{1-6}$ alkyl group substituted with a fluorine atom, such as a fluoromethyl group, a difluoromethyl group, a trifluoromethyl group; a $C_{1-6}$ alkyloxy group such as a methoxy group, an ethoxy group, an isopropyloxy group; a $C_{1-6}$ alkyloxy group substituted with a fluorine atom, such as a difluoromethoxy group, a trifluoromethoxy group; a methylsulfonyl group, an ethylsulfonyl group; a $C_{3-6}$ cycloalkyl group such as cyclopropyl group, a cyclobutyl group, a cyclopentyl group; a $C_{3-6}$ cycloalkyloxy group such as a cyclopropyloxy group, a cyclobutyloxy group; a $C_{1-6}$ alkyl group substituted with a hydroxyl group such as a hydroxymethyl group, a 2-hydroxyethyl group, a 1-hydroxy-1-methylethyl group; a dialkylamino group such as a dimethylamino group, a diethylamino group; a methylsulfinyl group, a methylsulfanyl group, a nitrile group. Of those, preferred are a chlorine group, a fluorine group, a bromine group, a methyl group, an ethyl group, an isopropyl group, a 1-hydroxy-1-methylethyl group, a difluoromethyl group, a trifluoromethyl group, a methoxy group, an ethoxy group, an isopropyloxy group, a difluoromethoxy group, a trifluoromethoxy group, a cyclopropyl group, a cyclopropyloxy group, a methylsulfonyl group, a methylsulfinyl group, a methylsulfanyl group, an ethyl sulfonyl group, a nitrile group, a dimethyl amino group.

Concretely, Ar₂ includes, for example, a phenyl group, a 2-fluorophenyl group, a 3-fluorophenyl group, a 4-fluorophenyl group, a 4-chlorophenyl group, a 3-chlorophenyl group, a 2-chlorophenyl group, a 3,4-difluorophenyl group, a 3,4-dichlorophenyl group, a 2,4-difluorophenyl group, a 2-trifluoromethylphenyl group, a 3-trifluoromethylphenyl group, a 4-trifluoromethylphenyl group, a 4-methoxyphenyl group, a 4-methylsulfonylphenyl group, a 4-methylsulfinylphenyl group, a 4-methylthiophenyl group, a 3-fluoro-4-methoxyphenyl group, a 4-hydroxyphenyl group, a pyridin-2-yl group, a pyridin-3-yl group, a 4-cyclopropylpyridin-2-yl group, a 5-cyclopropylpyridin-2-yl group, a 6-cyclopropylpyridin-3-yl group, a 5-trifluoromethylpyridin-2-yl group, a 4-trifluoromethylpyridin-2-yl group, a 3-trifluoromethylpyridin-2-yl group, a 2-trifluoromethylpyridin-5-yl group, a 6-fluoropyridin-2-yl group, a 5-fluoropyridin-2-yl group, a 3-fluoropyridin-2-yl group, a 2-fluoropyridin-5-yl group, a 3-chloropyridin-6-yl group, a 6-chloropyridin-3-yl group, a 4-chloropyridin-2-yl group, a 2-methoxypyridin-5-yl group, a 2-methoxypyridin-6-yl group, a 3-methoxypyridin-6-yl group, a 4-methoxypyridin-2-yl group, a 3-ethoxypyridin-6-yl group, a 3-isopropoxypyridin-6-yl group, a 2-difluoromethoxypyridin-5-yl group, a 3-difluoromethoxypyridin-6-yl group, a pyrazin-2-yl group, a pyrimidin-2-yl group, a 5-fluoropyrimidin-2-yl group, a 6-trifluoromethylpyrimidin-2-yl group, a 2-trifluoromethylpyrimidin-5-yl group, a pyridazin-3-yl group, a 6-chloropyridazin-3-yl group, a pyrrol-1-yl group, a 1H-imidazol-1-yl group, a 1H-imidazol-2-yl group, a 1H-1,2,4-triazol-1-yl group, an isoxazol-3-yl group, a 1,3,4-oxadiazol-2-yl group, a 5-methyl-1,3,4-oxadiazol-2-yl group, a 1,3-thiazol-2-yl group, a 1,3,4-thiadiazol-2-yl group, a 5-methyl-1,3,4-thiadiazol-2-yl group, a 1H-tetrazol-1-yl group, a 2-methylpyridin-5-yl group, a 3-methylpyridin-6-yl group, a 6-methylpyridin-2-yl group, a 5-ethylpyridin-2-yl group, a 5-isopropylpyridin-2-yl group, a 2-difluoromethylpyridin-5-yl group, a 3-difluoromethylpyridin-6-yl group, a 2-trifluoromethoxypyridin-5-yl group, a 3-trifluoromethoxypyridin-6-yl group, a 4-bromopyridin-2-yl group, a 5-(1-hydroxy-1-methylethyl)pyridin-2-yl group, a 4-methylsulfonylpyridin-2-yl group, a 4-(methylthio)pyridin-2-yl group, a 4-methylsulfinylpyridin-2-yl group, a 4-ethylsulfonylphenyl group, a 5-cyanopyridin-2-yl group, a 5-isopropylpyridin-2-yl group, a 6-dimethylaminopyridin-3-yl group, a 5-cyclopropyloxypyridin-2-yl group, a 5-isopropyloxypyridin-2-yl group.

Ar₂ is preferably a pyrrol-1-yl group, a phenyl group, a 2-fluorophenyl group, a 3-fluorophenyl group, a 4-fluorophenyl group, a 4-chlorophenyl group, a 3,4-difluorophenyl group, a 2,4-difluorophenyl group, a 2-trifluoromethylphenyl group, a 3-trifluoromethylphenyl group, a 4-trifluoromethylphenyl group, a 4-methoxyphenyl group, a 4-methylsulfonylphenyl group, a pyridin-2-yl group, a pyridin-3-yl group, a 6-chloropyridin-3-yl group, a 3-methylpyridin-6-yl group, a 6-methylpyridin-2-yl group, a 5-ethylpyridin-2-yl group, a 5-isopropylpyridin-2-yl group, a 2-difluoromethylpyridin-5-yl group, a 3-difluoromethylpyridin-6-yl group, a 2-fluoropyridin-5-yl group, a 5-fluoropyridin-2-yl group, a 3-fluoropyridin-2-yl group, a 6-fluoropyridin-2-yl group, a 3-chloropyryidin-6-yl group, a 4-chloropyridin-2-yl group, a 4-(methylthio)pyridin-2-yl group, a 2-methoxypyridin-5-yl group, a 2-methoxypyridin-6-yl group, a 3-methoxypyridin-6-yl group, a 4-methoxypyridin-2-yl group, a 2-difluoromethoxypyridin-5-yl group, a 3-difluoromethoxypyridin-6-yl group, a 5-trifluoromethylpyridin-2-yl group, a 6-trifluoromethylpyrimidin-2-yl group, a 2-trifluoromethylpyridin-5-yl group, a 3-trifluoromethylpyridin-2-yl group, a 4-trifluoromethylpyridin-2-yl group, a 5-methyl-1,3,4-thiadiazol-2-yl group, a 1,3-thiazol-2-yl group, a pyrazin-2-yl group, a pyrimidin-2-yl group, a 5-fluoro-pyrimidin-2-yl group, a pyridazin-3-yl group, a 6-chloropyridazin-3-yl group, a 4-cyclopropylpyridin-2-yl group, a 5-cyclopropylpyridin-2-yl group, a 6-cyclopropylpyridin-3-yl group, a 4-bromopyridin-2-yl group; more preferably a phenyl group, a 6-chloropyridin-3-yl group, a 4-chloropyridin-2-yl group, a 5-fluoropyridin-2-yl group, a 3-fluoropyridin-2-yl group, a 6-fluoropyridin-2-yl group, a 5-methyl-1,3,4-thiadiazol-2-yl group, a 5-fluoro-pyrimidin-2-yl group, a 6-methylpyridin-2-yl group, a 1,3-thiazol-2-yl group, a 3-difluoromethoxypyridin-6-yl group, a 4-fluorophenyl group, a 4-chlorophenyl group, a 4-trifluoromethylphenyl group, a 4-methoxyphenyl group, a 4-(methylthio)pyridin-2-yl group, a 4-methylsulfonylphenyl group, a pyridin-2-yl group, a pyridin-3-yl group, a 2-fluoropyridin-5-yl group, a 3-fluoropyridin-6-yl group, a 3-chloropyridin-6-yl group, a 2-methoxypyridin-5-yl group, a 3-methoxypyridin-6-yl group, a 5-trifluoromethylpyridin-2-yl group, a 3-trifluoromethylpyridin-2-yl group, a 4-trifluoromethylpyridin-2-yl group, a 2-trifluoromethylpyridin-5-yl group, a 6-chloropyridazin-3-yl group.

Concretely, examples of the compound of formula [I] are shown in Table 1 to Table 6.

TABLE 1

| No. | Structural Formula |
|---|---|
| 1 | |
| 2 | |
| 3 | |
| 4 | |
| 5 | |
| 6 | |

TABLE 1-continued
| No. | Structural Formula |
|---|---|
| 7 | 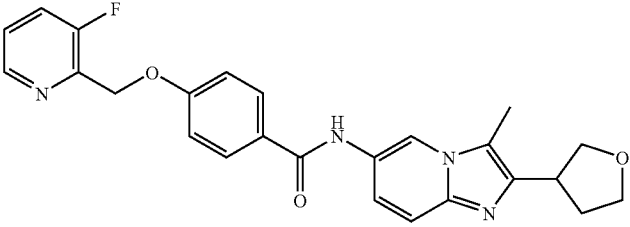 |
| 8 | 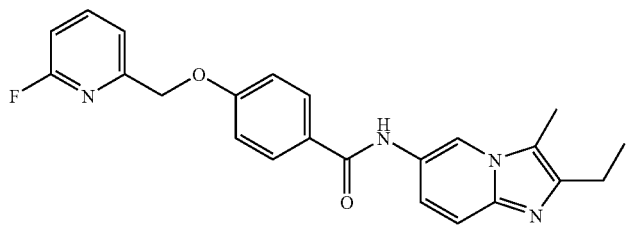 |
| 9 | 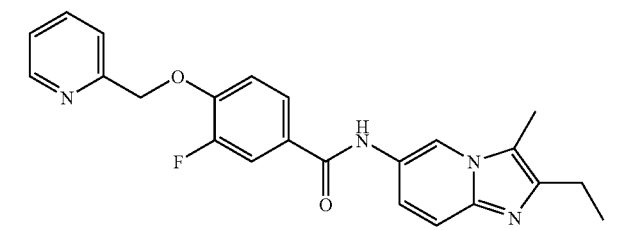 |
| 10 | 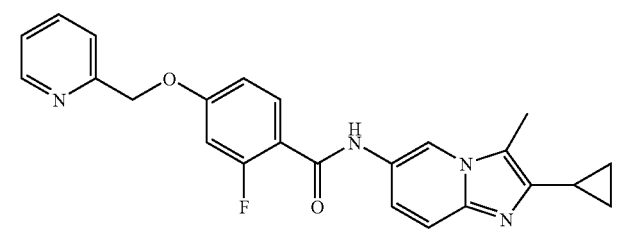 |
| 11 | 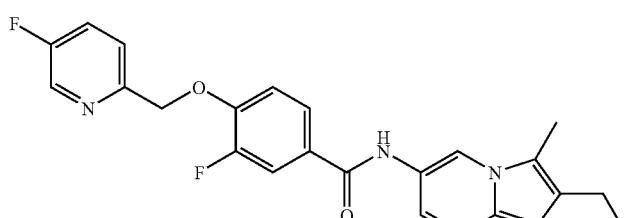 |
| 12 | 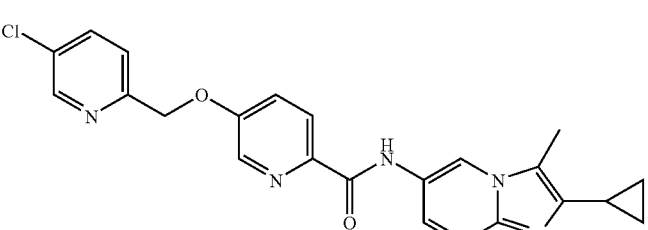 |

TABLE 2
| No | Structural Formula |
|---|---|
| 13 | 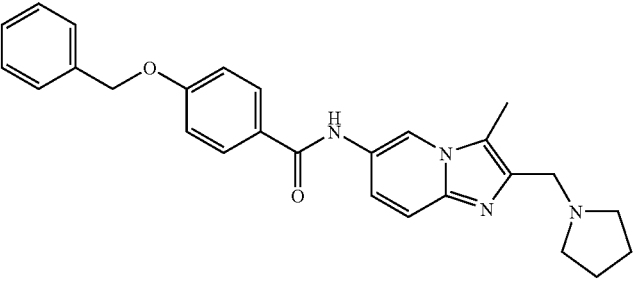 |
| 14 | 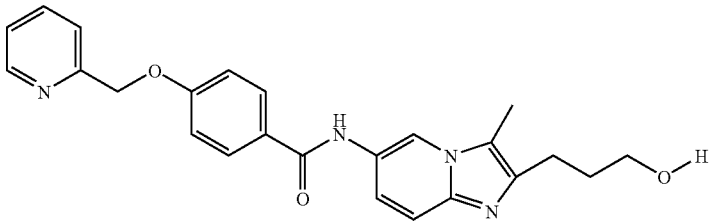 |
| 15 | 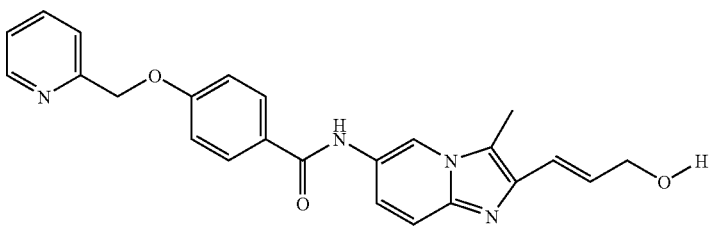 |
| 16 | 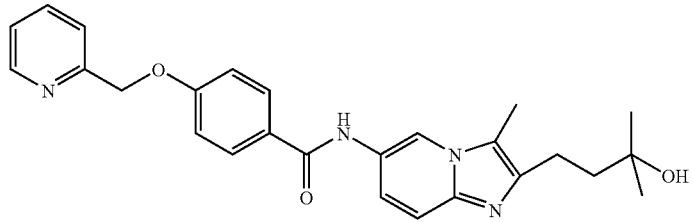 |
| 17 | 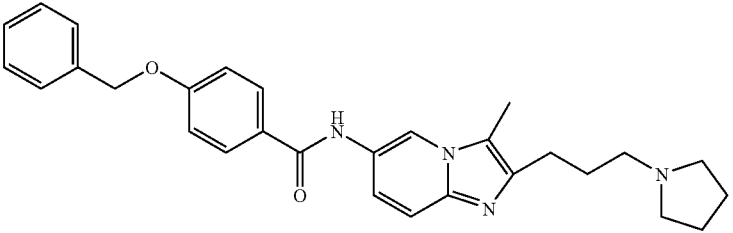 |
| 18 | 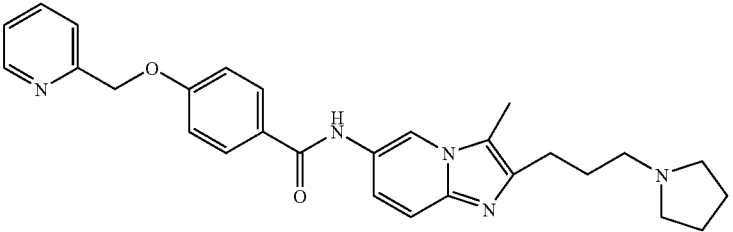 |

TABLE 2-continued

| No | Structural Formula |
|---|---|
| 19 | |
| 20 | |
| 21 | |
| 22 | |
| 23 | |
| 24 | |

TABLE 2-continued
| No | Structural Formula |
|---|---|
| 25 | 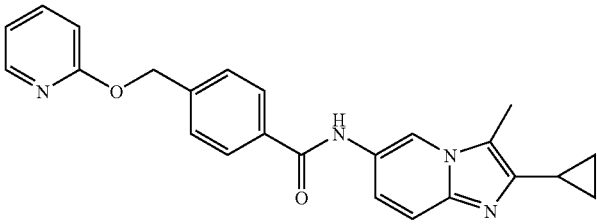 |
| 26 | 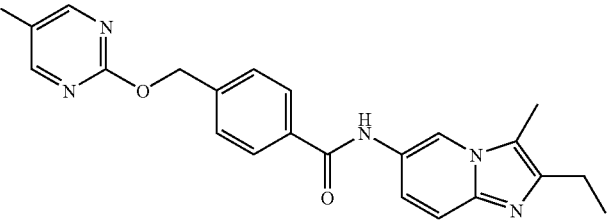 |
| 27 | 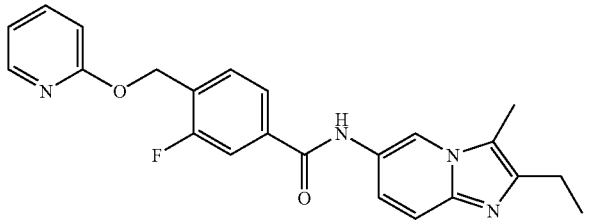 |
| 28 | 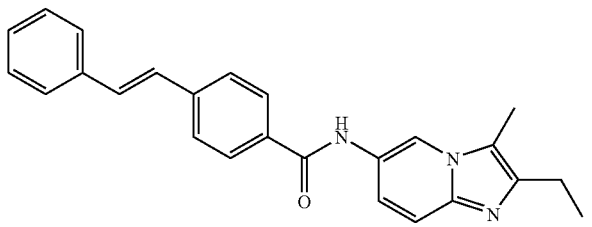 |
TABLE 3
| No | Structural Formula |
|---|---|
| 29 | 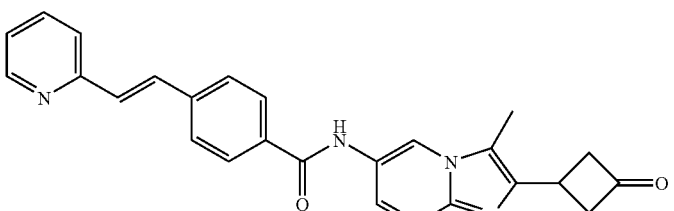 |
| 30 | 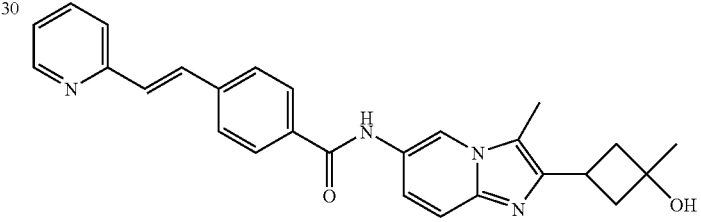 |

TABLE 3-continued
| No | Structural Formula |
|---|---|
| 31 | 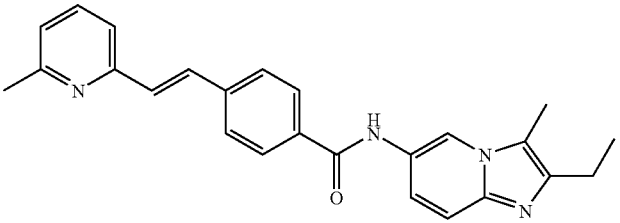 |
| 32 | 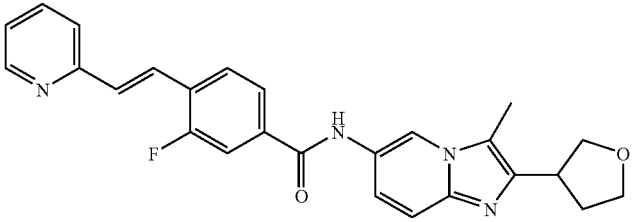 |
| 33 | 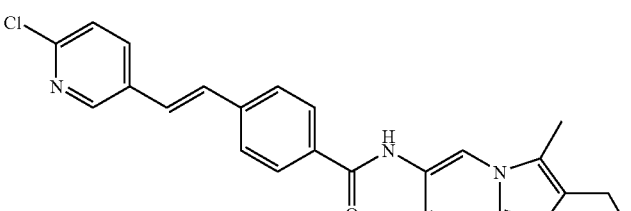 |
| 34 | 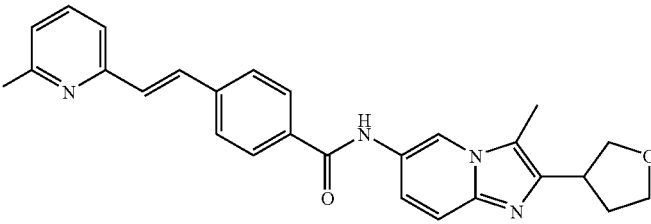 |
| 35 | 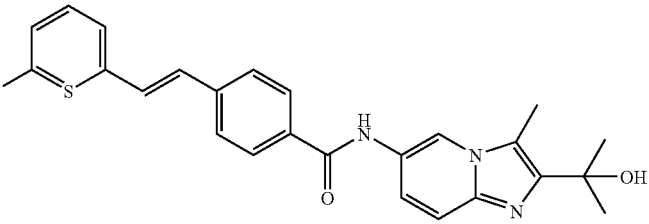 |
| 36 | 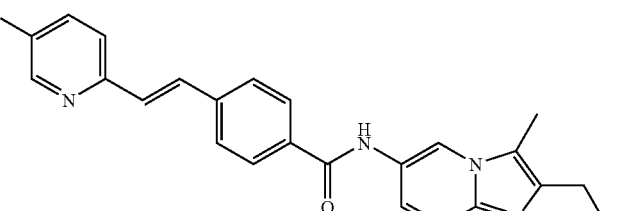 |

TABLE 3-continued

| No | Structural Formula |
|----|--------------------|
| 37 | 5-fluoropyridin-2-yl-CH=CH-C6H4-C(=O)NH-[3-methyl-2-(tetrahydrofuran-3-yl)imidazo[1,2-a]pyridin-6-yl] |
| 38 | 5-fluoropyridin-2-yl-CH=CH-C6H4-C(=O)NH-[3-methyl-2-(2-hydroxypropan-2-yl)imidazo[1,2-a]pyridin-6-yl] |
| 39 | thiazol-2-yl-CH=CH-C6H4-C(=O)NH-(2-ethyl-3-methylimidazo[1,2-a]pyridin-6-yl) |
| 40 | pyridin-2-yl-CH=C(F)-C6H4-C(=O)NH-(2-ethyl-3-methylimidazo[1,2-a]pyridin-6-yl) |
| 41 | pyridin-2-yl-CH=C(F)-C6H4-C(=O)NH-(2-ethyl-3-methylimidazo[1,2-a]pyridin-6-yl) |
| 42 | pyridin-2-yl-CH=C(F)-C6H4-C(=O)NH-[3-methyl-2-(tetrahydrofuran-3-yl)imidazo[1,2-a]pyridin-6-yl] |

TABLE 3-continued

| No | Structural Formula |
|---|---|
| 43 | |
| 44 | |

TABLE 4

| No | Structural Formula |
|---|---|
| 45 | |
| 46 | |
| 47 | |
| 48 | |

TABLE 4-continued
| No | Structural Formula |
|---|---|
| 49 | 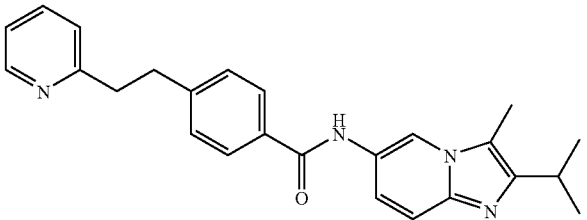 |
| 50 | 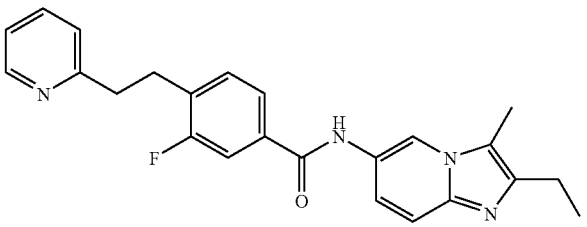 |
| 51 | 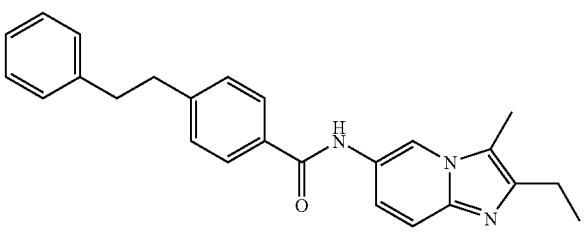 |
| 52 | 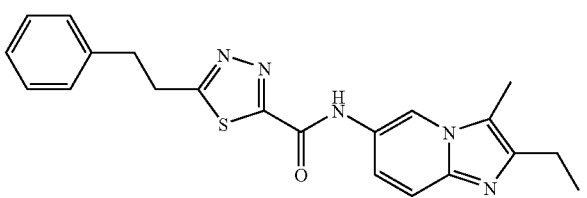 |
| 53 | 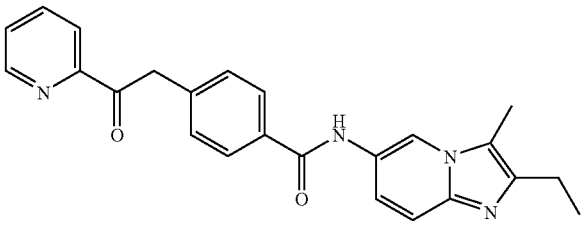 |
| 54 | 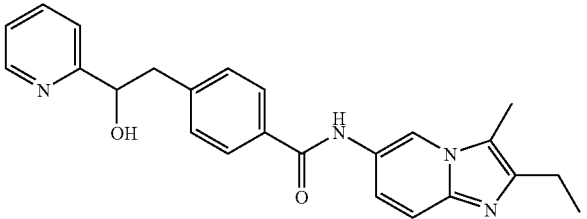 |

TABLE 4-continued
| No | Structural Formula |
|---|---|
| 55 | 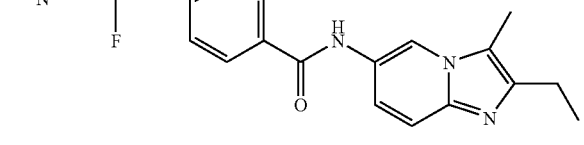 |
| 56 | 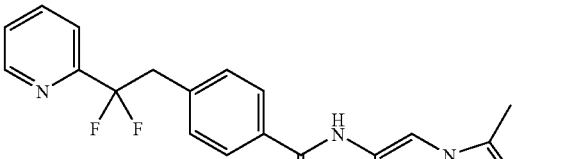 |
| 57 |  |
| 58 | 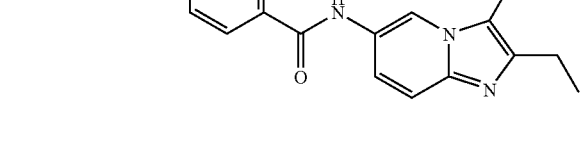 |
| 59 | 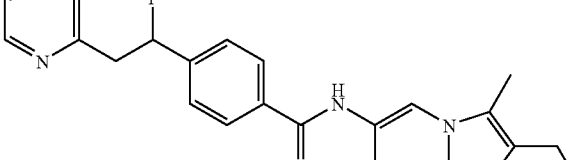 |
| 60 | 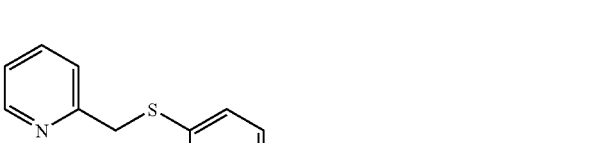 |

TABLE 5
| No | Structural Formula |
|---|---|
| 61 | 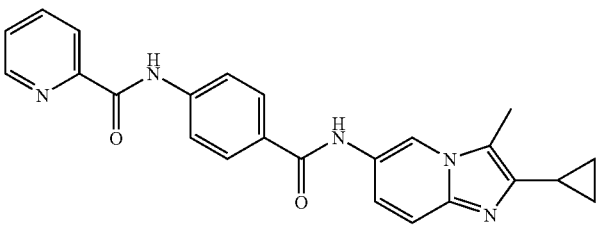 |
| 62 | 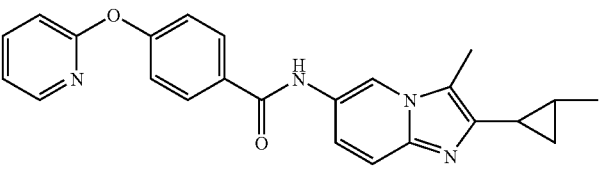 |
| 63 |  |
| 64 | 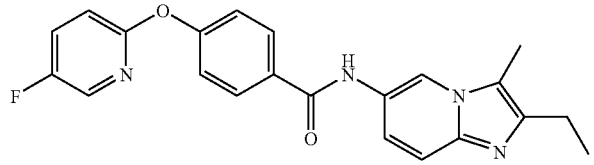 |
| 65 | 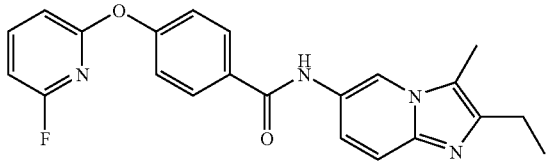 |
| 66 | 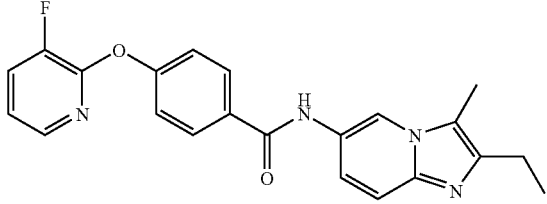 |
| 67 | 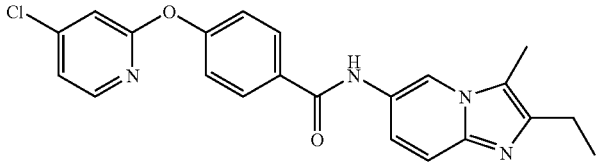 |
| 68 | 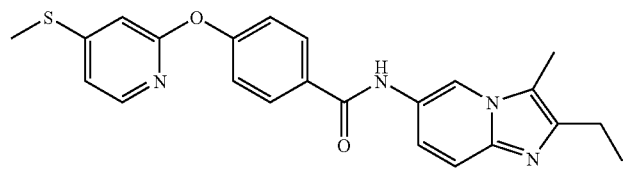 |

TABLE 5-continued

| No | Structural Formula |
|---|---|
| 69 | |
| 70 | |
| 71 | |
| 72 | |
| 73 | |
| 74 | |
| 75 | |

| TABLE 5-continued | |
|---|---|
| No | Structural Formula |
| 76 | |

| TABLE 6 | |
|---|---|
| No | Structural Formula |
| 77 | |
| 78 | |
| 79 | |

Of the compounds of formula [I], preferred are the following:

N-[2-(3-trans-methoxycyclobutyl)-3-methylimidazo[1,2-a]pyridin-6-yl]-4-(pyridin-2-ylmethoxy)benzamide;

4-(5-fluoropyridin-2-ylmethoxy)-N-(2-isopropyl-3-methylimidazo[1,2-a]pyridin-6-yl)benzamide;

N-(2-ethyl-3-methylimidazo[1,2-a]pyridin-6-yl)-3-fluoro-4-(pyridin-2-ylmethoxy)benzamide;

N-(2-ethyl-3-methylimidazo[1,2-a]pyridin-6-yl)-3-fluoro-4-(pyridin-2-yloxymethyl)benzamide;

3-fluoro-N-[3-methyl-2-(tetrahydrofuran-3-yl)imidazo[1,2-a]pyridin-6-yl]-4-((E)-2-pyridin-2-ylvinyl)benzamide;

N-(2-ethyl-3-methylimidazo[1,2-a]pyridin-6-yl)-4-((Z)-2-fluoro-2-pyridin-2-ylvinyl)benzamide;

N-(2-ethyl-3-methylimidazo[1,2-a]pyridin-6-yl)-4-(2-fluoro-2-pyridin-2-ylethyl)benzamide;

N-[3-methyl-2-(tetrahydrofuran-3-yl)imidazo[1,2-a]pyridin-6-yl]-4-(pyridin-2-ylmethylsulfanyl)benzamide;

4-(4-chloropyridin-2-yloxy)-N-(2-ethyl-3-methylimidazo[1,2-a]pyridin-6-yl)benzamide;

N-(2-ethyl-3-methylimidazo[1,2-a]pyridin-6-yl)-4-(4-methylsulfanylpyridin-2-yloxy)benzamide;

N-[3-methyl-2-(3-oxocyclobutyl)imidazo[1,2-a]pyridin-6-yl]-4-((E)-2-pyridin-2-ylvinyl)benzamide;

4-(benzyloxy)-N-[3-methyl-2-(3-pyrrolidin-1-ylpropyl)imidazo[1,2-a]pyridin-6-yl)]benzamide;

N-[3-methyl-2-(3-pyrrolidin-1-ylpropyl)imidazo[1,2-a]pyridin-6-yl]-4-(pyridin-2-ylmethoxy)benzamide;

4-[(E)-2-(6-fluoropyridin-2-yl)vinyl]-N-[3-methyl-2-(tetrahydrofuran-3-yl)imidazo[1,2-a]pyridin-6-yl]benzamide;

4-[(E)-2-(5-fluoropyridin-2-yl)vinyl]-N-[2-(1-hydroxy-1-methylethyl)-3-methylimidazo[1,2-a]pyridin-6-yl]benzamide;

4-[(E)-2-(5-fluoropyridin-2-yl)vinyl]-N-[3-methyl-2-(tetrahydrofuran-3-yl)imidazo[1,2-a]pyridin-6-yl]benzamide;

N-(2-ethyl-3-methylimidazo[1,2-a]pyridin-6-yl)-4-[(Z)-1-fluoro-2-pyridin-2-ylvinyl]benzamide;
4-[(Z)-1-fluoro-2-pyridin-2-ylvinyl]-N-[3-methyl-2-(tetrahydrofuran-3-yl)imidazo[1,2-a]pyridin-6-yl]benzamide;
N-[3-methyl-2-(3-pyrrolidin-1-ylpropyl)imidazo[1,2-a]pyridin-6-yl]-4-[(E)-2-pyridin-2-ylvinyl]benzamide;
N-[2-(3-hydroxy-3-methylcyclobutyl)-3-methylimidazo[1,2-a]pyridin-6-yl]-4-((E)-2-pyridin-2-ylvinyl)benzamide.
More preferred are the following:
N-[2-(3-trans-methoxycyclobutyl)-3-methylimidazo[1,2-a]pyridin-6-yl]-4-(pyridin-2-ylmethoxy)benzamide;
N-[3-methyl-2-(3-pyrrolidin-1-ylpropyl)imidazo[1,2-a]pyridin-6-yl]-4-(pyridin-2-ylmethoxy)benzamide;
N-[3-methyl-2-(3-oxocyclobutyl)imidazo[1,2-a]pyridin-6-yl]-4-((E)-2-pyridin-2-ylvinyl)benzamide;
4-[(E)-2-(5-fluoropyridin-2-yl)vinyl]-N-[3-methyl-2-(tetrahydrofuran-3-yl)imidazo[1,2-a]pyridin-6-yl]benzamide;
4-[(Z)-1-fluoro-2-pyridin-2-ylvinyl]-N-[3-methyl-2-(tetrahydrofuran-3-yl)imidazo[1,2-a]pyridin-6-yl)]benzamide.

Methods for Producing Compounds of Formula [I]

The compounds of formula [I] may be produced, for example, according to Production Method 1 to Production Method 3, as suitably combined.

Production Method 1:

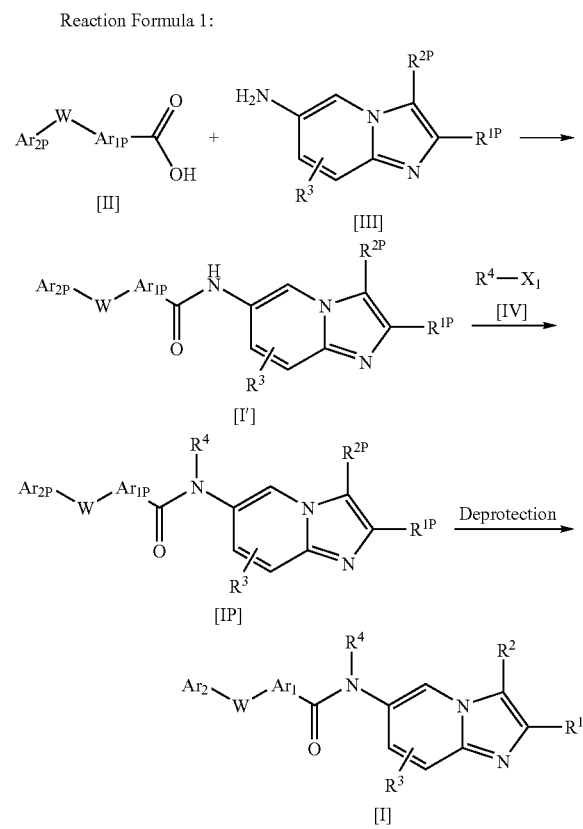

[wherein $X_1$ represents a leaving group, for example, a halogen atom such as a chlorine atom, a bromine atom, an iodine atom; an arylsulfonyloxy group such as a p-toluenesulfonyloxy group, a benzenesulfonyloxy group; an alkanesulfonyloxy group such as a methylsulfonyloxy group, a trifluoromethanesulfonyloxy group; and $R^{1P}$, $R^{2P}$, $R^1$, $R^2$, $R^3$, $R^4$, $Ar_{1P}$, $Ar_1$, W, $Ar_{2P}$ and $Ar_2$ have meanings as above.]

This method includes:
step 1-1: this is a step of amidating a compound of formula [II] with a compound of formula [III] in a solvent to give a compound of formula [I'];
step 1-2: this is a step of optionally condensing the compound of formula [I'] with a compound of formula [IV]; and
step 1-3: this is a step of optionally removing the protective group, if any, from the product.

Step 1-1:
The amidation condensation may be attained according to any conventional known method used for peptide synthesis, for example, according to the methods described in Bases and Experiments of Peptide Synthesis (by Nobuo Izumiya et al., Maruzen, 1983).

This reaction may be attained generally in an inert solvent, which includes, for example, halogenohydrocarbons such as methylene chloride, chloroform; ethers such as diethyl ether, tetrahydrofuran (hereafter abbreviated as "THF"), 1,4-dioxane (hereafter abbreviated as "dioxane"); acetonitrile, dimethylformamide (hereafter abbreviated as "DMF"), dimethylsulfoxide (hereafter abbreviated as "DMSO"), pyridine; or their mixed solvents.

Preferably, the amidation is attained in the presence of a condensing agent. The condensing agent includes, for example, N,N'-dicyclohexylcarbodiimide, 2-chloro-1,3-dimethyl-2-imidazolium chloride, N,N'-diisopropylcarbodiimide, 1-(3-dimethylaminopropyl)-3-ethylcarbodiimide, 1-(3-dimethylaminopropyl)-3-ethylcarbodiimide hydrochloride (hereafter abbreviated as "WSC·HCl"), benzotriazol-1-yloxy-tris-(dimethylamino)phosphonium hexafluorophosphate, benzotriazol-1-yloxy-tris-pyrrolidinophosphonium hexafluorophosphate, bromotris-(dimethylamino)phosphonium hexafluorophosphate, diphenylphosphorazide, 1,1'-carbonyldiimidazole, O-(7-azabenzotriazol-1-yl)-1,1,3,3-tetramethyluronium hexafluorophosphate (hereafter abbreviated as "HATU").

The amount of the condensing agent to be used may be generally from one mol to an excessive molar amount per mol of the compound of formula [III], preferably from 1 mol to 1.5 mols.

The reaction temperature may be generally from –50° C. to 100° C., preferably from –20° C. to 50° C.

The reaction time may be generally from 30 minutes to 7 days, preferably from 1 hour to 24 hours.

In place of the carboxylic acid of formula [II], a reactive derivative of the carboxylic acid may be reacted with a compound of formula [III] to give a compound of formula [I].

The reactive derivative of the carboxylic acid of formula [II] includes, for example, acid halides, mixed acid anhydrides, active esters, active amides. These reactive derivatives may be readily prepared with reference to the above-mentioned Bases and Experiments of Peptide Synthesis (by Nobuo Izumiya et al., Maruzen, 1983).

Acid halides of the compound of formula [II] may be obtained by reacting the compound of formula [II] with a halogenating agent according to a conventional known method. The halogenating agent includes, for example, thionyl chloride, phosphorus trichloride, phosphorus pentachloride, phosphorus oxychloride, phosphorus tribromide, oxalyl chloride, phosgene et al.

Mixed acid anhydrides of the compound of formula [II] may be obtained according to a conventional known method, for example, by reacting the compound of formula [II] with an alkyl chlorocarbonate such as ethyl chlorocarbonate, isobutyl chlorocarbonate, or an aliphatic carboxylic acid chloride such as pivaloyl chloride, in the presence of an amine such as triethylamine.

Active esters of the compound of formula [II] may be obtained, for example, by reacting the compound of formula [II] with an N-hydroxy compound such as N-hydroxysuccinimide, N-hydroxyphthalimide, 1-hydroxybenzotriazole (hereafter abbreviated as "HOBt") or a phenolic compound such as 4-nitrophenol, 2,4-dinitrophenol, 2,4,5-trichlorophenol or pentachlorophenol, in the presence of a condensing agent such as N,N'-dicyclohexylcarbodiimide or 1-(3-dimethylaminopropyl)-3-ethylcarbodiimide according to a conventional known method.

Active amides of the compound of formula [II] may be obtained, for example, by reacting the compound of formula [II] with one equivalent of 1,1'-carbonyldiimidazole or 1,1'-carbonylbis(2-methylimidazole) according to a conventional known method.

The amount of the reactive derivative of the compound of formula [II] to be used may be generally from 0.5 mols to an excessive molar amount per mol of the compound of formula [III], preferably from 1 mol to 1.5 mols.

The amidation may go on in the absence of a base, but for smoothly promoting it, the reaction is effected preferably in the presence of a base.

Especially in the reaction of using an acid halide or a mixed acid anhydride, for example, an organic base such as triethylamine, diisopropylethylamine, pyridine, or an inorganic base such as sodium hydroxide, potassium hydroxide, sodium carbonate, potassium carbonate, sodium hydrogen carbonate may be used.

The amount of the base to be used may be generally from 1 mol to an excessive molar amount per mol of the compound of formula [III], preferably from 1 mol to 4 mols; and when the base is a liquid, then the base may act also as a solvent.

In any reaction of using the above-mentioned reactive derivative, a basic catalyst such as dimethylaminopyridine may be used for promoting the reaction. The amount of the catalyst to be used may be from 0.1 mols to 5 mols per mol of the reactive derivative, preferably from 0.1 mols to 0.5 mols.

The reaction temperature when the reactive derivative is used may be generally from −50° C. to 100° C., preferably from −20° C. to 50° C.

The reaction time when the reactive derivative is used may be generally from 5 minutes to 7 days, preferably from 30 minutes to 24 hours.

Step 1-2:

In case where $R^4$ is not a hydrogen atom, then a compound of formula [I'] may be reacted with a compound of formula [IV] in a solvent in the presence of a base to give a compound of formula [IP]. Concretely, a compound of formula [I'] and a base are stirred with cooling with ice in a solvent for about 10 to 60 minutes, and a compound of formula [IV] is added to the resulting reaction liquid and reacted for 1 to 20 hours.

The solvent includes, for example, ethers such as diethyl ether, THF, dioxane; DMF, DMSO.

The base includes, for example, sodium hydride and potassium hydride; and the compound of formula [IV] includes, for example, methyl iodide, ethyl iodide, methyl p-toluenesulfonate. Step 1-3:

When the compound of formula [IP] has a protective group, then the protective group is removed to give a compound of formula [I].

The method of removing the protective group may vary, depending on the type of the protective group and on the stability of the compound of formula [IP]. For example, according to the methods described in a reference [see Protective Groups in Organic Synthesis, by T. W. Greene, John Wiley & Sons (1981)] or according to methods similar thereto, the deprotection may be attained through solvolysis with an acid or a base of, for example, processing the protected compound with from 0.01 mols to a large excessive amount of an acid, preferably trifluoroacetic acid, formic acid or hydrochloric acid, or with from an equimolar amount to a large excessive amount of a base, preferably potassium hydroxide or calcium hydroxide; or through chemical reduction with a metal hydride complex or through catalytic reduction with a palladium-carbon catalyst or a Raney nickel catalyst.

The compounds of formula [II] may be commercially-available reagents, or may be prepared according to the method described in production method 3, or according to the methods described in Synlett, Vol. 6, 829 (2000); Journal of Medicinal Chemistry, Vol. 41, 1855 (1998); ibid., Vol. 44, 703 (2001); Heterocycles, Vol. 35, 1551, (1994); Synthesis, Vol. 609 (1975), Journal of Heterocyclic Chemistry, Vol. 32, 1563 (1995).

The compounds of formula [III] may be commercially-available reagents, or may be prepared according to the method described in production method 2.

Production Method 2:

Production method 2 is a method for producing the compound of formula [III].

Reaction Formula 2:

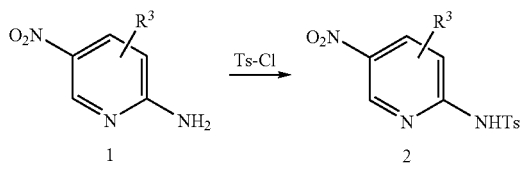

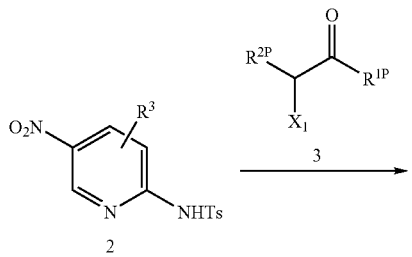

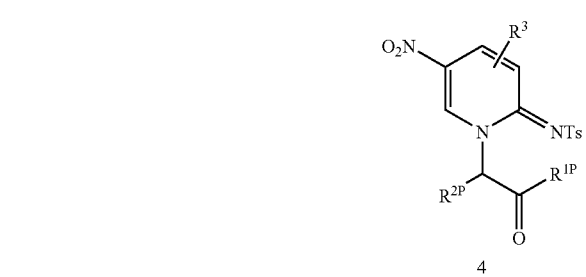

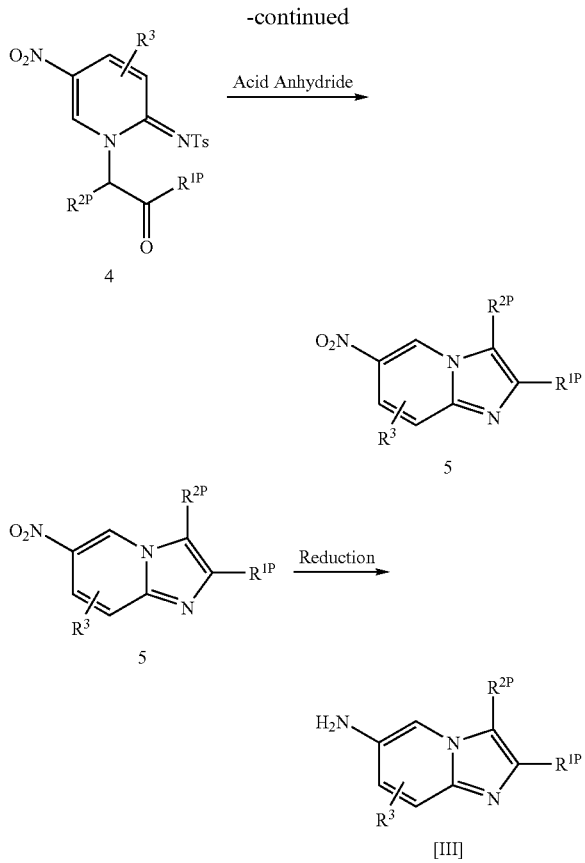

[wherein Ts represents a p-toluenesulfonyl group; $X_1$, $R^{1P}$, $R^{2P}$ and $R^3$ have the same meanings as above.]

Step 2-1:

A compound 1 and p-toluenesulfonyl chloride (TsCl) are heated in a solvent in the presence of a base at 0° C. to 200° C., preferably at 80° C. to 150° C., for 1 to 48 hours, preferably for 1 to 24 hours to obtain a compound 2.

The solvent includes, for example, benzene, toluene, acetone, ethyl acetate; ethers such as dioxane, THF, diethyl ether; halogenohydrocarbons such as methylene chloride, 1,2-dichloroethane, chloroform, carbon tetrachloride.

The base includes, for example, inorganic bases such as sodium carbonate, sodium hydrogencarbonate, calcium carbonate; and organic bases such as pyridine, triethylamine.

The amount of p-toluenesulfonyl chloride to be used may be, for example, from 0.9 to 1.5 mols per mol of the compound 1, preferably from 1 to 1.2 mols. The amount of the base to be used may be, for example, from 1 mol to an excessive molar amount per mol of the compound 1, preferably from 1 to 5 mols.

Step 2-2:

The compound 2 and a compound 3 are reacted in a solvent in the presence of a base at 0° C. to 150° C., preferably at 0° C. to 80° C., for 1 to 48 hours, preferably for 1 to 24 hours to obtain a compound 4.

The solvent includes, for example, THF, DMF, ethanol, DMSO.

The base includes, for example, inorganic bases such as sodium hydride; and organic bases such as diisopropylethylamine and triethylamine.

The amount of the compound 3 to be used may be, for example, from 1 mol to 10 mols per mol of the compound 2, preferably from 1 mol to 5 mols.

The amount of the base to be used may be, for example, from 1 mol to an excessive molar amount per mol of the compound 2, preferably from 1 mol to 5 mols.

Step 2-3:

The compound 4 is heated in the presence or absence of a solvent, but preferably in the presence of a solvent, and in the presence of an acid anhydride, at room temperature to 120° C., preferably at 50° C. to 100° C., for 1 hour to 48 hours, preferably for 1 hour to 24 hours to obtain a compound 5.

The solvent includes, for example, halogenohydrocarbons such as methylene chloride, 1,2-dichloroethane, chloroform, carbon tetrachloride.

The acid anhydride includes, for example, acetic anhydride, trifluoroacetic anhydride.

The amount of the acid anhydride to be used may be, for example, from 1 mol to an excessive molar amount per mol of the compound 4, preferably from 1 mol to 5 mols.

Step 2-4:

The nitro group in the compound 5 is reduced to obtain a compound of formula [III]. For reducing it, for example, the method described in WO02/40019 can be used.

The compound 1 and the compound 3 may be commercially-available reagents, or may be prepared according to the methods described in Production Examples.

Production method 3 is a method for producing the compound of formula [II]. According to the methods described below, various types of compounds can be prepared.

Production Method 3-1:

Reaction Formula 3:

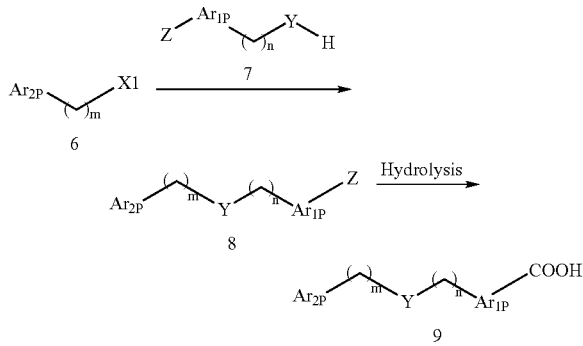

[wherein Y represents —O— or —S—; Z represents a cyano group, a carboxyl group, or —COOR$^9$; R$^9$ represents an alkyl group having from 1 to 6 carbon atoms; m, n, X1, Ar$_{1P}$ and Ar$_{2P}$ have the same meanings as above.]

Specifically, a compound 6 and a compound 7 are condensed in a solvent in the presence of a base to obtain a compound 8. The reaction solvent includes, for example, acetone, methanol, ethanol, benzene, toluene, 1,2-dichloroethane, THF, DMF, and their mixtures with water.

The base includes, for example, inorganic bases such as potassium carbonate, sodium carbonate, cesium carbonate, silver carbonate, potassium fluoride, sodium hydroxide; and organic bases such as diisopropylethylamine, sodium ethoxide, sodium methoxide.

For promoting the reaction, a reaction promoter such as sodium iodide, potassium iodide, 18-crown-6, tetraethylammonium iodide, tetrabutylammonium iodide may be added to the reaction promoter.

The amount of the compound 7 to be used may be, for example, from 1 mol to an excessive molar amount per mol of the compound 6, preferably from 1 mol to 1.5 mols. The amount of the reaction promoter to be used may be, for example, from 0.1 mols to 0.5 mols per mol of the compound 6.

The reaction temperature may be, for example, from room temperature to 150° C., preferably from room temperature to 100° C.

When the compound 8 has an ester group (COOR$^9$) or a cyano group, then the compound of the type may be hydrolyzed according to a conventional known method to give a compound 9.

The compound 6 may be a commercially-available reagent; and the compound 7 may be a commercially-available reagent or may be prepared according to the methods described in Production Examples.

Production Method 3-2:

Reaction Formula 4:

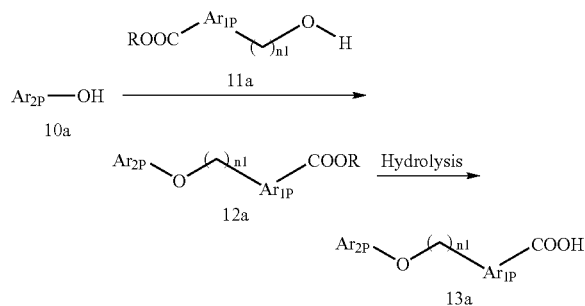

Reaction Formula 5:

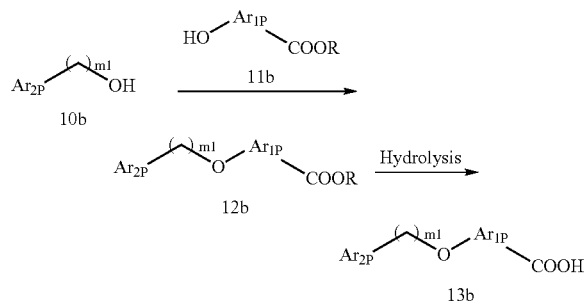

[wherein R represents a lower alkyl group having from 1 to 4 carbon atoms; n1 and m1 are the same or different, each indicating an integer of from 1 to 3; $Ar_{1P}$ and $Ar_{2P}$ have the same meanings as above.]

In the reaction solvent, a compound 10 (10a or 10b) is condensed with a compound 11 (11a or 11b) in the presence of a dialkyl azodicarboxylate and a triaryl phosphine or a trialkyl phosphine to obtain a compound 12 (12a or 12b). Next, the ester moiety in the compound 12 is hydrolyzed to give a compound 13 (13a or 13b).

The dialkyl azodicarboxylate includes, for example, dimethyl azodicarboxylate, diethyl azodicarboxylate, diisopropyl azodicarboxylate, di-t-butyl azodicarboxylate, 1,1'-(azodicarbonyl)dipiperidine. The triaryl phosphine includes, for example, triphenyl phosphine, tritolyl phosphine; and the trialkyl phosphine includes, for example, triethyl phosphine, tributyl phosphine, trioctyl phosphine. Of those, preferred are a combination of diisopropyl azodicarboxylate and triphenyl phosphine; and a combination of 1,1'-(azodicarbonyl)dipiperidine and tributyl phosphine.

The amount of the compound 11 to be used may be, for example, from 1 mol to 3 mols per mol of the compound 10, preferably from 1 mol to 1.5 mols.

The amount of the dialkyl azodicarboxylate and that of the organic phosphorus compound such as triaryl phosphine or trialkyl phosphine to be used may be as follows: The amount of the dialkyl azodicarboxylate may be, for example, from 1 mol to 3 mols per mol of the compound 10, preferably from 1 mol to 1.5 mols; and the amount of the organic phosphorus compound may be, for example, from 1 mol to 3 mols per mol of the compound 10, preferably from 1 mol to 1.5 mols.

The reaction solvent includes, for example, halogenocarbons such as methylene chloride, chloroform, dichloroethane, carbon tetrachloride; aliphatic hydrocarbons such as n-heptane, n-hexane; aromatic hydrocarbons such as benzene, toluene, xylene: ethers such as diethyl ether, THF, dioxane, ethylene glycol dimethyl ether; esters such as methyl acetate, ethyl acetate; and other solvents such as DMF, DMSO.

The reaction temperature may be, for example, from 0° C. to 100° C., preferably from 0° C. to 50° C.; and in general, the reaction may be completed in 2 hours to 24 hours.

The resulting compound 12a or compound 12b is hydrolyzed with a sodium hydroxide solution or the like according to a conventional known method to give a compound 13a or a compound 13b.

The compound 10a, the compound 10b, the compound 11a and the compound 11b may be all commercially-available reagents, or may be prepared according to the methods described in Production Examples.

Production Method 3-3:

Reaction Formula 6:

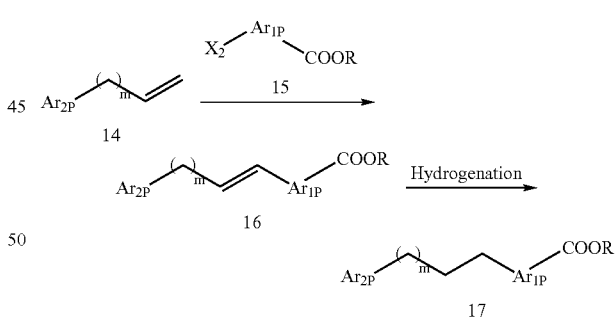

[wherein $X_2$ represents a halogen atom or a trifluoromethanesulfonyloxy group; R, $Ar_{1P}$, $Ar_{2P}$ and m have the same meanings as above.]

A compound 14 and a compound 15 are condensed in a solvent in the presence of a palladium catalyst and a base catalyst to obtain a compound 16 (Heck reaction: Ziegler, C. B., Heck, R. F., J. Org. Chem., 43, 2941(1978)).

The solvent includes, for example, DMF, p-xylene, toluene, acetonitrile, N-methyl-2-pyridone, dioxane, N,N-dimethylacetamide.

The palladium catalyst includes, for example, palladium acetate (optionally combined with a ligand such as triphenyl phosphine, tri-o-tolyl phosphine, tri-n-butyl phosphine, tricyclohexyl phosphine), bis(dibenzylideneacetone)palladium (optionally combined with a ligand such as tri-o-tolyl phosphine), dichlorobis(triphenyl phosphine)palladium, [1,1'-bis(diphenylphosphino)ferrocene]palladium.

The base includes, for example, inorganic bases such as sodium acetate, potassium carbonate, sodium carbonate, calcium carbonate, sodium hydrogencarbonate, cesium carbonate; and organic bases such as triethylamine, tributylamine.

The amount of the palladium catalyst to be used may be, for example, from 0.01 equivalents to 0.5 equivalents relative to one equivalent of the compound 14; and the amount of the base to be used may be, for example, from 1 equivalent to 5 equivalents relative to one equivalent of the compound 14.

In case where the palladium catalyst comprises a ligand, the amount of the ligand may be, for example, from 1 mol to 5 mols per mol of the palladium complex, preferably from 1 mol to 2 mols.

The reaction temperature may be, for example, from room temperature to 130° C., preferably from 80° C. to 130° C.

Next, the compound 16 is optionally reduced through hydrogenation in a solvent to obtain a compound 17, and then the ester moiety in the compound 17 may be hydrolyzed to give the corresponding carboxylic acid.

The hydrogenation may be attained, using a catalyst such as palladium-carbon, Raney nickel or iridium-black, in a hydrogen atmosphere at room temperature for 1 hour to 5 hours.

The amount of the catalyst to be used may be, for example, from 5 to 200 parts by weight relative to 100 parts by weight of the compound 16.

The solvent for the hydrogenation is, for example, methanol, ethanol, tert-butanol, benzene, THF.

The compound 14 and the compound 15 may be commercially-available reagents, or may be prepared according to the methods described in Examples.

Production Method 3-4:

Reaction Formula 7:

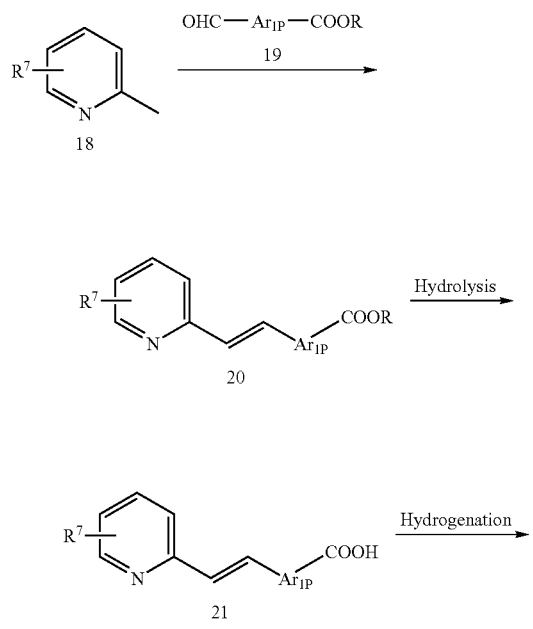

-continued

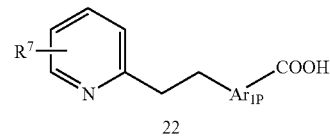

[wherein $R^7$ represents a halogen atom, a $C_{1-6}$ alkyl group, a $C_{1-6}$ alkyl group substituted with a fluorine atom, a $C_{1-6}$ alkyloxy group, a $C_{1-6}$ alkyloxy group substituted with a fluorine atom, a methylsulfonyl group, an ethylsulfonyl group, a $C_{3-6}$ cycloalkyl group, a $C_{3-6}$ cycloalkyloxy group, a $C_{1-6}$ alkyl group substituted with a hydroxyl group, a dialkylamino group, a methylsulfinyl group, a methylsulfanyl group, or a nitrile group; R and $Ar_{1P}$ have the same meanings as above.]

A compound 18 and a compound 19 are condensed in a solvent in the presence of an acid or base catalyst to obtain a compound 20. The compound 20 may be hydrolyzed into a compound 21 according to a conventional known method.

The solvent includes, for example, acetic anhydride, benzoic anhydride, toluene, DMF, acetonitrile, nitrobenzene, methanol, ethanol.

The acid includes, for example, acetic acid, p-toluenesulfonic acid; and the base includes, for example, sodium ethoxide, sodium methoxide, sodium hydride, piperidine, sodium acetate, potassium acetate.

The amount of the acid to be used may be, for example, from 10 parts by weight to 100 parts by weight relative to 100 parts by weight of the compound 18; while the amount of the base to be used may be, for example, from 10 parts by weight to 1000 parts by weight relative to 100 parts by weight of the compound 18. In case where a solvent having a catalytic potency, such as acetic anhydride is used, then the reaction does not require any other catalyst.

The reaction temperature may be, for example, from 100° C. to 250° C., preferably from 160° C. to 250° C., and in general, the reaction may be completed in 4 hours to 24 hours.

Then, the compound 21 may be optionally hydrogenated into a compound 22. The hydrogenation may be attained in a solvent in the presence of a catalyst such as palladium-carbon, platinum dioxide, Raney nickel, iridium-black, in a hydrogen atmosphere for 1 hour to 5 hours.

The amount of the catalyst to be used may be, for example, from 5 to 200 parts by weight relative to 100 parts by weight of the compound 21.

The solvent for the hydrogenation includes, for example, methanol, ethanol, tert-butanol, benzene, THF.

The compound 18 and the compound 19 may be commercially-available reagents, or may be prepared according to the methods described in Production Examples.

Production Method 3-5:

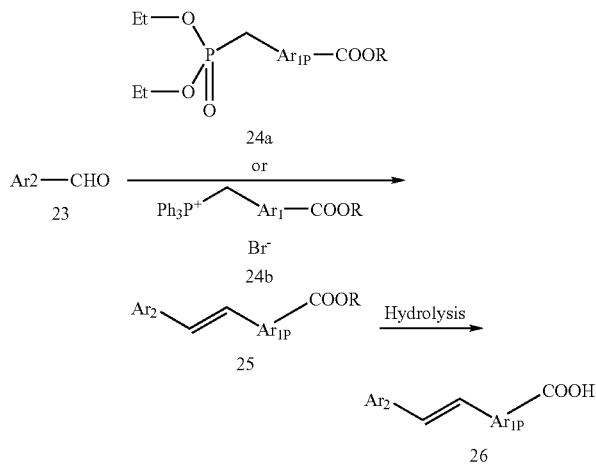

[wherein Ph represents a phenyl group; and R $Ar_{1P}$ and $Ar_2$ have the same meanings as above.]

A compound 23 is reacted with a compound 24a or a compound 24b in a mode of Wittig reaction (A. Maercker, Org. React. 14, 270 (1965)) or Horner-Emmons reaction (L. Horner, H. Hoffmann, W. Klink, H. Erlel, V. G. Toscano, Chem. Ber., 95, 581 (1962); W. S. Wadsworth, Jr., W. D. Emmons, J. Am. Chem. Soc., 83, 1733 (1961)) to obtain a compound 25. Then, the ester moiety in the compound 25 is hydrolyzed to give a compound 26.

The corresponding compound 24a or 24b can be prepared, for example, according to the following method:

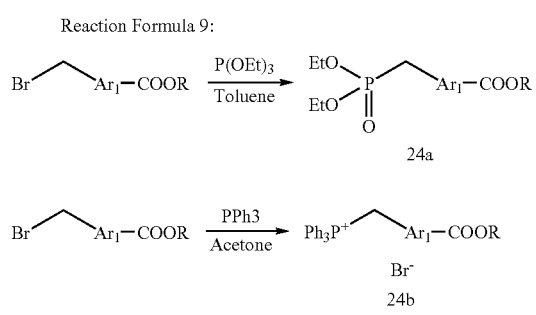

[wherein Et represents an ethyl group; and Ph, R and $Ar_1$ have the same meanings as above.]

A carboxyl group-having arylbenzyl bromide is reacted with triethyl phosphite in toluene (JP-A 11-60537); or it is reacted with triphenyl phosphine in acetone (R. Broos, D. Tavernier, M. Anteunis, J. Chem. Educ., 55, 813 (1978)) to obtain a compound 24a or a compound 24b.

Production Method 3-6:

Production method 3-6 is a method for producing a compound of formula (1) where W is —$(CH_2)_m$—CO—NH— or —NH—CO—$(CH_2)_n$—.

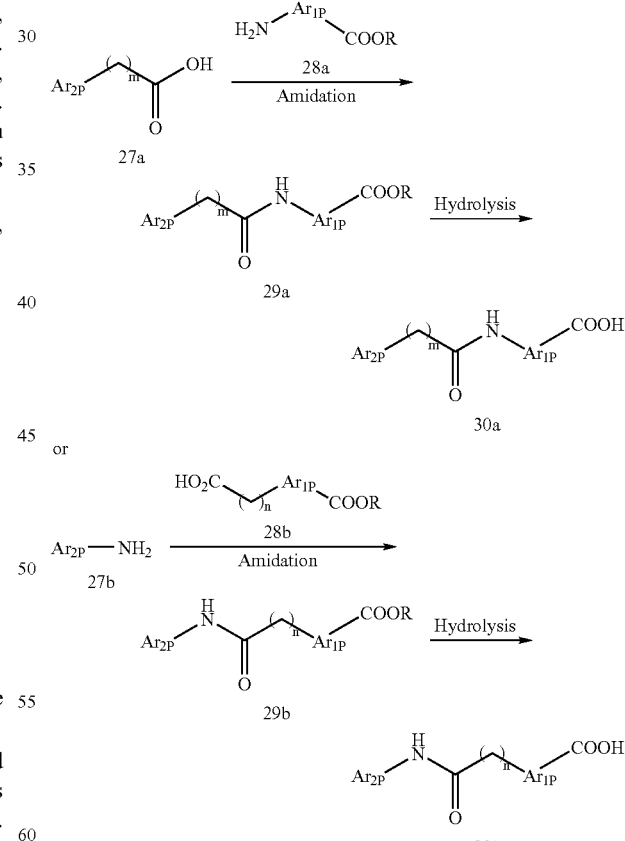

[wherein $Ar_{1P}$, $Ar_{2P}$, R, m and n have the same meanings as above.]

A compound 27 (compound 27a or compound 27b) and a compound 28 (compound 27a or compound 27b) are amidated to obtain a compound 29 (compound 29a or compound 29b). The ester group in the resulting compound is hydrolyzed to obtain a compound 30 (compound 30a or compound 30b).

The amidation may be attained in accordance with the step 1-1. The compound 27a, the compound 27b, the compound 28a and the compound 28b may be all commercially-available reagents or may be prepared according to the methods described in Production Examples.

Production Method 3-7:

Production method 3-7 is an especially effective method for producing a compound of formula (1) where W is —$(CH_2)_m$—O—$(CH_2)_n$— in which m=n=0.

Reaction Formula 11:

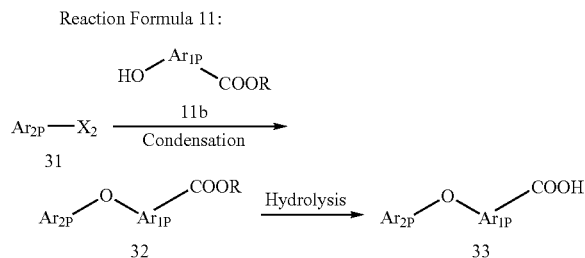

[wherein $X_2$ is a halogen atom; and R, $Ar_{1P}$ and $Ar_{2P}$ have the same meanings as above.] A compound 31 and a compound 11b are condensed in or not in a solvent in the presence of a base to obtain a compound 32.

The reaction solvent includes, for example, acetonitrile, methanol, diethyl ether, THF, DMSO, acetone; and the base includes, for example, potassium carbonate, sodium carbonate, cesium carbonate, sodium methoxide, sodium hydride.

A preferred combination of solvent/base is, for example, acetonitrile/potassium carbonate, methanol/sodium methoxide/DMSO or DMF/sodium hydride.

The amount of the compound 11b to be used may be, for example, from 1 equivalent to 2 equivalents relative to 1 equivalent of the compound 31; and the amount of the base to be used may be, for example, from 1 equivalent to 10 equivalents relative to 1 equivalent of the compound 31.

The reaction temperature may be, for example, from room temperature to 150° C., preferably from 70° C. to 100° C., and in general, the reaction may be completed in 2 hours to 12 hours.

For promoting the reaction, potassium iodide may be added to the reaction system. In that case, the amount of potassium iodide to be added may be, for example, from 0.01 equivalents to 0.5 equivalents relative to 1 equivalent of the compound 31.

The compound 32 may be hydrolyzed into a compound 33 in a known manner.

The compound 31 may be a commercially-available reagent, or may be prepared according to the method described in Examples.

In each reaction of the production method 1 to the production method 3, when the reactants have an amino group, a hydroxyl group, a carboxyl group, an oxo group, a carbonyl group or the like not participating in the reaction, then the amino group, the hydroxyl group, the carboxyl group, the oxo group and the carbonyl group may be suitably protected with a protective group for the amino group, a protective group for the hydroxyl group, a protective group for the carboxyl group, or a protective group for the oxo group or the protective group carbonyl group, and the reaction of the production method 1 to the production method 3 is effected, and after the reaction, the protective group may be removed.

"Amino group-protective group" includes, for example, an aralkyl group such as a benzyl group, a p-methoxybenzyl group, a 3,4-dimethoxybenzyl group, an o-nitrobenzyl group, a p-nitrobenzyl group, a benzhydryl group, a trityl group; a lower alkanoyl group such as a formyl group, an acetyl group, a propionyl group, a butyryl group, a pivaloyl group; a benzoyl group; an arylalkanoyl group such as a phenylacetyl group, a phenoxyacetyl group; a lower alkoxycarbonyl group such as a methoxycarbonyl group, an ethoxycarbonyl group, a propyloxycarbonyl group, a tert-butoxycarbonyl group; an aralkyloxycarbonyl group such as a benzyloxycarbonyl group, a p-nitrobenzyloxycarbonyl group, a phenethyloxycarbonyl group; a lower alkylsilyl group such as a trimethylsilyl group, a tert-butyldimethylsilyl group. Especially preferred are an acetyl group, a pivaloyl group, a benzoyl group, an ethoxycarbonyl group, a tert-butoxycarbonyl group.

"Hydroxyl-protective group" includes, for example, a lower alkyl group such as a methyl group, an ethyl group, a propyl group, an isopropyl group, a tert-butyl group; a lower alkylsilyl group such as a trimethylsilyl group, a tert-butyldimethylsilyl group; a lower alkoxymethyl group such as a methoxymethyl group, a 2-methoxyethoxymethyl group; a tetrahydropyranyl group; a trimethylsilylethoxymethyl group; an aralkyl group such as a benzyl group, a p-methoxybenzyl group, a 2,3-dimethoxybenzyl group, an o-nitrobenzyl group, a p-nitrobenzyl group, a trityl group; an acyl group such as a formyl group, an acetyl group. Especially preferred are a methyl group, a methoxymethyl group, a tetrahydropyranyl group, a trityl group, a trimethylsilylethoxymethyl group, a tert-butyldimethylsilyl group an acetyl group, etc.

"Carboxyl-protective group" includes, for example, a lower alkyl group such as a methyl group, an ethyl group, a propyl group, an isopropyl group, a tert-butyl group; a lower haloalkyl group such as a 2,2,2-trichloroethyl group; a lower alkenyl group such as a 2-propenyl group; an aralkyl group such as a benzyl group, a p-methoxybenzyl group, a p-nitrobenzyl group, a benzhydryl group, a trityl group. Especially preferred are a methyl group, an ethyl group, a tert-butyl group, a 2-propenyl group, a benzyl group, a p-methoxybenzyl group, a benzhydryl group.

"Oxo or carbonyl-protective group" includes, for example, acetals and ketals such as ethylene ketal, trimethylene ketal, dimethyl ketal.

Removal method of the protective group may vary depending on the type of the protective group and on the stability of the compound of formula [I]. For example, according to the methods described in a reference [see Protective Groups in Organic Synthesis, by T. W. Greene, John Wiley & Sons (1981)] or according to methods similar thereto, the deprotection may be attained through solvolysis with an acid or a base of, for example, processing the protected compound with from 0.01 mols to a large excessive amount of an acid, preferably trifluoroacetic acid, formic acid or hydrochloric acid, or with from an equimolar amount to a large excessive amount of a base, preferably potassium hydroxide or calcium hydroxide; or through chemical reduction with a metal hydride complex or through contact reduction with a palladium-carbon catalyst or a Raney nickel catalyst.

The compounds of formula (I) obtained in the manner as above may be readily isolated and purified in any conventional known separation method of, for example, solvent extraction, recrystallization, column chromatography, liquid chromatography or preparative thin-layer chromatography.

Depending on the type of the substituent therein, the compounds of the invention may be in the form of stereoisomers and tautomers such as optical isomers, diastereomers, geometrical isomers; and the compounds of the invention include all those stereoisomers and tautomers and their mixtures.

Pharmacological Test of Compounds of Formula [I]

The usefulness of the compounds of the invention as medicines is verified, for example, by the following pharmacological test example.

PHARMACOLOGICAL TEST EXAMPLE 1

MCH Binding Inhibition Test

A human MCH-1R encoding cDNA sequence [FEBS Letters, Vol. 398, 253 (1996); Biochimica et Biophisica Acta, Vol. 1401, 216 (1998)] was cloned to plasmid vector pEF/myc/cyto (Invitrogen Corporation). The obtained expression vector was transfected to a host cell CHO-K1 (American Type Culture Collection) using Lipofectamine Plus Reagent (Life Technology Inc.) to provide MCH-1R expression cells.

Membrane samples prepared from the MCH-1R expression cells were incubated with each test compound and 50 pM of [$^{125}$I]MCH (NEN Co.), in an assay buffer (50 mM Tris buffer comprising 10 mM magnesium chloride, 2 mM ethylenediamine tetraacetate, 0.01% bacitracin and 0.2% bovine serum albumin; pH 7.4) at 25° C. for an hour, followed by filtration through Glass Filter GF/C (Wattman Co.). After washing the glass filter with 50 mM Tris buffer (pH 7.4) comprising 10 mM magnesium chloride, 2 mM ethylenediamine tetraacetate and 0.04% Tween-20, the radioactive activity on the glass filter was measured. The non-specific binding was measured in the presence of 1 μM human MCH and 50% inhibition concentration ($IC_{50}$ value) of each test compound to the specific [$^{125}$I]MCH binding was determined. The results were as shown in Table 7.

TABLE 7

| Test Compound | $IC_{50}$ (nM) |
| --- | --- |
| Example 9 | 3.4 |
| Example 11 | 2.2 |
| Example 17 | 0.49 |
| Example 25 | 8.4 |
| Example 28 | 1.3 |
| Example 42 | 4.8 |
| Example 48 | 0.47 |
| Example 49 | 6.2 |
| Example 58 | 3.8 |
| Example 59 | 3.8 |
| Example 61 | 4.7 |
| Example 67 | 4.3 |

As in the above, it is understood that the compounds of the invention strongly inhibit the binding of MCH to MCH-1R, and therefore act as an MCH-IR antagonist.

The compounds of the invention have an MCH-1R antagonistic effect, and are useful as preventing and treating agents for metabolic disorders such as obesity, diabetes, hormone disorder, hyperlipidemia, gout, fatty liver, hepatitis, cirrhosis; cardiovascular disorders such as stenocardia, acute or congestive heart failure, myocardial infarction, coronary atherosclerosis, hypertension, renal diseases, electrolyte abnormality; central nervous system or peripheral nervous system disorders such as bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence, alcoholism; reproductive disorders such as infertility, preterm labor and sexual dysfunction; and other digestive disorders, respiratory disorders, cancer or pigmentation; especially as preventing or treating agents for obesity.

Pharmaceutical Composition Containing Compound of Formula (I)

The compound of the invention can be orally or parenterally administered, and can be formulated into preparations suitable to the administration thereof, which may be used as preventing or treating agents for metabolic disorders such as obesity, diabetes, hormone disorder, hyperlipidemia, gout, fatty liver, hepatitis, cirrhosis; cardiovascular disorders such as stenocardia, acute or congestive heart failure, myocardial infarction, coronary atherosclerosis, hypertension, renal diseases, electrolyte abnormality; central nervous system or peripheral nervous system disorders such as bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence, alcoholism; reproductive disorders such as infertility, preterm labor and sexual dysfunction; and other digestive disorders, respiratory disorders, cancer or pigmentation; especially as preventing or treating agents for obesity.

In its clinical use, the compound of the invention may be formulated into various preparations along with a pharmaceutically-acceptable carrier added thereto in accordance with the administration route thereof, and the thus-formulated pharmaceutical composition may be administered. Various conventional additives known in the field of pharmaceutical preparations can be used as the carrier. For example, the carrier includes gelatin, lactose, white sugar, titanium oxide, starch, crystalline cellulose, hydroxypropylmethyl cellulose, carboxymethyl cellulose, corn starch, microcrystalline wax, white petrolatum, magnesium aluminate metasilicate, anhydrous calcium phosphate, citric acid, trisodium citrate, hydroxypropyl cellulose, sorbitol, sorbitan fatty acid esters, polysorbate, sucrose fatty acid esters, polyoxyethylene, hardened castor oil, polyvinylpyrrolidone, magnesium stearate, light silicic anhydride, talc, vegetable oils, benzyl alcohol, gum arabic, propylene glycol, polyalkylene glycol, cyclodextrin and hydroxypropylcyclodextrin.

Preparations to be formed of a mixture of the carrier and the compound of the invention include, for example, solid preparations such as tablets, capsules, granules, powders and suppositories; and liquid preparations such as syrups, elixirs and injections. These may be formulated according to conventional methods known in the field of pharmaceutical preparations. The liquid preparations may also be in such a form that may be dissolved or suspended in water or in any other suitable medium in their use. Especially for injections, if desired, the preparations may be dissolved or suspended in physiological saline water or glucose liquid, and a buffer or a preservative may be optionally added thereto.

The pharmaceutical compositions may contain the compound of the invention in an amount of from 1.0 to 100% by weight, preferably from 1.0 to 60% by weight of the composition, and may contain a pharmaceutically-acceptable carrier in an amount of from 0 to 99.0% by weight, preferably from 40 to 99.0% by weight. The compositions may further contain any other therapeutically-effective compound, for example, a remedial agent for diabetes, a remedial agent for hypertension, and a remedial agent for arteriosclerosis.

In case where the compounds of the invention are used for prevention, treatment or remedy of the above-mentioned diseases, then the dose and the dosing frequency may be varied, depending on the sex, the age, the body weight and the disease condition of the patient and on the type and the range of the intended remedial effect. In general, the dose may be from 0.001 to 50 mg/kg of body weight/day, and it may be administered at a time or in a few times. The dose is preferably from about 0.01 to about 25 mg/kg/day, more preferably from about 0.05 to about 10 mg/kg/day.

Combination Therapy

The compounds of the invention can be used in combination with drugs effective for hypertension, obesity-associated hypertension, hypertension-associated diseases, hypertrophy, left ventricular hypertrophy, metabolic disorders, obesity, obesity-associated diseases and the like (hereafter referred to as "drug for combined use"). Such drugs can be administered simultaneously, separately or in succession, for prevention or treatment of the above-mentioned diseases. When a compound of the invention is used simultaneously with one, two or more of drugs for combined use, they may be formulated into a medical preparation suited for single administration form. Whereas, in combination therapy, a composition containing the compound of the invention and drug(s) for combined use may be administered to the object of medication in different packages, either simultaneously, separately or successively. They may be administered at time interval(s).

Dose(s) of drug(s) for combined use are determinable following clinically adopted dose(s), which can be suitably selected according to the individual object of medication, the administration route, the specific disease, the combination of drugs, and the like. Form of administering drug(s) for combined use is not critical but it is sufficient that the compound of the invention is combined with selected drug(s) for at the time of administration. As a adoptable administration forms, for example, 1) administration of single preparation obtained by simultaneously formulating a compound of the invention and drug(s) for combined use, 2) simultaneous administration of two kinds of preparations obtained by separately formulating a compound of the invention and drug(s) for combined use, via a same administration route, 3) administration at a certain time interval, via a same administration route, of two kinds of preparations obtained by separately formulating a compound of the invention and drug(s) for combined use, 4) simultaneous administration of two kinds of preparations obtained by separately formulating a compound of the invention and drug(s) for combined use, via different administration routes, and 5) administration of two kinds of preparations obtained by separately formulating a compound of the invention and drug(s) for combined use, via different administration routes, at a certain time interval (e.g., administration in an order of the compound of the invention and then the drug(s) for combined use, or in the reversed order) can be adopted. The use ratio of a compound of the invention and drug(s) for combined use can be suitably selected, according to the individual object of medication, the administration route, the disease and others.

As drugs for combined used which can be used in the invention, for example, "drugs for treating diabetes", "drugs for hyperlipidemia", "drugs for hypertension", "anti-obesity drugs" and the like can be mentioned. Two or more such drugs for combined use may be combined in an adequate ratio and used.

"Drugs for treating diabetes" include, for example, 1) PPAR-γ agonists such as glitazones (e.g., ciglitazone, dargli- tazone, englitazone, isaglitazone, MCC-555), pioglitazone, rosiglitazone, troglitazone, BRL49653, CLX-0921, 5-BTZD, GW-0207, LG-100641, LY-300512; 2) biguanides such as metformin, buformin, phenformin; 3) protein tyrosine phosphatase 1B inhibitors; 4) sulfonylureas such as acetohexamide, chloropropamide, diabinese, glibenclamide, glipizide, glyburide, glimepiride, glicilazide, glipentide, gliquidone, glisolamide, trazamide, tolubutamide; 5) meglitinides such as repaglinide, nateglinide; 6) α-glucoside hydroxylase inhibitors such as acarbose, adiposine, camiglibose, emiglitate, miglitol, voglibose, pradimicin-Q, salbostatin, CKD-711, MDL-25, 673, MDL-73, 945, MOR14; 7) α-amylase inhibitors such as tendamistat, trestatin, A1 3688; 8) insulin secretion promoters such as linogliride, A-4166; 9) fatty acid oxidation inhibitors such as clomoxir, etomoxir; 10) A2 antagonists such as midaglizole, isaglidole, deriglidole, idazoxan, earoxan, fluparoxan; 11) insulin or insulin mimetics such as biota, LP-100, novalapid, insulin detemir, insulin lispro, insulin glargine, insulin zinc, Lys-Pro-insulin, GLP-1 (73-7), GLP1 amide (7-36) 12) non-thiazolidinediones such as JT-501, farglitazar; 13) PPARα/γ dual-agonists such as MK-0767, CLX-0940, GW-1536, GW-1929, GW-2433, KRP-297, L-796449, LR-90 and SB219994.

"Drugs for treating hyperlipidemia" include, for example, 1) bile acid absorption promoters such as cholesterylamine, colesevelem, colestipol, crosslinked dextran dialkylaminoalkyl derivatives, Colestid™, LoCholest™, Questran™; 2) HMG-CoA reductase inhibitors such as atorvastatin, itavastatin, fluvastatin, lovastatin, pravastatin, rivastatin, rosuvastatin, simvastatin, ZD-4522; 3) HMG-CoA synthesis inhibitors; 4) cholesterol absorption inhibitors such as snatol ester, β-sitosterol, sterol glucoside, ezetimibe; 5) acyl-coenzyme A.cholesterol acyl transferase inhibitors such as avasimibe, eflucimibe, KY-505, SMP-709; 6) CETP inhibitors such as JTT705, torcetrapib, CP532632, BAY-63-2149, SC-591, SC-795; 7) squalane synthesis inhibitors; 8) antioxidants such as probucol; 9) PPAR-α agonists such as beclofibrate, benzafibrate, syprofibrate, clofibrate, etofibrate, fenofibrate, gemcabene, gemfibrozil, GW-7647, BM-170744, LY-518674, fibric acid derivatives (e.g., Atromid™, Lopid™, Tricor™); 10) FXR receptor antagonists such as GW-4064, SR-103912; 11) LXR receptor agonists such as GW3965, T9013137, XTCO-179628; 12) lipoprotein synthesis inhibitors such as niacin; 13) renin-angiotensin system inhibitors; 14) microsome-triglyceride transport inhibitors; 15) bile acid resorption inhibitors such as BARA1453, SC435, PHA384640, S-435, AZD7706; 16) PPAR-δ agonists such as GW501516, GW590735; 17) triglyceride synthesis inhibitors; 18) MTTP inhibitors such as LAB687, CP346086; 19) low-density lipoprotein receptor inducers; 20) squalane epoxidase inhibitors; 21) thrombocyte agglutination inhibitors; 22) 5-lipoxygenase activated protein inhibitors such as MK-591.

"Drugs for hypertension" include, for example, 1) thiazide diuretics such as chlorothialidon, chlorothiazide, dichlorofenamide, hydrofluorothiazide, indapamide, hydrochlorothiazide; loop diuretics such as bumetanide, ethacrynic acid, flosemide, tolusemide; sodium diuretics such as amyloride, triamuteren; aldosterone antagonist diuretics such as spironolactone, epilenone; 2) β-adrenaline blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, probanolol, sotalol, tartatolol, tilisolol, timolol; 3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, verapamil; 4) angiotensin transferase inhibitors such as benazepril, captopril, cilazapril, delapril, enalapril, fosinopril, imidapril, rosinopril, moexipril, quinapril, quinaprilat, ramipril, perindopril, perindoropril, quanipril, spirapril, tenocapril, trandolapril, zofenopril; 5) neutral endopeptidase inhibitors such as omapatrilat, cadoxatril, ecadotril, fosidotril, sampatrilat, AVE7688, ER4030; 6) endothelin antagonists such as tezosentan, A308165, YM62899; 7) vasodilators such as hydraladine, clonidine, minoxidil, nicotinyl alcohol; 8) angiotensin II antagonists such as candesartan, eporsartan, iribesartan, losartan, pratosartan, tasosartan, telmisartan, balsartan, EXP-3137, FI6828K, RNH6270; 9) α/β adrenalin blockers such as nipradilol, arotinolol, amoslalol; 10) α1 blockers such as terazosin, urapidil, purazosin, bunazosin, trimazosin, doxazosin, naphthopidil, indolamin, WHIP164, XEN010; 11) α2 agonists such as lofexidine, tiamenidine, moxonidine, rilmenidine, guanobenz; and 12) aldosterone inhibitors.

"Anti-obesity drugs" include, for example, 1) 5HT (serotonin) transporter inhibitors such as paroxetine, fluoxetine, fenfluramine, fluvoxamine, sertraline, imipulamin; 2) norepinephrine transporter inhibitors such as GW320659, decipulamin, talsupramin, nomifensin; 3) cannabinoid-1 receptor 1 (CB-1) antagonists/inverse-agonists such as limonabant (Sanofi Synthelabo), SR-147778 (Sanofi Synthelabo), BAY-65-2520 (Bayer), SLV-319 (Sorbei), as well as compounds disclosed in U.S. Pat. No. 5,532,237, U.S. Pat. No. 4,973,587, U.S. Pat. No. 5,013,837, U.S. Pat. No. 5,081,122, U.S. Pat. No. 5,112,820, U.S. Pat. No. 5,292,736, U.S. Pat. No. 5,624,941, U.S. Pat. No. 6,028,084, WO96/33159, WO98/33765, WO98/43636, WO98/43635, WO01/09120, WO01/96330, WO98/31227, WO98/41519, WO98/37061, WO00/10967, WO00/10968, WO97/29079, WO99/02499, WO01/58869, WO02/076949, WO01/64632, WO01/64633, WO01/64634, WO03/006007, WO03/007887, EP-658546; 4) glerin antagonists such as compounds disclosed in WO01/87355, WO02/08250; 5) histamine(H3) antagonists/inverse-agonists such as thioperamide, 3-(1H-imidazol-4-yl)propyl N-(pentenyl)carbonate, clobenpropit, iodofenpropit, imoproxyfen, GT2395, A331440, compounds disclosed in WO02/15905, O-[3-(1H-imidazol-4-yl)propanol]carbamate, piperazine-containing H3-receptor antagonists (Lazewska, D. et al., Pharmazie, 56: 927-32 (2001)), benzophenone derivatives (Sasse, A. et al., Arch. Pharm. (Weinheim) 334: 45-52 (2001)), substituted N-phenylcarbamates (Reidemeister, S. et al., Pharmazie, 55: 83-6 (2000)), proxyfen derivatives (Sasse, A. et al., J. Med. Chem., 43: 3335-43 (2000)); 6) MCH-1R antagonists such as T-226296 (Takeda), SNP-7941 (Synaptic), other compounds disclosed in WO01/82925, WO01/87834, WO02/051809, WO02/06245, WO02/076929, WO02/076947, WO02/04433, WO02/51809, WO02/083134, WO02/094799, WO03/004027, JP-A 2001-226269; 7) MCH-2R agonists/antagonists; 8) NPY1 antagonists such as isopropyl 3-chloro-5-(1-(6-[2-(5-ethyl-4-methyl-thiazol-2-yl)-ethyl]-4-morpholinyl-4-yl-piperidin-2-ylamino)-ethyl)phenyl]carbamate, BIBP3226, BIBO3304, LY-357897, CP-671906, GI-264879, and other compounds disclosed in U.S. Pat. No. 6,001,836, WO96/14307, WO01/23387, WO99/51600, WO01/85690, WO01/85098, WO01/85173, WO01/89528; 9) NPY5 antagonists such as 152804, GW-569180A, GW-594884A, GW-587081X, GW-548118X, FR235,208, FR226928, FR240662, FR252384, 1229U91, GI-264879A, CGP71683A, LY-377897, LY366377, PD-160170, SR-120562A, SR-120819A, JCF-104, H409/22, and other compounds disclosed in U.S. Pat. No. 6,140,354, U.S. Pat. No. 6,191,160, U.S. Pat. No. 6,258,837, U.S. Pat. No. 6,313,298, U.S. Pat. No. 6,337,332, U.S. Pat. No. 6,329,395, U.S. Pat. No. 340,683, U.S. Pat. No. 6,326,375, U.S. Pat. No. 6,329,395, U.S. Pat. No. 6,337,332, U.S. Pat. No. 6,335,345, EP-01010691, EP-01044970, WO97/19682, WO97/20820, WO97/20821, WO97/20822, WO97/20823, WO98/27063, WO00/107409, WO00/185714, WO00/185730, WO00/64880, WO00/68197, WO00/69849, WO01/09120, WO01/14376, WO01/85714, WO1/85730, WO01/07409, WO01/02379, WO01/02379, WO01/23388, WO01/23389, WO01/44201, WO01/62737, WO01/62738, WO01/09120, WO02/20488, WO02/22592, WO02/48152, WO02/49648, WO02/094789, and compounds disclosed in Norman et al., J. Med. Chem., 43:4288-4312(2000); 10) reptins such as human recombinant reptin (PEG-OB, Hoffman La Roche), recombinant methionylreptin (Amgen); 11) reptin derivatives such as compounds disclosed in U.S. Pat. No. 5,552,524, U.S. Pat. No. 5,552,523, U.S. Pat. No. 5,552,522, U.S. Pat. No. 5,521,283, WO96/23513, WO96/23514, WO96/23515, WO96/23516, WO96/23517, 96/23518, WO96/23519, WO96/23520; 12) opioid antagonists such as narmefen (Revex™), 3-methoxynartorexon, naroxon, nartolexon, compounds disclosed in WO00/21509; 13) aurexin antagonists such as SB-334867A, and other compounds disclosed in WO01/96302, WO01/68609, WO02/51232, WO02/51838, WO03/023561; 14) bonbesin receptor subtype-3 agonists; 15) cholecystokinin A (CCK-A) agonists such as AR-R15849, GI-181771, JMV-180, A-71378, A-71623, SR-146131, and other compounds disclosed in U.S. Pat. No. 5,739,106; 16) CNTF (ciliary neurotrophic factors) such as GI-181771 (Glaxo-Smith Kline), SR146131 (Sanofi Synthelabo), butabindide, PD170,292, PD149164 (Pfizer); 17) CNTF derivatives such as axokine (Regeneron), and other compounds disclosed in WO94/09134, WO98/22128, WO99/43813; 18) growth hormone secretion receptor agonists such as NN703, hexarelin, MK-0677, SM-130686, CP-424,391, L-692,429, L-163,255, and compounds disclosed in U.S. Pat. No. 6,358,951, US Patent Application Nos. 2002/049196, 2002/022637, WO01/56592, WO02/32888; 19) serotonin receptor-2c agonists such as BVT933, DPCA37215, IK264, PNU22394, WAY161503, R-1065, YM348, and other compounds disclosed in U.S. Pat. No. 3,914,250, WO02/36596, WO02/48124, WO02/10169, WO01/66548, WO02/44152, WO02/51844, WO02/40456, WO02/40457; 20) melanochortin-3 receptor agonists; 21) melanocholtin-4 receptor agonists such as CHIR86036 (Chiron), ME-10142, ME-10145 (Melacure), and other compounds disclosed in WO99/64002, WO00/74679, WO01/991752, WO01/74844, WO01/70708, WO01/70337, WO01/91752, WO02/059095, WO02/059107, WO02/059108, WO02/059117, WO02/12166, WO02/11715, WO02/12178, WO02/15909, WO02/068387, WO02/068388, WO02/067869, WO03/007949, WO03/009847; 22) monoamine re-uptake inhibitors such as sibutramine (Meridia™/Reductil™) and its salts, and other derivatives disclosed in U.S. Pat. No. 4,746,680, U.S. Pat. No. 4,806,570, U.S. Pat. No. 5,436,272, US Patent Application No. 2002/0006964, WO01/27068, WO01/62341; 23) serotonin re-uptake inhibitors such as dexfenfluramine, fluoxetine, and other compounds disclosed in U.S. Pat. No. 6,365,633, WO01/27060, WO01/162341; 24) glucagon-like peptide-1 agonists; 25) topiramate (Topimax™); 26) phytopharm compound 57 (e.g., CP644,673); 27) acetyl CoA carboxylase-2 (ACC2) inhibitors; 28) β-adrenalin receptor-3 agonists such as AD9677/TAK677 (Dai-Nippon Pharmaceutical/Takeda Chemical), CL-316,243, SB418790, BRL-37344, L-796568, BMS-196085, BRL-35135A, CGP12177A, BTA-243, W427353, trecadrine, Zeneca D7114, SR59119A, and other compounds disclosed in U.S. Pat. No. 5,705,515, U.S. Pat. No. 5,451,677, WO01/74782, WO02/32898; 29) diacylglycerol acyltransferase-1 inhibitors; 30) diacylglycerol acyltransferase-2 inhibitors, 31) fatty acid synthesis inhibitors such as carulenin, C75; 32) phosphodiesterase inhibitors such as theofylline, pentoxifylline, zaprinast, sildenafil, amrinone, milrinone, cilostamide, rolipram, cilomilast; 32) thyroid hormone-β agonists such as KB-2611 (KaroBio BMS), and other compounds disclosed in WO02/15845, JP-A 2000-256190; 33) UCP (uncoupling protein)-1, 2, or 3 activators such as phytanic acid, 4-[(E)-2-(5,6,7,8-tetrahydro-5,5,8,8-tetramethyl-2-naphthalenyl-1-propenyl)benzoic acid (TTNPB), retinoic acid, and other compounds disclosed in WO99/00123; 34) acylestrogens such as oleoylestrone, and other compounds disclosed in del Mar-Grasa, M. et al., Obesity Research, 9:202-9 (2001); 35) glucocorticoid antagonists; 36) 11-β-hydroxysteroid dehydrogenase-1 inhibitors such as BVT3498, BVT2733, and other compounds disclosed in WO01/90091, WO01/90090, WO01/90092; 37) stearoyl-CoA desaturase-1 inhibitors; 38) dipeptidyl peptidase-IV inhibitors such as isoleucine thiazolidide, valine pyrrolidide, NVP-DPP728, AF237, P93/01, TSL225, TMC-2A/2B/2C, FE999011, P9310/K364, VIP0177, SDZ274-444, and other compounds disclosed in WO03/004498, WO03/004496, EP1258476, WO02/083128, WO02/062764, WO03/000250, WO03/002530, WO03/002531, WO03/002553, WO03/002539, WO03/000180, WO03/000181; 39) lipase inhibitors such as tetrahydroliptatin (Orlistat/Xenical™), Triton WR1339, RHC80267, lipstatin, teasaponin, diethylumbelliferyl phosphate, FL-386, WAY-121898, Bay-N-3176, valilactone, esteracin, ebelactone A, ebelactone B, RHC80267, and other compounds disclosed in WO01/77094, U.S. Pat. No. 4,598,089, U.S. Pat. No. 4,452,813, U.S. Pat. No. 5,512,565, U.S. Pat. No. 5,391,571, U.S. Pat. No. 5,602,151, U.S. Pat. No. 4,405,644, U.S. Pat. No. 4,189,438, U.S. Pat. No. 4,242,453; 39) fatty acid transporter inhibitors; 40) dicarboxylate transporter inhibitors; 41) glucose transporter inhibitors; 42) phosphate transporter inhibitors.

Those combination drugs are obtained by concurrent use of a compound of the invention with one, two or more of the above drugs for combined use. Furthermore, the combination drugs are useful for prevention or therapy of metabolic disorders, when combined with one, two or more drugs selected from the group consisting of diabetes-treating agents and hyperlipidemia-treating agents. Combinations containing, in particular, hypertension-treating agent and anti-obesity agent are useful for prevention, or therapy of metabolic disorders with synergistic effect, when diabetes-treating agent(s) and/or hyperlipidemia-treating agent(s) are added thereto.

BEST MODE FOR CARRYING OUT THE INVENTION

The invention is described in detail with reference to the following Examples, to which, however, the invention should not be limited. Unless otherwise specifically indicated, the reagents used in the Examples are commercial products. In H-NMR, tetramethylsilane was used as the standard substance.

PRODUCTION EXAMPLE 1-1

Ethyl 4-(6-chloropyridin-3-ylmethoxy)benzenecarboxylate

Potassium carbonate (1.3 g) and sodium iodide (93 mg) were added to a DMF solution (20 mL) of 2-chloro-5-chloromethylpyridine (1.0 g) and ethyl 4-hydroxybenzenecarboxylate (1.0 g), and stirred overnight at room temperature. Water was added to the reaction solution, and extracted with diethyl ether. The organic layer was dried with anhydrous magnesium sulfate, and the solvent was evaporated off under reduced pressure. The resulting residue was purified through silica gel column chromatography (hexane/ethyl acetate=9/1 to 3/2) to obtain the entitled compound (1.7 g).

PRODUCTION EXAMPLE 1-2

4-(6-Chloropyridin-3-ylmethoxy)benzenecarboxylic acid

Aqueous 5 N sodium hydroxide solution (11.8 mL) was added to an ethanol-THF mixed solution (3/2 by volume—the same shall apply hereunder: 10 mL) of the compound (1.7 g) obtained in Production Example 1-1, and stirred overnight at room temperature. 5 N hydrochloric acid (25 mL) was added to the reaction solution, and stirred at room temperature for 5 minutes. The organic solvent was evaporated off under reduced pressure, and the precipitated matter was taken out through filtration to obtain the entitled compound (1.5 g).

PRODUCTION EXAMPLE 2-1

Ethyl 5-chloropyridin-2-carboxylate

Palladium acetate (117 mg), 1,1'-bis(diphenylphosphino)ferrocene (577 mg) and triethylamine (1.4 mL) were added to an ethanol-DMF mixed solvent (1/1, 30 mL) of 2-bromo-5-chloropyridine (1.0 g), and stirred overnight in a carbon monoxide atmosphere (1 atmospheric pressure) at 50° C. Ethanol was evaporated off under reduced pressure from the reaction solution, water was added to the resulting residue, and extracted with hexane/ethyl acetate (2/3). The organic layer was dried with anhydrous magnesium sulfate, and the solvent was evaporated off under reduced pressure. The resulting residue was purified through silica gel column chromatography (hexane/ethyl acetate=9/1 to 4/1) to obtain the entitled compound (1.4 g).

PRODUCTION EXAMPLE 2-2

(5-Chloropyridin-2-yl)methanol

A THF solution (50 mL) of the compound (1.3 g) obtained in Production Example 2-1 was cooled to 0° C., and in a nitrogen atmosphere, a toluene solution (21.2 mL) of 1 M diisobutylaluminium hydride was dropwise added thereto at an inner temperature not higher than 5° C. This was stirred at 0° C. for 30 minutes, and then sodium borohydride (266 mg) and methanol (2 mL) were added to the reactor and stirred at room temperature for 30 minutes. Sodium sulfate 10-hydrate was added to the reaction solution, and stirred overnight at room temperature. The reaction solution was filtered through Celite, and the solvent was evaporated off from the filtrate under reduced pressure. The resulting residue was purified through silica gel column chromatography (hexane/ethyl acetate=3/2) to obtain the entitled compound (960 mg).

PRODUCTION EXAMPLE 2-3

Ethyl 4-(5-chloropyridin-2-ylmethoxy)benzenecarboxylate

Thionyl chloride (6.6 mL) was added to a dichloromethane solution (10 mL) of the compound (216 mg) obtained in Production Example 2-2, and stirred at room temperature for 2 hours. The solvent was evaporated off under reduced pressure from the reaction solution. The resulting residue and ethyl 4-hydroxybenzenecarboxylate (249 mg) were processed in the same manner as in Production Example 1-1 to obtain the entitled compound (334 mg).

PRODUCTION EXAMPLE 2-4

4-(5-Chloropyridin-2-ylmethoxy)benzenecarboxylic acid

The compound (334 mg) obtained in Production Example 2-3 was processed in the same manner as in Production Example 1-2 to obtain the entitled compound (286 mg).

PRODUCTION EXAMPLE 3-1

Ethyl 4-(pyridin-2-ylmethoxy)benzenecarboxylate

2-Chloromethylpyridine hydrochloride (500 mg) and ethyl 4-hydroxybenzenecarboxylate (506 mg) were processed in the same manner as in Production Example 1-1 to obtain the entitled compound (656 mg).

PRODUCTION EXAMPLE 3-2

4-(pyridin-2-ylmethoxy)benzenecarboxylic acid

The compound (656 mg) obtained in Production Example 3-1 was processed in the same manner as in Production Example 1-2 to obtain the entitled compound (580 mg).

PRODUCTION EXAMPLE 3-3

Methyl 5-(pyridin-2-ylmethoxy)-1H-indole-2-carboxylate

2-Chloromethylpyridine hydrochloride (515 mg) and methyl 5-hydroxy-1H-indole-2-carboxylate (600 mg) were processed in the same manner as in Production Example 1-1 to obtain the entitled compound (160 mg).

PRODUCTION EXAMPLE 3-4

5-(Pyridin-2-ylmethoxy)-1H-indole-2-carboxylic acid

The compound (220 mg) obtained in Production Example 3-3 was processed in the same manner as in Production Example 1-2 to obtain the entitled compound (210 mg).

PRODUCTION EXAMPLE 4-1

Ethyl 5-hydroxypyridine-2-carboxylate

Palladium acetate (267 mg), 1,1'-bis(diphenylphosphino)ferrocene (1.3 g) and triethylamine (3.2 mL) were added to an ethanol-DMF mixed solvent (1/1, 20 mL) of 6-chloropyridin-3-ol (1.5 g), and stirred overnight in a carbon monoxide atmosphere (1 atmospheric pressure) at 50° C. Ethanol was evaporated off under reduced pressure from the reaction solution, water was added to the resulting residue, and extracted with chloroform/methanol (10/1). The organic layer was dried with anhydrous magnesium sulfate, and the solvent was evaporated off under reduced pressure. The resulting residue was purified through silica gel column chromatography (hexane/ethyl acetate=2/3) to obtain the entitled compound (500 mg).

PRODUCTION EXAMPLE 4-2

Ethyl 5-benzyloxypyridine-2-carboxylate

Potassium carbonate (249 mg) and benzyl bromide (107 µL) were added to a DMF solution (4 mL) of the compound (100 mg) obtained in Production Example 4-1, and stirred overnight at room temperature. Water was added to the reaction solution, and extracted with ethyl acetate. The organic layer was dried with anhydrous magnesium sulfate, and the solvent was evaporated off under reduced pressure. The resulting residue was purified through silica gel column chromatography (hexane/ethyl acetate=4/1 to 2/3) to obtain the entitled compound (110 mg).

PRODUCTION EXAMPLE 4-3

5-Benzyloxypyridine-2-carboxylic acid

The entitled compound (46 mg) was obtained in the same manner as in Production Example 1-2, for which, however, the compound (110 mg) obtained in Production Example 4-2 and ethanol (4 mL) as a solvent were used.

PRODUCTION EXAMPLE 5-1

2-Bromo-5-fluoropyridine

The entitled compound (2.2 g) was obtained according to the method described in WO03/05088, but using 2-amino-5-fluoropyridine (1.5 g).

PRODUCTION EXAMPLE 5-2

Ethyl 5-fluoropyridine-2-carboxylate

The compound (2.2 g) obtained in Production Example 5-1 was processed in the same manner as in Production Example 2-1 to obtain the entitled compound (1.2 g).

PRODUCTION EXAMPLE 5-3

(5-Fluoropyridin-2-yl)methanol

A THF solution (50 mL) of the compound (1.1 g) obtained in Production Example 5-2 was cooled to 0° C., and in a nitrogen atmosphere, a toluene solution (19.5 mL) of 1 M diisobutylaluminium hydride was dropwise added thereto at an inner temperature not higher than 5° C. This was stirred at 0° C. for 30 minutes, and then sodium borohydride (246 mg) and methanol (2 mL) were added to the reaction solution and stirred at room temperature for 30 minutes. Sodium sulfate 10-hydrate was added to the reaction solution, and stirred overnight at room temperature. The reaction solution was filtered through Celite, and the solvent was evaporated off from the filtrate under reduced pressure. The resulting residue was purified through silica gel column chromatography (hexane/ethyl acetate=9/1 to 3/2) to obtain the entitled compound (800 mg).

PRODUCTION EXAMPLE 5-4

Ethyl 4-(5-fluoropyridin-2-ylmethoxy)benzenecarboxylate

The compound (300 mg) obtained in Production Example 5-3 and ethyl 4-hydroxybenzenecarboxylate (392 mg) were processed in the same manner as in Production Example 2-3 to obtain the entitled compound (274 mg).

PRODUCTION EXAMPLE 5-5

4-(5-Fluoropyridin-2-ylmethoxy)benzenecarboxylic acid

The compound (274 mg) obtained in Production Example 5-4 was processed in the same manner as in Production Example 1-2 to obtain the entitled compound (240 mg).

PRODUCTION EXAMPLE 6-1

Methyl 3-fluoropyridin-2-carboxylate

A hexane solution (3 mL) of 2 M trimethylsilyldiazomethane was added to a benzene/methanol mixed solvent (1/1, 12 mL) of 3-fluoropyridine-2-carboxylic acid (250 mg), and stirred at room temperature for 30 minutes. The solvent was evaporated off under reduced pressure from the reaction solution, and the resulting residue was purified through silica gel column chromatography (chloroform/methanol=40/1) to obtain the entitled compound (238 mg).

PRODUCTION EXAMPLE 6-2

(3-Fluoropyridin-2-yl)methanol

The compound (238 mg) obtained in Production Example 6-1 was processed in the same manner as in Production Example 2-2 to obtain the entitled compound (142 mg).

PRODUCTION EXAMPLE 6-3

Ethyl 4-(3-fluoropyridin-2-ylmethoxy)benzenecarboxylate

The compound (142 mg) obtained in Production Example 6-2 and ethyl 4-hydroxybenzenecarboxylate were processed in the same manner as in Production Example 2-3 to obtain the entitled compound (247 mg).

PRODUCTION EXAMPLE 6-4

4-(3-Fluoropyridin-2-ylmethoxy)benzenecarboxylic acid

The compound (247 mg) obtained in Production Example 6-3 was processed in the same manner as in Production Example 1-2 to obtain the entitled compound (215 mg).

PRODUCTION EXAMPLE 7-1

Methyl 6-fluoropyridine-2-carboxylate

6-Fluoropyridine-2-carboxylic acid (1.6 g) was processed in the same manner as in Production Example 6-1 to obtain the entitled compound (1.5 g).

PRODUCTION EXAMPLE 7-2

(6-Fluoropyridin-2-yl)methanol

The compound (1.5 g) obtained in Production Example 7-1 was processed in the same manner as in Production Example 2-2 to obtain the entitled compound (1.1 g).

PRODUCTION EXAMPLE 7-3

2-Chloromethyl-6-fluoropyridine

Thionyl chloride (25 mL) was added to a dichloromethane solution (80 mL) of the compound (1.1 g) obtained in Production Example 7-2, and stirred at room temperature for 2 hours. The solvent was evaporated off under reduced pressure, ethyl acetate was added to the resulting residue, and the organic layer was washed with aqueous saturated sodium hydrogencarbonate solution. The organic layer was dried with anhydrous magnesium sulfate, and the solvent was evaporated off under reduced pressure to obtain the entitled compound (990 mg).

PRODUCTION EXAMPLE 7-4

Ethyl 4-(6-fluoropyridin-2-ylmethoxy)benzenecarboxylate

The compound (806 mg) obtained in Production Example 7-3 was processed in the same manner as in Production Example 1-1 to obtain the entitled compound (1.4 g).

PRODUCTION EXAMPLE 7-5

4-(6-Fluoropyridin-2-ylmethoxy)benzenecarboxylic acid

The compound (1.3 g) obtained in Production Example 7-4 was processed in the same manner as in Production Example 1-2 to obtain the entitled compound (1.2 g).

PRODUCTION EXAMPLE 8-1

Methyl 3-fluoro-4-hydroxybenzenecarboxylate

A commercial product, 3-fluoro-4-hydroxybenzoic acid hydrate (1.1 g) was dissolved in methanol (11 mL), and in an ice bath, thionyl chloride (0.77 mL) was added thereto, and heated under reflux for 2 hours. After the reaction, the reaction liquid was entirely concentrated to obtain the entitled compound (1.1 g).

PRODUCTION EXAMPLE 8-2

Methyl 3-fluoro-4-(pyridin-2-ylmethoxy)benzenecarboxylate

The compound (500 mg) obtained in Production Example 8-1 and 2-hydroxymethylpyridine (270 mg) were processed in the same manner as in Production Example 2-3 to obtain the entitled compound (625 mg).

PRODUCTION EXAMPLE 8-3

3-Fluoro-4-(pyridin-2-ylmethoxy)benzenecarboxylic acid

The compound (240 mg) obtained in Production Example 8-2 was processed in the same manner as in Production Example 1-2 to obtain the entitled compound (205 mg).

PRODUCTION EXAMPLE 9-1

2-Fluoro-4-(pyridin-2-ylmethoxy)benzonitrile

2-Fluoro-4-hydroxybenzonitrile (1.0 g) and 2-chloromethylpyridine hydrochloride (1.2 g) were processed in the same manner as in Production Example 1-1 to obtain the entitled compound (1.2 g).

PRODUCTION EXAMPLE 9-2

2-Fluoro-4-(pyridin-2-ylmethoxy)benzenecarboxylic acid

The compound (200 mg) obtained in Production Example 9-1 was heated under reflux in aqueous 5 N sodium hydroxide solution (1.8 mL) for 8 hours. The reaction solution was cooled to room temperature, and aqueous 5 N hydrochloric acid solution (5 mL) was added thereto. The resulting precipitated matter was taken out through filtration to obtain the entitled compound (195 mg).

PRODUCTION EXAMPLE T-1

Methyl 3-fluoro-4-[(5-fluoropyridin-2-yl)methoxy]benzenecarboxylate

The compound (500 mg) obtained in Production Example 8-1 and the compound (267 mg) obtained in Production Example 5-3 were processed in the same manner as in Production Example 2-3 to obtain the entitled compound (624 mg).

PRODUCTION EXAMPLE T-2

3-Fluoro-4-[(5-fluoropyridin-2-yl)methoxy]benzenecarboxylic acid

The compound (165 mg) obtained in Production Example T-1 was processed in the same manner as in Production Example 1-2 to obtain the entitled compound (141 mg).

PRODUCTION EXAMPLE 10-1

Ethyl 5-(5-chloropyridin-2-ylmethoxy)pyridin-2-carboxylate

The compound (960 mg) obtained in Production Example 4-1 and the compound (165 mg) obtained in Production Example 2-2 were processed in the same manner as in Production Example 2-3 to obtain the entitled compound (172 mg).

PRODUCTION EXAMPLE 10-2

5-(5-Chloropyridin-2-ylmethoxy)pyridin-2-carboxylic acid

The compound (172 mg) obtained in Production Example 10-1 was processed in the same manner as in Production Example 1-2 to obtain the entitled compound (122 mg).

PRODUCTION EXAMPLE 11-1

1-(Pyridin-2-yl)ethanol

A methanol solution (100 mL) of 1-pyridin-2-ylethanone (10.0 g) was cooled to 0° C., sodium borohydride (6.2 g) was added thereto and stirred at that temperature for 4 hours. Then water was added to the reaction solution, and the organic solvent was evaporated off under reduced pressure. The resulting residue was extracted with ethyl acetate. The organic layer was dried with anhydrous magnesium sulfate, and the solvent was evaporated off under reduced pressure. The resulting residue was purified through silica gel column chromatography (hexane/ethyl acetate=4/1 to 3/2) to obtain the entitled compound (9.0 g).

PRODUCTION EXAMPLE 11-2

Ethyl 4-(1-pyridin-2-ylethoxy)benzenecarboxylate

Triphenyl phosphine (5.1 g) and a THF solution (5 mL) of diisopropyl azodicarboxylate (3.9 mL) were added in that order a THF solution (40 mL) of the compound (2.0 g) obtained in Production Example 11-1 and ethyl 4-hydroxybenzenecarboxylate (2.7 g), and stirred at room temperature for 3 hours. The reaction solution was concentrated under reduced pressure, and the resulting residue was purified through silica gel column chromatography (hexane/ethyl acetate=9/1 to 3/2) to obtain the entitled compound (4.4 g).

PRODUCTION EXAMPLE 11-3

4-(1-Pyridin-2-ylethoxy)benzenecarboxylic acid

The compound (4.4 g) obtained in Production Example 11-2 was processed in the same manner as in Production Example 1-2 to obtain the entitled compound (3.8 g).

PRODUCTION EXAMPLE 12-1

Ethyl 5-methyl-[1,3,4]thiadiazole-2-carboxylate

Triethylamine (7.5 mL) and ethyl chloroglyoxalate (3.6 mL) were added to a chloroform suspension (35 mL) of acetohydrazide (2.0 g), and the resulting suspension was stirred overnight at room temperature. After the reaction, the reaction liquid was entirely concentrated, the resulting residue was suspended in toluene (135 mL), and a Lawesson's reagent (7.6 g) was added thereto. After heated under reflux for 3 hours, the reaction liquid was entirely concentrated, and the resulting residue was purified through silica gel column chromatography (hexane/ethyl acetate=3/1) to obtain the entitled compound (110 mg).

PRODUCTION EXAMPLE 12-2

(5-Methyl-[1,3,4]thiadiazol-2-yl)methanol

The compound (31 mg) obtained in Production Example 12-1 was processed in the same manner as in Production Example 2-2 to obtain the entitled compound (15 mg).

PRODUCTION EXAMPLE 12-3

Ethyl 4-(5-methyl-[1,3,4]thiadiazol-2-ylmethoxy)benzenecarboxylate

The compound (14 mg) obtained in Production Example 12-2 and ethyl 4-hydroxybenzenecarboxylate (22 mg) were processed in the same manner as in Production Example 2-3 to obtain the entitled compound (25 mg).

PRODUCTION EXAMPLE 12-4

4-(5-Methyl-[1,3,4]thiadiazol-2-ylmethoxy)benzenecarboxylic acid

The compound (25 mg) obtained in Production Example 12-3 was processed in the same manner as in Production Example 1-2 to obtain the entitled compound (17 mg).

PRODUCTION EXAMPLE 13-1

Methyl 4-(pyridin-2-yloxymethyl)benzenecarboxylate

Triphenyl phosphine (614 mg) and a THF solution (1 mL) of diethyl azodicarboxylate (408 mg) were added in that order to a THF solution (20 mL) of 2-hydroxypyridine (149 mg) and methyl 4-hydroxymethylbenzenecarboxylate (260 mg), and stirred overnight at room temperature. The reaction solution was concentrated under reduced pressure, and the resulting residue was purified through silica gel column chromatography (hexane/ethyl acetate=9/1 to 2/3 to ethyl acetate alone) to obtain the entitled compound (85 mg).

PRODUCTION EXAMPLE 13-2

4-(Pyridin-2-yloxymethyl)benzenecarboxylic acid

The compound (85 mg) obtained in Production Example 13-1 and methanol as a solvent were processed in the same manner as in Production Example 1-2 to obtain the entitled compound (75 mg).

PRODUCTION EXAMPLE 14-1

Methyl 4-(5-fluoropyrimidin-2-yloxymethyl)benzenecarboxylate

A mixture of 4-hydroxymethylbenzenecarboxylic acid (720 mg), 60% sodium hydride (190 mg) and THF (17 mL) was stirred at room temperature for about 30 minutes, and then a THF solution (5 mL) of 2-chloro-5-fluoropyrimidine (860 mg) produced according to JP-A 09-165379 was dropwise added thereto, and stirred for about 2 hours. After the reaction, aqueous saturated ammonium chloride solution was added to the reaction solution, and extracted with ethyl acetate. The organic layer was dried with anhydrous magnesium sulfate, and the solvent was evaporated off under reduced pressure. The resulting residue was purified through silica gel column chromatography (hexane/ethyl acetate=85/15) to obtain the entitled compound (465 mg).

PRODUCTION EXAMPLE 14-2

4-(5-Fluoropyrimidin-2-yloxymethyl)benzenecarboxylic acid

The compound (205 mg) obtained in Production Example 14-1 was processed in the same manner as in Production Example 1-2 to obtain the entitled compound (170 mg).

PRODUCTION EXAMPLE 15-1

Methyl 4-bromomethyl-3-fluorobenzenecarboxylate

3-Fluoro-4-methylbenzenecarboxylic acid (1.0 g) was dissolved in methanol (33 mL), and thionyl chloride (0.72 mL) was added thereto and heated under reflux for 1 hour. After the reaction, the reaction solution was entirely concentrated, the resulting residue (500 mg) was dissolved in carbon tetrachloride (3 mL), and N-bromosuccinimide (hereafter abbreviated as "NBS") (510 mg) and 2,2'-azobis(isobutyronitrile) (hereafter abbreviated as "AIBN") (50 mg) were added in that order to it, and heated under reflux for 4 hours. After the reaction, the reaction solution was entirely concentrated, and the resulting residue was purified through silica gel column chromatography (hexane/ethyl acetate=95/5) to obtain the entitled compound (405 mg).

PRODUCTION EXAMPLE 15-2

Methyl 3-fluoro-4-(pyridin-2-yloxymethyl)benzenecarboxylate

The compound (1.1 g) obtained in Production Example 15-1, 2-hydroxypyridine (0.43 g) and potassium carbonate (1.25 g) were stirred in DMF (15 mL) at 80° C. for 4.5 hours. The reaction was stopped with aqueous sodium hydrogencarbonate solution, and this was extracted with ethyl acetate. The organic layer was dried with anhydrous magnesium sulfate, and the solvent was evaporated off under reduced pressure. The resulting residue was purified through reversed-phase HPLC to obtain the entitled compound (31 mg).

PRODUCTION EXAMPLE 15-3

3-Fluoro-4-(pyridin-2-yloxymethyl)benzenecarboxylic acid

The compound (31 mg) obtained in Production Example 15-2 was processed in the same manner as in Production Example 1-2 to obtain the entitled compound (26 mg).

PRODUCTION EXAMPLE 16-1

Methyl 4-[(E)-2-(6-methylpyridin-2-yl)vinyl]benzenecarboxylate

An acetic anhydride solution (100 mL) of 2,6-lutidine (65 g) and methyl 4-formylbenzenecarboxylate (20 g) was stirred overnight at 180° C. The reaction solution was poured into water with ice, and aqueous 5 N sodium hydroxide solution was added thereto until it became alkaline. The resulting mixture was extracted with ethyl acetate, and the organic layer was dried with anhydrous magnesium sulfate. The solvent was evaporated off, and the resulting residue was purified through silica gel column chromatography (hexane/ethyl acetate=9/1 to 4/1) to obtain the entitled compound (20.1 g).

PRODUCTION EXAMPLE 16-2

4-[(E)-2-(6-methylpyridin-2-yl)vinyl]benzenecarboxylic acid

The compound (2.0 g) obtained in Production Example 16-1 and a methanol/THF mixed solvent were processed in the same manner as in Production Example 1-2 to obtain the entitled compound.

PRODUCTION EXAMPLE 17-1

Methyl 4-((E)-2-pyridin-2-ylvinyl)benzenecarboxylate

2-Methylpyridine (5.7 g) and methyl 4-formylbenzenecarboxylate (10 g) were processed in the same manner as in Production Example 16-1 to obtain the entitled compound (5.4 g).

PRODUCTION EXAMPLE 17-2

4-((E)-2-pyridin-2-ylvinyl)benzenecarboxylic acid

The compound (1.0 g) obtained in Production Example 17-1 and a methanol/THF mixed solvent were processed in the same manner as in Production Example 1-2 to obtain the entitled compound (940 mg).

PRODUCTION EXAMPLE 18-1

Methyl 4-(diethoxyphosphorylmethyl)-3-fluorobenzenecarboxylate

A mixture of methyl 4-bromomethyl-3-fluorobenzenecarboxylate (240 mg) and triethyl phosphite (0.32 mL) was heated at 145° C. for 2 hours. The reaction solution was purified through silica gel column chromatography (ethyl acetate/methanol=9/1) to obtain the entitled compound (300 mg).

PRODUCTION EXAMPLE 18-2

Methyl 3-fluoro-4-((E)-2-pyridin-2-ylvinyl)benzenecarboxylate

A mixture of the compound (240 mg) obtained in Production Example 18-1, 60% sodium hydride (56 mg) and THF (6 mL) was stirred for 1 hour, and then a THF solution (1.2 mL) of pyridine-2-carbaldehyde (125 mg) was dropwise added thereto. The reaction liquid was stirred at room temperature for 3.5 hours, water was added thereto, and extracted with ethyl acetate. The organic layer was dried with anhydrous magnesium sulfate, and the solvent was evaporated off under reduced pressure. The resulting residue was purified through silica gel column chromatography (hexane/ethyl acetate=1/1) to obtain the entitled compound (185 mg).

PRODUCTION EXAMPLE 18-3

3-Fluoro-4-((E)-2-pyridin-2-ylvinyl)benzenecarboxylate

The compound (140 mg) obtained in Production Example 18-2 was processed in the same manner as in Production Example 1-2 to obtain the entitled compound (110 mg).

PRODUCTION EXAMPLE T-3

6-Chloronicotinaldehyde

At −78° C., a hexane solution (11.5 mL) of 1.59 M n-butyllithium was dropwise added to a diethyl ether solution (140 mL) of 5-bromo-2-chloropyridine (2.9 g). This was stirred at that temperature, then a diethyl ether solution (3 mL) of DMF (1.8 mL) was added thereto and stirred at that temperature for 3.5 hours. Aqueous saturated sodium hydrogencarbonate solution was added to the reaction liquid, and extracted with ethyl acetate. The organic layer was washed with saturated saline water, dried with anhydrous magnesium sulfate, and the solvent was evaporated off under reduced pressure. The resulting residue was purified through silica gel column chromatography (ethyl acetate/hexane=1/9) to obtain the entitled compound (1.4 g).

PRODUCTION EXAMPLE T-4

4-[(E)-2-(6-chloropyridin-3-yl)vinyl]benzenecarboxylic acid

60% sodium hydride (184 mg) was added to a DMF solution (8.4 mL) of 4-(diethoxyphosphorylmethyl)benzenecarboxylic acid (636 mg) produced according to JP-A 11-60537 at 0° C., and stirred for 1 hour, and then a DMF solution (10 mL) of the compound (296 mg) obtained in Production Example T-3 was added thereto at 0° C. and stirred for 5 hours. Water was added to the reaction liquid, its pH was controlled to be 2 with 4 N hydrochloric acid, and the precipitated matter was taken out through filtration to obtain the entitled compound (464 mg) as a yellow solid.

PRODUCTION EXAMPLE 19-1

2-Fluoro-6-vinylpyridine

Potassium vinyltrifluoroborate (2.28 g), triethylamine (2.38 mL) and [1,1'-bis(diphenylphosphino)ferrocene]palladium(II) dichloromethane complex (928 mg) were added in that order to an n-propanol solution (12 mL) of 2-bromo-6-fluoropyridine (2.0 g), and stirred at 100° C. for 11 hours, and then at room temperature for 2 days. Saturated sodium hydrogencarbonate solution was added to the reaction liquid, and extracted with ethyl acetate. The organic layer was washed with saturated saline water, dried, concentrated under reduced pressure, and the residue was purified through silica gel column chromatography (hexane/ethyl acetate=9/1) to obtain the entitled compound (500 mg).

PRODUCTION EXAMPLE 19-2

Ethyl 4-[(E)-2-(6-fluoropyridin-2-yl)vinyl]benzenecarboxylate

Ethyl 4-iodobenzenecarboxylate (1.12 g), triphenyl phosphine (213 mg) and palladium acetate (91 mg) were added in that order to a triethylamine solution (15 mL) of the compound (500 mg) obtained in Production Example 19-1, and stirred at 100° C. for 16 hours. The reaction liquid was left cooled, water was added thereto, and extracted with ethyl acetate. The organic layer was washed with saturated saline water, dried, concentrated under reduced pressure, and the resulting residue was purified through silica gel column chromatography (hexane/ethyl acetate =9/1) to obtain the entitled compound (850 mg).

PRODUCTION EXAMPLE 19-3

4-[(E)-2-(6-fluoropyridin-2-yl)vinyl]benzenecarboxylic acid

Aqueous 4 N sodium hydroxide solution (1.1 mL) was added to a mixed methanol (8.0 mL)/tetrahydrofuran (4.0 mL) solution of the compound (400 mg) obtained in Production Example 19-2, and stirred at room temperature for 2 hours. The pH of the mixture solution was made about 3 with 6 N hydrochloric acid at 0° C., and the mixture solution was then extracted with ethyl acetate. The organic layer was washed with saturated saline water, dried and concentrated under reduced pressure to obtain the entitled compound (362 mg).

PRODUCTION EXAMPLE J-1

4-[(E)-2-(5-fluoropyridin-2-yl)vinyl]benzenecarboxylic acid (1) Ethyl 4-[(E)-2-(5-fluoropyridin-2-yl)vinyl]benzenecarboxylate was obtained in the same manner as in Production Example 19-2, for which, however, 5-fluoro-2-vinylpyridine (200 mg) was used.

(2) The compound obtained in the above was processed in the same manner as in Production Example 19-3 to obtain the entitled compound (215 mg) as a colorless solid.

PRODUCTION EXAMPLE 20-1

4-[(E)-2-(1,3-thiazol-2-yl)vinyl]benzenecarboxylic acid

A mixture of 4-(diethoxyphosphorylmethyl)benzenecarboxylic acid (440 mg) produced according to JP-A 11-60537, potassium tert-butoxide (340 mg) and THF (5.5 mL) was stirred at room temperature for about 1.5 hours, and then a THF solution (1.0 mL) of 2-formylthiazole (200 mg) was dropwise added thereto. After heated overnight under reflux, water was added to the reaction solution, and extracted with ethyl acetate. The organic layer was dried with anhydrous magnesium sulfate, and the solvent was evaporated off under reduced pressure. The resulting residue was purified through silica gel column chromatography (ethyl acetate/methanol=9/1), and the resulting purified product was further purified through reversed-phase HPLC to obtain the entitled compound (7 mg).

PRODUCTION EXAMPLE 21-1

Methyl 4-(2-oxo-2-pyridin-2-ylethyl)benzenecarboxylate (1) Diphenyl phosphite (17.5 g) was added to a 2-propanol solution (100 mL) of pyridine-2-carbaldehyde (5.0 g) and aniline (5.2 g), and stirred at room temperature for 1 hour. The reaction liquid was concentrated under reduced pressure, and diluted with isopropyl ether (100 mL). The precipitated solid was taken out through filtration, and washed with isopropyl ether to obtain a white solid (19.6 g).

(2) Cesium carbonate (8.5 g) was added to a mixed THF (40 mL)/2-propanol (10 mL) solution of the solid (8.3 g) obtained in the above and methyl 4-formylbenzenecarboxylate (3.5 g), and stirred for one day at room temperature. Next, aqueous 1 N hydrochloric acid solution (50 mL) was added to the reaction liquid, and stirred at room temperature for 1 hour. The reaction solution was neutralized with aqueous saturated sodium hydrogencarbonate solution, and then extracted with ethyl acetate. The organic layer was washed with water and saturated saline water, then dried with anhydrous sodium sulfate. The organic layer was concentrated under reduced pressure, and the residue was purified through silica gel column chromatography (hexane/ethyl acetate=10/1) to obtain the entitled compound (3.5 g)

ESI-MS Found: m/z 256 [M+H]$^+$.

PRODUCTION EXAMPLE 21-2

Methyl 4-(2,2-difluoro-2-pyridin-2-ylethyl)benzenecarboxylate, methyl 4-((Z)-2-fluoro-2-pyridin-2-ylvinyl)benzenecarboxylate, or methyl 4-((E)-1,2-difluoro-2-pyridin-2-ylvinyl)benzenecarboxylate The compound (360 mg) obtained in Production Example 21-1 was added to bis(2-methoxyethyl)aminosulfate trifluoride (5 mL), and stirred for one day at 80° C. Aqueous saturated sodium hydrogencarbonate solution was added to the reaction liquid, and extracted with ethyl acetate. The organic layer was washed with water and saturated saline water in that order, and dried with anhydrous sodium sulfate. The organic layer was concentrated under reduced pressure, and the residue was purified through silica gel column chromatography (hexane/ethyl acetate=10/1) to obtain methyl 4-(2,2-difluoro-2-pyridin-2-ylethyl)benzenecarboxylate (123 mg), methyl 4-((Z)-2-fluoro-2-pyridin-2-ylvinyl)benzenecarboxylate (10 mg), and methyl 4-((E)-1,2-difluoro-2-pyridin-2-ylvinyl)benzenecarboxylate (90 mg) in that order.

PRODUCTION EXAMPLE K-1

Methyl 4-[(diethoxyphosphoryl)(hydroxy)methyl]benzenecarboxylate

Diethyl phosphite (16 mL) was added to methyl 4-formylbenzenecarboxylate (10.2 g) and potassium fluoride (18.0 g), and stirred at room temperature for 30 minutes. The reaction liquid was diluted with chloroform (200 mL) added thereto, and filtrated through Celite. The solvent was evaporated off under reduced pressure from the filtrate, and the resulting solid was washed with diethyl ether to obtain the entitled compound (14.1 g) as a colorless solid.

PRODUCTION EXAMPLE K-2

Methyl 4-[(diethoxyphosphoryl)(fluoro)methyl]benzenecarboxylate

Diethylaminosulfur trifluoride (hereafter abbreviated as "DAST") (2.4 g) was added to a chloroform solution (30 mL) of the compound (2.5 g) obtained in Production Example K-1, and stirred at 0° C. for 4 hours. Aqueous saturated sodium hydrogencarbonate solution was added to the reaction liquid, and extracted with ethyl acetate. The organic layer was washed with water and saturated saline water, then dried with anhydrous sodium sulfate. The solvent was evaporated off under reduced pressure, and the resulting residue was purified through silica gel column chromatography (hexane/ethyl acetate=2/1) to obtain the entitled compound (2.4 g) as a brown liquid.

PRODUCTION EXAMPLE K-3

Methyl 4-[(Z)-1-fluoro-2-pyridin-2-ylvinyl]benzenecarboxylate, and methyl 4-[(E)-1-fluoro-2-pyridin-2-ylvinyl]benzenecarboxylate Cesium carbonate (2.1 g) was added to a THF/isopropanol mixed solvent (4/1, 10 mL) of the compound (1.5 g) obtained in Production Example K-2 and 2-pyridinecarbaldehyde (530 mg), and stirred overnight at room temperature. Water was added to the reaction liquid, and extracted with ethyl acetate.

The organic layer was washed with water and saturated saline water, and dried with anhydrous sodium sulfate. The solvent was evaporated off under reduced pressure, and the resulting residue was purified through silica gel column chromatography (hexane/ethyl acetate=5/1) to obtain methyl 4-[(Z)-1-fluoro-2-pyridin-2-ylvinyl]benzenecarboxylate (495 mg) and methyl 4-[(E)-1-fluoro-2-pyridin-2-ylvinyl]benzenecarboxylate (684 mg) as a colorless solid and a colorless liquid, respectively.

PRODUCTION EXAMPLE K-4

4-[(Z)-1-fluoro-2-pyridin-2-ylvinyl]benzenecarboxylic acid

Methyl 4-[(Z)-1-fluoro-2-pyridin-2-ylvinyl]benzenecarboxylate (490 mg) obtained in Production Example K-3 was processed in the same manner as in Production Example 1-2 to obtain the entitled compound (455 mg) as a colorless solid.

PRODUCTION EXAMPLE K-5

4-[(E)-1-fluoro-2-pyridin-2-ylvinyl]benzenecarboxylic acid

Methyl 4-[(E)-1-fluoro-2-pyridin-2-ylvinyl]benzenecarboxylate (680 mg) obtained in Production Example K-3 was processed in the same manner as in Production Example 1-2 to obtain the entitled compound (568 mg) as a colorless solid.

PRODUCTION EXAMPLE T-5

3-Fluoro-4-(2-pyridin-2-ylethyl)benzenecarboxylic acid (1) The compound (45 mg) obtained in Production Example 18-2 was dissolved in methanol (2 mL), and 10% palladium-carbon (50 mg) was added thereto, and stirred in a hydrogen atmosphere at room temperature for 30 minutes. After the reaction, the palladium was removed through Celite filtration, and the solvent was evaporated off from the filtrate under reduced pressure to obtain methyl 3-fluoro-4-(2-pyridin-2-ylethyl)benzenecarboxylate (40 mg).

(2) The compound obtained in the above was processed in the same manner as in Production Example 1-2 to obtain the entitled compound (17 mg).

PRODUCTION EXAMPLE 22-1

3-Phenylpropionic acid hydrazide

Methyl trans-cinnamate (1.0 g) and hydrazine (1.2 mL) were heated in methanol (25 mL) at 60° C. for 20 hours. The reaction solution was concentrated under reduced pressure, and the resulting residue was purified through silica gel column chromatography (ethyl acetate/methanol=95/5) to obtain a mixture of the entitled compound and an olefin-unreduced compound (2/1) (499 mg).

PRODUCTION EXAMPLE 22-2

Ethyl oxo-[N'-(3-phenylpropionyl)hydrazino]acetate

The 3-phenylpropionic acid hydrazide mixture (499 mg) obtained in Production Example 22-1 was dissolved in chloroform (30 mL), and triethylamine (0.86 mL) and ethyl chloroglyoxalate (0.4 mL) were added thereto, and stirred at room temperature for 5 hours. After the reaction, the reaction liquid was entirely concentrated, and the resulting residue was purified through silica gel column chromatography (chloroform/methanol=94/6) to obtain the entitled compound (760 mg).

PRODUCTION EXAMPLE 22-3

Ethyl 5-phenethyl-[1,3,4]thiadiazole-2-carboxylate

The compound (140 mg) obtained in Production Example 22-2 was suspended in toluene (3 mL), and a Lawesson's reagent (150 mg) was added thereto and heated under reflux for 1 hour. The reaction liquid was entirely concentrated, and the resulting residue was purified through silica gel column chromatography (hexane/ethyl acetate=7/3) to obtain the entitled compound (97 mg).

PRODUCTION EXAMPLE 22-4

5-Phenethyl-[1,3,4]thiadiazole-2-carboxylic acid

The entitled compound was obtained in the same manner as in Production Example 1-2, for which, however, the compound obtained in Production Example 22-3 and a methanol/acetone mixed solvent were used.

PRODUCTION EXAMPLE 23-1

4-(2-Oxo-2-pyridin-2-ylethyl)benzenecarboxylic acid

A THF solution (50 mL) of diisopropylamine (12.6 mL) was cooled to 0° C., and a hexane (33 mL) solution of 2.6 M n-butyllithium was added thereto and stirred at that temperature for 10 minutes. Then this was cooled to −78° C., and a THF solution (15 mL) of 4-methylbenzenecarboxylic acid (2.3 g) was dropwise added thereto. The reaction liquid was stirred at −40° C. for 2.5 hours, and then a THF solution (4 mL) of methyl picolinate (2.0 g) was dropwise added thereto. The reaction solution was heated up to room temperature, and stirred for one day. Next, water was added to the reaction liquid, then controlled to have a pH of 4 with aqueous hydrochloric acid solution added thereto, and then extracted with ethyl acetate. The organic layer was dried with anhydrous sodium sulfate, concentrated under reduced pressure, and the resulting residue was purified through silica gel column chromatography (hexane/ethyl acetate=4/1) to obtain the entitled compound (400 mg).

ESI-MS Found: m/z 242 [M+H]$^+$

PRODUCTION EXAMPLE K-6

Methyl 4-(1-hydroxy-2-pyridin-2-ylethyl)benzenecarboxylate

With cooling with ice, a hexane solution (48 mL) of 2.6 N n-butyllithium was added to a THF solution (300 mL) of diisopropylamine (18 mL), stirred at 0° C. for 5 minutes, and then cooled to −78° C. Next, 2-picoline (10 g) was dropwise added thereto, and stirred at that temperature for 30 minutes. THF solution (100 mL) of methyl 4-formylbenzenecarboxylate (17.6 g) was added thereto, and stirred at −78° C. for 30 minutes and then at room temperature for 4 hours. Aqueous saturated ammonium chloride solution was added to the reaction liquid, and extracted with ethyl acetate. The organic layer was washed with aqueous saturated ammonium chloride solution and saturated saline water, and dried with anhydrous sodium sulfate. The solvent was evaporated off under reduced pressure, and the resulting residue was purified through silica gel column chromatography (hexane/ethyl acetate=2/1) to obtain the entitled compound (1.5 g) as a colorless solid.

PRODUCTION EXAMPLE K-7

4-(1-hydroxy-2-pyridin-2-ylethyl)benzenecarboxylic acid

The compound (400 mg) obtained in Production Example K-6 was processed in the same manner as in Production Example 1-2 to obtain the entitled compound (270 mg) as a brown solid.

PRODUCTION EXAMPLE 24-1

4-(pyridin-2-ylmethylsulfanyl)benzenecarboxylic acid

An ethanol/water mixed solution (2/1, 60 mL) of 4-mercaptobenzenecarboxylic acid (1.0 g), 2-chloromethylpyridine hydrochloride (2.1 g) and potassium carbonate (4.5 g) was heated under reflux for 4 hours. The organic solvent was evaporated off under reduced pressure, and aqueous 5 N hydrochloric acid solution was added to the residue until it became acidic. Water was evaporated off under reduced pressure, and DMF was added to the resulting residue and filtered. The filtrate was concentrated under reduced pressure, and the resulting residue was purified through silica gel column chromatography (chloroform/methanol=9/1 to 4/1) to obtain the entitled compound (650 mg).

PRODUCTION EXAMPLE 25-1

Methyl 4-tert-butoxycarbonylaminobenzenecarboxylate

4-Dimethylaminopyridine (242 mg) and di-tert-butyl dicarbonate (4.3 g) were added to an acetonitrile solution (50 mL) of methyl 4-aminobenzenecarboxylate (3.0 g), and stirred overnight at room temperature. The reaction solution was concentrated under reduced pressure, and the resulting residue was purified through silica gel column chromatography (hexane/ethyl acetate=9/1 to 4/1) to obtain the entitled compound (2.3 g).

PRODUCTION EXAMPLE 25-2

Methyl 4-(benzyl-tert-butoxycarbonylamino)benzenecarboxylate

A DMF solution (20 mL) of the compound (2.0 g) obtained in Production Example 25-1 was cooled to 0° C., and sodium hydride (956 mg) was added thereto and stirred in a nitrogen atmosphere at room temperature for 30 minutes. A DMF solution (2 mL) of benzyl bromide (4.1 g) was added to the reaction solution, and stirred at room temperature for 1 hour. Water was added to the reaction solution, and extracted with hexane/ethyl acetate (1/1). The organic layer was dried with anhydrous magnesium sulfate, and the solvent was evaporated off under reduced pressure. The resulting residue was purified through silica gel column chromatography (hexane/ethyl acetate=9/1 to 4/1) to obtain the entitled compound (2.4 g).

PRODUCTION EXAMPLE 25-3

4-(Benzyl-tert-butoxycarbonylamino)benzenecarboxylic acid

Aqueous 5 N sodium hydroxide solution (5.6 mL) was added to a methanol solution (10 mL) of the compound (1.9 g) obtained in Production Example 25-2, and stirred overnight at room temperature. Aqueous 5 N hydrochloric acid solution (5.3 mL) was added to the reaction solution, and then this was controlled to have a pH of 7.0 with aqueous saturated ammonium chloride solution. Under reduced pressure, the organic solvent was evaporated off, and the resulting residue was extracted with chloroform/methanol (10/1). The organic layer was dried with anhydrous magnesium sulfate, and the solvent was evaporated off under reduced pressure to obtain the entitled compound (1.9 g).

PRODUCTION EXAMPLE 26-1

Methyl 4-[(pyridine-2-carbonyl)amino]benzenecarboxylate

Diisopropylethylamine (2.3 mL) was added to a DMF solution (15 mL) of picolinic acid (814 mg), methyl 4-aminobenzenecarboxylate (1.0 g) and HATU (2.8 g), and stirred overnight at room temperature. Water was added to the reaction solution, and the resulting precipitate was taken out through filtration. The obtained residue was purified through silica gel column chromatography (chloroform/methanol=500/10 to 500/15) to obtain the entitled compound (1.4 g).

PRODUCTION EXAMPLE 26-2

4-[(Pyridine-2-carbonyl)amino]benzenecarboxylic acid

The entitled compound (250 mg) was obtained in the same manner as in Production Example 1-2, for which, however, the compound (300 mg) obtained in Production Example 26-1 and a methanol/THF mixed solvent (1/1, 5 mL) were used.

PRODUCTION EXAMPLE 27-1

Methyl 4-(pyridin-2-yloxy)benzenecarboxylate

2-Bromopyridine (1.00 g), methyl 4-hydroxybenzenecarboxylate (1.92 g) and potassium carbonate (874.9 mg) were stirred at 150° C. for 6 hours. Aqueous 2 N sodium hydroxide solution (50 mL) was added to the reaction liquid, extracted with diethyl ether (100 mL), and the organic layer was washed with water (50 mL) and saturated saline water (50 mL) in that order, and then evaporated under reduced pressure to obtain a pale yellow residue. The resulting residue was purified through silica gel column chromatography (hexane/ethyl acetate=9/1 to 8/2) to obtain the entitled compound (208 mg) as a pale yellow solid.

PRODUCTION EXAMPLE 27-2

4-(Pyridin-2-yloxy)benzenecarboxylic acid

The compound (200.0 mg) obtained in Production Example 27-1 was dissolved in methanol (0.5 mL) and acetone (0.5 mL), and aqueous 4 N sodium hydroxide solution (0.5 mL) was dropwise added thereto and stirred at room temperature for 5 hours. Water (5 mL) was added to the reaction liquid, and extracted with ethyl acetate (5 mL). The aqueous layer was made acidic (pH 3) with aqueous 10% hydrochloric acid solution, and the resulting precipitate was taken out through filtration and dried to obtain the entitled compound (135.6 mg) as a colorless solid.
$^1$H-NMR (400 MHz, DMSO-$d_6$, δ ppm): 7.13-7.15 (1H, m), 7.20-7.23 (3H, m), 7.91-7.93 (1H, m), 7.99 (2H, d, J=9.1 Hz), 8.20-2.19 (1H, m) ESI-MS Found: m/z 216 [M+H]$^+$

PRODUCTION EXAMPLE 28-1

Methyl 4-(5-nitropyridin-2-yloxy)benzenecarboxylate

2-Chloro-5-nitropyridine (500.0 mg), methyl 4-hydroxybenzenecarboxylate (958.6 mg) and potassium carbonate (1.31 g) were suspended in acetonitrile (5 mL), and heated under reflux for 16 hours. Water (50 mL) was added to the reaction liquid, extracted with ethyl acetate (50 mL), and the organic layer was washed with aqueous 2 N sodium hydroxide solution (50 mL), water (50 mL) and saturated saline water (50 mL) in that order. The organic layer was dried with magnesium sulfate, and evaporated under reduced pressure to obtain the entitled compound (867.7 mg) as a brown solid.

PRODUCTION EXAMPLE 28-2

Methyl 4-(5-aminopyridin-2-yloxy)benzenecarboxylate

The compound (867 mg) obtained in Production Example 28-1 was suspended in methanol (8 mL), and 10% palladium-carbon (83.0 mg) was added thereto, and stirred in a hydrogen atmosphere at room temperature under normal pressure for 15 hours. The reaction liquid was filtered through Celite, and the resulting filtrate was evaporated under reduced pressure to obtain the entitled compound (789.4 mg) as a gray solid.

PRODUCTION EXAMPLE 28-3

Methyl 4-(5-fluoropyridin-2-yloxy)benzenecarboxylate

42% tetrafluoroboric acid (1.8 mL) was added to the compound (789 mg) obtained in Production Example 28-2, and with cooling with ice/salt, sodium nitrite (233.1 mg) was added thereto and stirred for 1 hour. With cooling with ice, diethyl ether (5 mL) was added to the reaction liquid, and the resulting precipitate was taken out through filtration, and dried under reduced pressure to obtain a brown residue. The obtained residue was gradually added to toluene (8 mL) heated at 100° C., and then gradually heated under reflux for 1 hour. The solvent was evaporated off under reduced pressure, aqueous 2 N sodium hydroxide (10 mL) solution was added to it, and extracted with ethyl acetate (50 mL). The organic layer was washed with water (10 mL), and saturated saline water (10 mL) in that order, dried with magnesium sulfate, and evaporated under reduced pressure to obtain the entitled compound (488.2 mg) as a brown oil.

PRODUCTION EXAMPLE 28-4

4-(5-Fluoropyridin-2-yloxy)benzenecarboxylic acid

The compound (488 mg) obtained in Production Example 28-3 was dissolved in methanol (2 mL) and acetone (2 mL), and aqueous 4 N sodium hydroxide solution (0.96 mL) was dropwise added thereto and stirred at room temperature for 15 hours. Water (10 mL) was added to the reaction liquid, extracted with ethyl acetate (20 mL), the aqueous layer was made acidic (pH 3) with aqueous 10% hydrochloric acid solution, and the resulting precipitate was taken out through filtration and dried to obtain the entitled compound (282.4 mg) as a colorless solid.
$^1$H-NMR (400 MHz, CDCl$_3$, δ ppm): 7.00 (1H, dd, J=9.4, 3.9 Hz), 7.18 (2H, d, J=8.4 Hz), 7.47-7.52 (1H, m), 8.07 (1H, d, J=3.1 Hz), 8.13 (2H, d, J=8.4 Hz) ESI-MS Found: m/z 234 [M+H]$^+$

PRODUCTION EXAMPLE 29-1

Methyl 4-(6-fluoropyridin-2-yloxy)benzenecarboxylate 2,6-Difluoropyridine (1.0 g), methyl 4-hydroxybenzenecarboxylate (1.32 g) and potassium carbonate (3.60 g) were suspended in acetonitrile (10 mL), and heated under reflux for 21 hours. Water (100 mL) was added to the reaction liquid, extracted with ethyl acetate (100 mL), and the organic layer was washed with aqueous 2 N sodium hydroxide solution (100 mL), water (100 mL) and saturated saline water (100 mL) in that order, dried with magnesium sulfate, and evaporated under reduced pressure to obtain a colorless oil. The resulting oil was purified through silica gel column chromatography (hexane/ethyl acetate=10/0 to 7/3) to obtain the entitled compound (1.48 g) as a colorless solid.

PRODUCTION EXAMPLE 29-2

4-(6-Fluoropyridin-2-yloxy)benzenecarboxylic acid

The compound (1.4 g) obtained in Production Example 29-1 was dissolved in methanol (7 mL) and acetone (7 mL), and aqueous 4 N sodium hydroxide solution (2.85 mL) was dropwise added thereto and stirred at room temperature for 3 hours. Water (20 mL) was added to the reaction liquid, extracted with ethyl acetate (50 mL), the aqueous layer was made acidic (pH 3) with aqueous 10% hydrochloric acid solution, and the resulting precipitate was taken out through filtration and dried to obtain the entitled compound (1.23 g) as a colorless solid.
$^1$H-NMR (400 MHz, DMSO-$d_6$, δ ppm): 6.95 (1H, dd, J=7.8, 2.3 Hz), 7.03 (1H, d, J=7.8 Hz), 7.25 (2H, d, J=8.6 Hz), 7.99 (1H, d, J=8.6 Hz), 8.04-8.10 (1H, m) ESI-MS Found: m/z 234 [M+H]$^+$

PRODUCTION EXAMPLE 30-1

4-(3-Fluoropyridin-2-yloxy)benzenecarboxylic acid

2-Chloro-3-nitropyridine (500.0 mg) was processed in the same manner as in Production Example 28-1 to 284 to obtain the entitled compound (284.0 mg) as a pale brown solid.

¹H-NMR (400 MHz, CDCl₃, δ ppm): 7.06-7.10 (1H, m), 7.22-7.26 (2H, m), 7.50-7.54 (1H, m), 7.97-7.98 (1H, m), 8.15 (2H, d, J=8.8 Hz) ESI-MS Found: m/z 234 [M+H]⁺

PRODUCTION EXAMPLE 31-1

Methyl 4-(4-nitro-1-oxypyridin-2-yloxy)benzenecarboxylate

With cooling with ice, sodium hydride (4.63 g) was suspended in THF (200 mL), and methyl 4-hydroxybenzenecarboxylate (13.1 g) was added thereto and stirred for 30 minutes, and then 2-chloro-4-nitropyridine 1-oxide (10.0 g) was added thereto, heated up to 75° C. and stirred for 4.5 hours. Water (200 mL) was added to the reaction liquid, and extracted three times with ethyl acetate (200 mL). The organic layer of three ethyl acetate layers combined was washed with aqueous 2 N sodium hydroxide solution (200 mL), water (200 mL) and saturated saline water (200 mL) in that order, and evaporated under reduced pressure to obtain a brown residue. The resulting residue was washed with n-hexane to obtain the entitled compound (12.2 g) as a brown solid.

PRODUCTION EXAMPLE 31-2

Methyl 4-(4-aminopyridin-2-yloxy)benzenecarboxylate

The compound (10.01 g) obtained in Production Example 31-1 was dissolved in methanol (400 mL), and 10% palladium-carbon (2.03 g) was added thereto, and stirred in a hydrogen atmosphere at room temperature under normal pressure for 15 hours. The reaction liquid was filtered through Celite, and the filtrate was evaporated under reduced pressure to obtain the entitled compound (7.83 g) as a brown solid.

PRODUCTION EXAMPLE 31-3

Methyl 4-(4-chloropyridin-2-yloxy)benzenecarboxylate

The compound (205.4 mg) obtained in Production Example 31-2 was suspended in acetonitrile (5 mL), and cupric chloride (168.3 mg) was added thereto, and with cooling with ice, tert-butyl nitrite (146.0 μL) was added thereto, and stirred at room temperature for 22 hours. Water (20 mL) was added to the reaction liquid, and extracted twice with ethyl acetate (20 mL). The organic layer of two extracts combined was washed with saturated saline water (20 mL), dried with magnesium sulfate, and evaporated under reduced pressure to obtain a green residue. The resulting residue was purified through silica gel column chromatography (hexane/ethyl acetate=10/0 to 7/3) to obtain the entitled compound (140.5 mg) as a colorless solid.

PRODUCTION EXAMPLE 31-4

4-(4-Chloropyridin-2-yloxy)benzenecarboxylic acid

The compound (140.5 mg) obtained in Production Example 31-3 was dissolved in methanol (0.7 mL) and acetone (0.7 mL), and aqueous 4 N sodium hydroxide solution (0.53 mL) was dropwise added thereto and stirred at room temperature for 6 hours. Water (5 mL) was added to the reaction liquid, and extracted with ethyl acetate (10 mL). The aqueous layer was made acidic (pH 3) with aqueous 10% hydrochloric acid solution, and the resulting precipitate was taken out through filtration and dried to obtain the entitled compound (135.6 mg) as a colorless solid.

¹H-NMR (400 MHz, DMSO-d₆, δ ppm): 7.25 (2H, d, J=9.2), 7.33-7.35 (2H, m), 7.99 (2H, d, J=9.2 Hz), 8.18 (1H, dd, J=5.2, 1.2 Hz) ESI-MS Found: m/z 245 [M+H]⁺

PRODUCTION EXAMPLE 32-1

Methyl 4-(4-methylsulfanylpyridin-2-yloxy)benzenecarboxylate

Dimethyl disulfide (147.5 μL) and tert-butyl nitrite (146.0 μL) were dissolved in chloroform (4 mL), and stirred at 40° C., and then the compound (202.6 mg) obtained in Production Example 31-2 was added thereto, stirred for 1 hour, and then further stirred for 18 hours at 20° C. Water was added to the reaction liquid, extracted with ethyl acetate (50 mL), and the organic layer was dried with magnesium sulfate, and evaporated under reduced pressure to obtain the entitled compound (119.8 mg) as a pale yellow oil.

PRODUCTION EXAMPLE 32-2

4-(4-Methylsulfanylpyridin-2-yloxy)benzenecarboxylic acid

The compound (119.8 mg) obtained in Production Example 32-1 was dissolved in methanol (0.5 mL) and acetone (0.5 mL), and aqueous 4 N sodium hydroxide solution (0.44 mL) was dropwise added thereto and stirred at room temperature for 5 hours. Water (5 mL) was added to the reaction liquid, and extracted with ethyl acetate (20 mL). The organic layer was made acidic (pH 3) with aqueous 10% hydrochloric acid solution, and the resulting precipitate was taken out through filtration and dried to obtain the entitled compound (87.5 mg) as a colorless solid.

¹H-NMR (400 MHz, DMSO-d₆, δ ppm): 2.55 (3H, s), 6.98 (1H, d, J=1.2 Hz), 7.07 (1H, dd, J=5.2, 1.6 Hz), 7.19 (2H, d, J=9.2 Hz), 7.95-7.99 (3H, m) CI-MS Found: m/z 262 [M+H]⁺

PRODUCTION EXAMPLE 33-1

Ethyl 4-(5-trifluoromethylpyridin-2-yloxy)benzenecarboxylate

Potassium carbonate (1.4 g) and 2-bromo-5-trifluoromethylpyridine (450 mg) were added to an acetonitrile solution (10 mL) of ethyl 4-hydroxybenzenecarboxylate (221 mg), and heated overnight under reflux. The reaction solution was concentrated under reduced pressure, water was added to the residue and extracted with ethyl acetate. The organic layer was dried with anhydrous magnesium sulfate, and the solvent was evaporated off under reduced pressure. The resulting residue was purified through silica gel column chromatography (hexane/ethyl acetate=9/1 to 4/1) to obtain the entitled compound (330 mg).

PRODUCTION EXAMPLE 33-2

4-(5-Trifluoromethylpyridin-2-yloxy)benzenecarboxylic acid

In the same manner as in Production Example 1-2 but using ethanol (5 mL) as a solvent, the compound (667 mg) obtained in Production Example 33-1 was processed to obtain the entitled compound (539.8 mg).

PRODUCTION EXAMPLE 34-1

Methyl 4-(3-trifluoromethylpyridin-2-yloxy)benzenecarboxylate

2-Chloro-3-trifluoromethylpyridine (1.0 g), methyl 4-hydroxybenzenecarboxylate (838.3 mg) and potassium carbonate (2.28 g) were suspended in acetonitrile (10 mL), and heated under reflux for 27 hours, and then 2-chloro-3-trifluoromethylpyridine (1.0 g) was added thereto and further heated under reflux for 24 hours. Water (100 mL) was added to the reaction liquid, extracted with ethyl acetate (100 mL), and the organic layer was washed with aqueous 2 N sodium hydroxide solution (100 mL), water (100 mL) and saturated saline water (100 mL) in that order, dried with magnesium sulfate and evaporated under reduced pressure to obtain a pale yellow oil. The resulting oil was purified through silica gel column chromatography (hexane/ethyl acetate=8/2) to obtain the entitled compound (1.35 g) as a pale yellow oil.

PRODUCTION EXAMPLE 34-2

4-(3-Trifluoromethylpyridin-2-yloxy)benzenecarboxylic acid

The compound (1.3 g) obtained in Production Example 34-1 was dissolved in methanol (5 mL) and acetone (5 mL), and aqueous 4 N sodium hydroxide solution (2.19 mL) was dropwise added thereto and stirred at room temperature for 4 hours. Water (20 mL) was added to the reaction liquid, and extracted with ethyl acetate (50 mL). The organic layer was made acidic (pH 3) with aqueous 10% hydrochloric acid solution, and the resulting precipitate was taken out through filtration and dried to obtain the entitled compound (891.8 mg) as a colorless solid.
$^1$H-NMR (400 MHz, CDCl$_3$, δ ppm): 7.14-7.18 (1H, m), 7.26 (2H, d, J=8.4 Hz), 8.03 (1H, dd, J=7.6, 1.6 Hz), 8.18 (2H, d, J=8.4 Hz), 8.32 (1H, dd, J=4.8, 1.6 Hz) ESI-MS Found: m/z 284 [M+H]$^+$

PRODUCTION EXAMPLE 35-1

Methyl 4-(4-trifluoromethylpyridin-2-yloxy)benzenecarboxylate

2-Chloro-4-trifluoromethylpyridine (1.0 g), methyl 4-hydroxybenzenecarboxylate (838.3 mg) and potassium carbonate (2.28 g) were suspended in acetonitrile (10 mL), heated under reflux for 27 hours, and methyl 4-hydroxybenzenecarboxylate (838.3 mg) was added thereto and further heated under reflux for 24 hours. Water (100 mL) was added to the reaction liquid, extracted with ethyl acetate (100 mL), and the organic layer was washed with aqueous 2 N sodium hydroxide solution (100 mL), water (100 mL) and saturated saline water (100 mL) in that order, dried with magnesium sulfate, and evaporated under reduced pressure to obtain a pale yellow oil. The resulting oil was purified through silica gel column chromatography (hexane/ethyl acetate=8/2) to obtain the entitled compound (740 mg) as a colorless solid.

PRODUCTION EXAMPLE 35-2

4-(4-Trifluoromethylpyridin-2-yloxy)benzenecarboxylic acid

The compound (740 mg) obtained in Production Example 35-1 was dissolved in methanol (3.5 mL) and acetone (3.5 mL), and aqueous 4 N sodium hydroxide solution (1.18 mL) was dropwise added thereto and stirred at room temperature for 4 hours. Water (20 mL) was added to the reaction liquid, and extracted with ethyl acetate (50 mL). The aqueous layer was made acidic (pH 3) with aqueous 10% hydrochloric acid solution, and the resulting precipitate was taken out through filtration and dried to obtain the entitled compound (698.4 mg) as a colorless solid.
$^1$H-NMR (400 MHz, CDCl$_3$, δ ppm): 7.23-7.27 (4H, m), 8.18 (2H, d, J=8.4 Hz), 8.35 (1H, d, J=5.6 Hz) ESI-MS Found: m/z 284 [M+H]$^+$

PRODUCTION EXAMPLE 36-1

Ethyl 4-(6-chloropyridazin-3-yloxy)benzenecarboxylate

Ethyl 4-hydroxybenzenecarboxylate (558 mg) and 2,5-dichloropyridazine (500 mg) were processed in the same manner as in Production Example 28-1 to obtain the entitled compound (640 mg).

PRODUCTION EXAMPLE 36-2

4-(6-Chloropyridazin-3-yloxy)benzenecarboxylic acid

In the same manner as in Production Example 1-2 but using ethanol (20 mL) as a solvent, the compound (1.28 g) obtained in Production Example 36-1 was processed to obtain the entitled compound (1.1 g).

PRODUCTION EXAMPLE 37-1

Ethyl 4-phenethyloxybenzenecarboxylate

2-Phenylethanol (2.0 g) and ethyl 4-hydroxybenzenecarboxylate (2.7 g) were processed in the same manner as in Production Example 11-2 to obtain the entitled compound (4.4 g).

PRODUCTION EXAMPLE 37-2

4-Phenethyloxybenzenecarboxylic acid

The compound (4.4 g) obtained in Production Example 37-1 was processed in the same manner as in Production Example 1-2 to obtain the entitled compound (3.6 g).

PRODUCTION EXAMPLE 38-1

1-(2-Trans-methylcyclopropyl)propan-1-one

Sodium hydride (4.98 g) was suspended in DMSO (60 mL) and cooled to 0° C., and trimethylsulfonium iodide (27.2 g) was added thereto in a few times as its portions divided. This was stirred at room temperature for 2 hours, then again cooled to 0° C., and a DMSO solution (40 mL) of 4-hexen-3-one (10 g) was added thereto over 20 minutes. The reaction liquid was stirred at room temperature for 1.5 hours, and then at 50° C. for 3 hours. A dark brown reaction liquid was diluted with water (50 mL), and extracted three times with diethyl ether (150 mL). The ether layers were combined, washed with saturated saline water (50 mL), dried with anhydrous magnesium sulfate, filtered, and concentrated under normal pressure. The residue was evaporated under reduced pressure (56° C./30 mmHg) to obtain the entitled compound (4.94 g) as a colorless liquid.

PRODUCTION EXAMPLE 38-2

2-Bromo-1-(2-trans-methylcyclopropyl)propan-1-one

The compound (3.9 g) obtained in Production Example 38-1 was dissolved in methanol (40 mL), and 0.1 mL of bromine was added thereto at room temperature, and stirred for 30 minutes. Then the reaction liquid was cooled to 0° C., and bromine (1.5 mL) was added thereto over 20 minutes. This was stirred at 0° C. for 30 minutes and then at room temperature for 1 hour, and water (50 mL) was added thereto and vigorously stirred overnight at room temperature. Potassium carbonate (4.3 g) was added to the reaction liquid, and extracted three times with diethyl ether (100 mL). These ether layers were combined, washed with saturated saline water (50 mL), dried with anhydrous magnesium sulfate, and concentrated to obtain the entitled compound (7.3 g) as a colorless liquid.

PRODUCTION EXAMPLE 38-3

4-Methyl-N-(5-nitropyridin-2-yl)benzenesulfonamide

P-toluenesulfonyl chloride (143.9 g) was added to a pyridine solution (800 mL) of 2-amino-5-nitropyridine (100 g), and stirred overnight at 110° C. The reaction solution was poured into water with ice, and stirred at 15° C. or lower for 30 minutes. The precipitate was taken out through filtration, and the resulting residue was washed with water, diethyl ether (1500 mL) and ethyl acetate (1000 mL), and dried under reduced pressure to obtain the entitled compound (176.8 g).

PRODUCTION EXAMPLE 38-4

4-Methyl-N-{1-[1-methyl-2-(2-trans-methylcyclopropyl)-2-oxoethyl]-5-nitro-1H-pyridin-2-ylidene}benzenesulfonamide The compound (10.21 g) obtained in Production Example 38-3 was suspended in THF (50 mL), and with cooling with ice, a THF solution (25 mL) of diisopropylethylamine (12.1 mL) and the compound (7.3 g) obtained in Production Example 38-2 was added thereto over 15 minutes, and stirred at room temperature for 20 hours. Aqueous saturated sodium hydrogencarbonate solution (100 mL) was added to the reaction liquid, the organic layer was separated, and the aqueous layer was extracted twice with ethyl acetate (50 mL). The organic layers were combined, washed with saturated saline water (50 mL), and dried with anhydrous magnesium sulfate. Then the organic layer was concentrated, and the resulting residue was purified through silica gel column chromatography (hexane/ethyl acetate=3/1 to 1/1) to obtain the entitled compound (7.61 g).

PRODUCTION EXAMPLE 38-5

3-Methyl-2-(2-trans-methylcyclopropyl)-6-nitroimidazo[1,2-a]pyridine

The compound (7.61 g) obtained in Production Example 384 was dissolved in dichloroethane (75 mL), and with cooling with ice, trifluoroacetic anhydride (5.3 mL) was dropwise added thereto, and stirred at room temperature for 24 hours. Aqueous saturated sodium hydrogencarbonate solution (150 mL) was added to the reaction liquid, and extracted three times with chloroform. The chloroform layers were combined, and the resulting organic layer was dried with anhydrous sodium sulfate, concentrated, and the resulting yellow solid was suspended in an ethyl acetate/diisopropyl ether mixed solvent, and filtered to obtain the entitled compound (3.8 g) as an yellow solid.

PRODUCTION EXAMPLE 38-6

3-Methyl-2-(2-trans-methylcyclopropyl)imidazo[1,2-a]pyridin-6-ylamine dihydrochloride The compound (3.77 g) obtained in Production Example 38-5 was dissolved in methanol (40 mL), and 10% palladium-carbon (434 mg) was added thereto, and in a hydrogen atmosphere (1 atm), this was stirred at room temperature for 7 hours. The reaction liquid was filtered, the filtrate was concentrated, the residue was dissolved in ethyl acetate (100 mL), 4 N hydrochloric acid/ethyl acetate solution (8 mL) was added thereto, and the resulting brown precipitate was taken out through filtration to obtain the entitled compound (4.34 g) as a brown solid.

$^1$H-NMR (400 MHz, CD$_3$OD, δ ppm): 1.0-1.07 (m, 1H), 1.15-1.21 (m, 1H), 1.31 (d, J=5.5 Hz, 3H), 1.33-1.41 (m, 1H), 1.88-1.94 (m, 1H), 2.58 (s, 3H), 7.63 (dd, J=9.4, 2.0 Hz, 1H), 7.69 (d, J=9.0 Hz, 1H), 8.09 (s, 1H)

PRODUCTION EXAMPLE 39-1

2-Bromopentan-3-one

With cooling with ice, bromine (6.3 mL) was added to a methanol solution (100 mL) of 3-pentanone (9.6 g). The reaction liquid was gradually heated up to room temperature, stirred for 5 hours, and then water (100 mL) was added thereto and stirred overnight. Water was further added to the reaction liquid, then extracted with diethyl ether, and the organic layer was washed with saturated sodium hydrogencarbonate solution and saturated saline water. The obtained organic layer was dried and concentrated under reduced pressure to obtain the entitled compound (17.1 g).

PRODUCTION EXAMPLE 39-2

4-Methyl-N-[1-(1-methyl-2-oxobutyl)-5-nitro-1H-pyridin-2-ylidene]benzenesulfonamide Diisopropylethylamine (17.5 mL) was added to a tetrahydrofuran solution (175 mL) of the compound (17.1 g) obtained in Production Example 39-1 and the compound (14.7 g) obtained in Production Example 38-3, and stirred overnight. Water was added to the reaction liquid, extracted with ethyl acetate, and the ethyl acetate layer was washed with saturated saline water. The organic layer was dried, concentrated under reduced pressure, purified through silica gel column chromatography (hexane/ethyl acetate=9/1 to 1/1), and crystallized to obtain the entitled compound (14.1 g).

PRODUCTION EXAMPLE 39-3

2-Ethyl-3-methyl-6-nitroimidazo[1,2-a]pyridine

With cooling with ice, trifluoroacetic anhydride (60 mL) was added to a chloroform solution (180 mL) of the compound (14.1 g) obtained in Production Example 39-2, and stirred overnight. The reaction liquid was concentrated, the residue was neutralized with aqueous sodium hydrogencarbonate solution, extracted with ethyl acetate, and the ethyl acetate layer was washed with saturated saline water. The resulting ethyl acetate layer was dried, and concentrated under reduced pressure to obtain the entitled compound (7.1 g).

PRODUCTION EXAMPLE 39-4

2-Ethyl-3-methylimidazo[1,2-a]pyridin-6-ylamine dihydrochloride

In a hydrogen atmosphere, a methanol solution (70 mL) of the compound (7.1 g) obtained in Production Example 39-3 was stirred in the presence of palladium-carbon (10%, 1.0 g), at room temperature in a hydrogen atmospher for 2 hours. The palladium-carbon was separated through filtration, and 4 N hydrochloric acid/ethyl acetate solution (20 mL) was added to the filtrate, and then concentrated to obtain the entitled compound (7.79 g).

PRODUCTION EXAMPLE 40-1

2-Bromo-4-methylpentan-3-one

At 0° C., a methanol solution (20 mL) of bromine (5.4 mL) was added to a methanol solution (80 mL) of 2-methyl-3-pentanone (10.0 g), and stirred at room temperature for 2 hours. Water (100 mL) was added to the reaction liquid, stirred overnight, and concentrated under reduced pressure. The residue was neutralized with aqueous sodium hydrogencarbonate solution added thereto, and then extracted with diethyl ether. The organic layer was washed with saturated saline water, dried with anhydrous sodium sulfate, and concentrated under reduced pressure. The residue was dried to obtain the entitled compound (12.9 g) as a colorless oily substance.

PRODUCTION EXAMPLE 40-2

N-[1-(1,3-dimethyl-2-oxobutyl)-5-nitro-1H-pyridin-2-ylidene]-4-methylbenzenesulfonamide Diisopropylethylamine (11.8 mL) was added to a THF solution (110 mL) of the compound (10.0 g) obtained in Production Example 38-3 and the compound (12.1 g) obtained in Production Example 40-1, at 0° C., and stirred at room temperature for 3 days. Aqueous sodium hydrogencarbonate solution was added to the reaction liquid, and extracted with ethyl acetate. The organic layer was washed with saturated saline water, dried with anhydrous sodium sulfate, and concentrated under reduced pressure. The residue was purified through silica gel column chromatography (chloroform/methanol=95/5) to obtain the entitled compound (12.6 g) as a red brown crystal.
$^1$H-NMR (400 MHz, DMSO-$d_6$, δ ppm): 0.97 (3H, d, J=6.8 Hz), 0.98 (3H, d, J=6.8 Hz), 1.68 (3H, d, J=7.2 Hz), 2.36 (3H, s), 2.85 (1H, dq, J1=J2=6.8 Hz), 5.71 (1H, q, J=7.2 Hz), 7.33 (2H, d, J=8.4 Hz), 7.51 (1H, d, J=9.6 Hz), 7.64 (2H, d, J=8.4 Hz), 8.41 (1H, dd, J1=9.6 Hz, J2=2.8 Hz), 9.10 (1H, d, J=2.8 Hz) ESI-MS Found: m/z 392 [M+H]$^+$, 390 [M−H]$^-$

PRODUCTION EXAMPLE 40-3

2-Isopropyl-3-methyl-6-nitroimidazo[1,2-a]pyridine

At 0° C., trifluoroacetic anhydride (140 mL) was added to a methylene chloride solution (160 mL) of the compound (12.5 g) obtained in Production Example 40-2, and stirred overnight at room temperature. The reaction liquid was heated under reflux for 3 days, and then concentrated under reduced pressure. Aqueous sodium hydrogencarbonate solution was added to the reaction liquid, and extracted with ethyl acetate. The organic layer was washed with saturated saline water, dried with anhydrous sodium sulfate, and concentrated under reduced pressure. The residue was diluted with diisopropyl ether (200 mL) and ultrasonically dissolved. The insoluble matter was removed through filtration, the filtrate was concentrated under reduced pressure, and dried to obtain the entitled compound (3.86 g) as a brown crystal.
$^1$H-NMR (400 MHz, DMSO-$d_6$, δ ppm): 1.26 (6H, d, J=6.8 Hz), 2.52 (3H, s), 3.19 (1H, dq, J1=J2=6.8 Hz), 7.62 (1H, d, J=10.0 Hz), 7.86 (1H, d, J=10.0 Hz), 9.30 (1H, s) ESI-MS Found: m/z 220 [M+H]$^+$

PRODUCTION EXAMPLE 40-4

2-Isopropyl-3-methylimidazo[1,2-a]pyridin-6-ylamine dihydrochloride

The compound obtained in Production Example 40-3 was processed in the same manner as in Production Example 38-6 to obtain the entitled compound.

PRODUCTION EXAMPLE 41-1

2-Cyclopropyl-3-methylimidazo[1,2-a]pyridin-6-ylamine dihydrochloride

2-Cyclopropyl-3-methyl-6-nitroimidazo[1,2-a]pyridine produced according to JP-A 2003-207632 was processed in the same manner as in Production Example 38-6 to obtain the entitled compound.

PRODUCTION EXAMPLE 42-1

3-Methyl-2-(tetrahydrofuran-3-yl)imidazo[1,2-a]pyridin-6-ylamine dihydrochloride 3-Methyl-6-nitro-2-(tetrahydrofuran-3-yl)imidazo[1,2-a]pyridine produced according to JP-A 2003-207632 was processed in the same manner as in Production Example 38-6 to obtain the entitled compound.

PRODUCTION EXAMPLE 43-1

(2-Bromo-1-bromomethylethoxymethyl)benzene

The entitled compound was produced according to the method by M. Avram (Chem. Ber. (1957), 90, 1424), et al.

PRODUCTION EXAMPLE 43-2

Diisopropyl 3-benzyloxycyclobutane-1,1-dicarboxylate

Sodium hydride (60%, 26.0 g) was washed with hexane, and DMF (250 mL) was added thereto. Diisopropyl malonate (120 mL) was dropwise added to the resulting DMF suspension, and the compound (96.25 g) obtained in Production Example 43-1 was added thereto, and stirred overnight at 140° C. The reaction solution was cooled to room temperature, water (500 mL) was added thereto, and extracted with diethyl ether (500 mL×2). The ether layers were combined, and the resulting organic layer was washed with water (500 mL×2) and saturated saline water (300 mL). Then, the organic layer was dried, concentrated, and the resulting residue was purified through silica gel column chromatography (hexane/ethyl acetate=30/1 to 15/1) to obtain the entitled compound (84.5 g).

PRODUCTION EXAMPLE 43-3

Diisopropyl 3-hydroxycyclobutane-1,1-dicarboxylate

A methanol solution (150 mL) of the compound (20.11 g) obtained in Production Example 43-2 was stirred overnight in the presence of palladium-carbon (10%, 1.0 g), in a hydrogen atmosphere. The palladium-carbon was removed through filtration from the reaction mixture, and the filtrate was concentrated to obtain the entitled compound (14.7 g).

PRODUCTION EXAMPLE 43-4

3-Methoxycyclobutane-1,1-dicarboxylic acid

Methyl iodide (7.45 mL) was added to a mixed THF (100 mL)/DMF (50 mL) solution of the compound (14.7 g) obtained in Production Example 43-3, and with cooling with ice, sodium hydride (60%, 3.61 g) was gradually added thereto. This was stirred overnight, and water was gradually added to the reaction liquid, and extracted with diethyl ether. The ether layer was washed with water and saturated saline water, dried, and concentrated. Methanol (120 mL) and aqueous 4 N sodium hydroxide solution (60 mL) were added in that order to the residue, and heated under reflux overnight. Methanol was evaporated off from the reaction liquid, and the residue was partitioned between water and diethyl ether added thereto. Then concentrated hydrochloric acid was added to the aqueous layer to make it acidic, and then extracted with ethyl acetate. The ethyl acetate layer was washed with saturated saline water, dried, and concentrated to obtain the entitled compound (8.74 g).

PRODUCTION EXAMPLE 43-5

3-Methoxycyclobutanecarboxylic acid

The compound (8.74 g) obtained in Production Example 43-4 was heated under reduced pressure at 190° C. for 3 hours to obtain the entitled compound (6.36 g).

PRODUCTION EXAMPLE 43-6

1-(3-Methoxycyclobutyl)propan-1-one

Oxalyl chloride (2.04 mL) and DMF (10 μL) were added to a chloroform solution (10 mL) of the compound (2.53 g) obtained in Production Example 43-5, and stirred for 2 hours. The reaction liquid was concentrated, THF (100 mL) was added thereto, and cooled to −78° C. Next, ethylmagnesium bromide (3 M diethyl ether solution, 6.5 mL) was dropwise added thereto, then water was added to the reaction solution, and extracted with diethyl ether. The organic layer was washed with saturated saline water, dried and concentrated to obtain the entitled compound (2.58 g).

PRODUCTION EXAMPLE 43-7

N-{1-[2-(3-methoxycyclobutyl)-1-methyl-2-oxoethyl]-5-nitro-1H-pyridin-2-ylidene}-4-methylbenzenesulfonamide At room temperature, bromine (1.0 mL) was gradually and dropwise added to a methanol solution (30 mL) of the compound (2.58 g) obtained in Production Example 43-6. After stirred for 1 hour, water (100 mL) was added to it, and further stirred overnight. The reaction liquid was extracted with diethyl ether, and washed with aqueous saturated sodium hydrogencarbonate solution and saturated saline water. The organic layer was dried and concentrated. THF (56 mL), the compound (4.7 g) obtained in Production Example 38-3 and diisopropylethylamine (5.6 mL) were added to the resulting residue, and stirred overnight at room temperature. Water was added to the reaction solution, extracted with ethyl acetate, and the ethyl acetate layer was washed with saturated saline water. The ethyl acetate layer was dried, concentrated, and the residue was purified through silica gel column chromatography (hexane/ethyl acetate=3/1 to 1/2) to obtain the entitled compound (4.44 g).

PRODUCTION EXAMPLE 43-8

2-(3-Methoxycyclobutyl)-3-methyl-6-nitroimidazo[1,2-a]pyridine

Trifluoroacetic anhydride (10 mL) was added to a dichloromethane solution (40 mL) of the compound (4.44 g) obtained in Production Example 43-7, and stirred at room temperature for 3 hours. The reaction solution was concentrated, aqueous sodium hydrogencarbonate solution was added to the residue, and extracted with ethyl acetate. The organic layer was washed with saturated saline water, dried, concentrated, and the residue was purified through silica gel column chromatography (hexane/ethyl acetate=2/1 to 2/3) to obtain the entitled compound (cis form, 1.45 g; trans form, 660 mg).

PRODUCTION EXAMPLE 43-9

2-(3-trans-methoxycyclobutyl)imidazo[1,2-a]pyridin-6-ylamine dihydrochloride

The trans compound obtained in Production Example 43-8 was processed in the same manner as in Production Example 38-6 to obtain the entitled compound.

PRODUCTION EXAMPLE 44-1

3-Benzyloxycyclobutanecarboxylic acid

Aqueous 4 N sodium hydroxide solution (100 mL) was added to a methanol solution (100 mL) of the compound (33.2 g) obtained in Production Example 43-2, and stirred overnight under reflux. The reaction liquid was diluted with water added thereto, and made acidic with concentrated hydrochloric acid, and the precipitated solid was collected. The obtained solid was heated under reduced pressure at 200° C. for 1 hour to obtain the entitled compound (16.58 g).

PRODUCTION EXAMPLE 44-2

1-(3-Benzyloxycyclobutyl)propan-1-one

Oxalyl chloride (5.5 mL) was added to a chloroform solution (100 mL) of the compound (10.84 g) obtained in Production Example 44-1, and stirred overnight. The reaction liquid was concentrated, THF (100 mL) was added thereto, and cooled to −78° C. At that temperature, ethylmagnesium bromide (2 M diethyl ether solution, 18 mL) was dropwise added thereto, then water was added to the reaction solution, and extracted with ethyl acetate. The organic layer was washed with aqueous 2 N hydrochloric acid solution, aqueous saturated sodium hydrogencarbonate solution and saturated saline water in that order, dried, and concentrated to obtain the entitled compound (11.48 g).

PRODUCTION EXAMPLE 44-3

1-(3-hydroxycyclobutyl)propan-1-one

Palladium-carbon (2.0 g) was added to a THF solution (100 mL) of the compound (11.48 g) obtained in Production Example 44-2, and stirred overnight in a hydrogen atmosphere. The palladium-carbon was removed through filtration, and the filtrate was concentrated to obtain the entitled compound (6.80 g).

PRODUCTION EXAMPLE 44-4

N-{1-[2-(3-hydroxycyclobutyl)-1-methyl-2-oxoethyl]-5-nitro-1H-pyridin-2-ylidene}-4-methylbenzenesulfonamide At room temperature, bromine (3.0 mL) was gradually and dropwise added to a methanol solution (70 mL) of the compound (6.80 g) obtained in Production Example 44-3. After stirred for 1.5 hours, water (100 mL) was added to it, and further stirred overnight. Methanol was evaporated off, the residue was extracted with diethyl ether, and the organic layer was washed with aqueous saturated sodium hydrogencarbonate solution and saturated saline water. The organic layer was dried and concentrated. THF (100 mL), the compound (10.2 g) obtained in Production Example 38-3 and diisopropylethylamine (12.2 mL) were added to the obtained residue, and stirred overnight at room temperature. Water was added to the reaction solution, extracted with ethyl acetate, and washed with saturated saline water. The organic layer was dried, concentrated, and the resulting residue was purified through silica gel column chromatography (hexane/ethyl acetate=1/1 to 1/3) to obtain the entitled compound (9.37 g).

PRODUCTION EXAMPLE 44-5

3-(3-Methyl-6-nitroimidazo[1,2-a]pyridin-2-yl)cyclobutanol p-toluenesulfonate

Trifluoroacetic anhydride (16 mL) was added to a chloroform solution (100 mL) of the compound (9.37 g) obtained in Production Example 44-4, and stirred overnight at room temperature. The reaction solution was concentrated, methanol (500 mL) was added to the residue, and stirred for 4 days. The reaction mixture was further concentrated to obtain the entitled compound (8.80 g).

PRODUCTION EXAMPLE 44-6

3-(3-Methyl-6-nitroimidazo[1,2-a]pyridin-2-yl)cyclobutanone

Triethylamine (15 mL) and $SO_3$-pyridine complex (6.68 g) were added in that order to a dimethylsulfoxide solution (50 mL) of the compound (8.80 g) obtained in Production Example 44-5, and stirred for 1 hour. Diethyl ether (100 mL) and water (400 mL) were added to the reaction solution, and the precipitated crystal was collected to obtain the entitled compound (3.55 g).

PRODUCTION EXAMPLE 44-7

3-(6-Aminoimidazo[1,2-a]pyridin-2-yl)cyclobutanone dihydrochloride

The compound obtained in Production Example 44-6 was processed in the same manner as in Production Example 38-6 to obtain the entitled compound.

PRODUCTION EXAMPLE 45-1

Methyl 6-tert-butoxycarbonylamino-3-methylimidazo[1,2-a]pyridine-3-carboxylate

1) An ethanol suspension (400 mL) of methyl 3-bromo-2-oxobutyrate (46.6 g) and 2-amino-5-nitropyridine (33.3 g) was stirred at 90° C. for 24 hours. The precipitated solid was taken out through filtration, and the obtained solid was suspended in ethyl acetate, washed with aqueous saturated sodium hydrogencarbonate solution, and purified through silica gel column chromatography (hexane/ethyl acetate=2/1) to obtain methyl 3-methyl-6-nitroimidazo[1,2-a]pyridine-2-carboxylate (13.0 g) as a yellow crystal.

2) 5% palladium-carbon (250 mg) was added to a THF (200 mL)/methanol (150 mL) mixed solution of the compound (6.0 g) obtained in 1), then the system was purged with hydrogen gas, and stirred for 6 hours. The reaction liquid was filtered, concentrated under reduced pressure, then THF (300 mL), acetonitrile (150 mL), di-tert-butyl dicarbonate (6.1 g) and triethylamine (3.9 mL) were added in that order to the residue, and stirred at 70° C. for 2 days. Next, the reaction liquid was concentrated under reduced pressure, and diluted with ethyl acetate (100 mL). The resulting solid was taken out through filtration to obtain the entitled compound (4.6 g) as a yellow solid.

ESI-MS Found: m/z 306 [M+H]$^+$

PRODUCTION EXAMPLE 45-2

Tert-butyl[2-(1-hydroxy-1-methylethyl)-3-methylimidazo[1,2-a]pyridin-6-yl]carbamate At 0° C., 3 N methylmagnesium bromide/ether solution (24 mL) was added to a THF solution (120 mL) of the compound (2.29 g) obtained in Production Example 45-1, and stirred at room temperature for 17 hours. At 0° C., aqueous saturated ammonium chloride solution was added to the reaction liquid, and extracted with ethyl acetate. The organic layer was washed with saturated saline water, dried, concentrated under reduced pressure, and the resulting residue was purified through silica gel column chromatography (hexane/ethyl acetate=1/1 to 1/3 to ethyl acetate alone, and then ethyl acetate/methanol=20/1) to obtain the entitled compound (1.54 g).

PRODUCTION EXAMPLE 45-3

2-(6-Amino-3-methylimidazo[1,2-a]pyridin-2-yl)propan-2-ol dihydrochloride

4 N hydrochloric acid/ethyl acetate solution (30 mL) was added to an ethyl acetate solution (50 mL) of the compound (1.54 g) obtained in Production Example 45-2, and stirred at room temperature for 17 hours. The precipitated solid was taken out through filtration to obtain the entitled compound (1.40 g).

PRODUCTION EXAMPLE 46-1

Methyl 6-(acetylamino)-3-methylimdazo[1,2-a]pyridine-2-carboxylate

10% palladium-carbon (250 mg) was added to a methanol/THF mixed solution (1/5, 60 mL) of the compound (1.1 g) obtained in Production Example 45-1, 1), in a nitrogen atmosphere at room temperature. In a hydrogen atmosphere (1 atm), this was stirred at room temperature for 7 hours, and the catalyst was removed through filtration. The mother liquor was concentrated, and dried under reduced pressure. The residue was dissolved in dichloromethane/THF/acetonitrile mixed solvent (1/1/2, 40 mL), and then triethylamine (2.0 mL) and acetyl chloride (0.5 mL) were added thereto at room temperature.

After stirred for 12 hours, the reaction solution was poured into aqueous saturated sodium hydrogencarbonate solution, and extracted with chloroform. The organic layer was dried with sodium sulfate, and then concentrated under reduced pressure. The residue was purified through silica gel column chromatography (methanol/chloroform=1/100 to 1/30) to obtain the entitled compound (905 mg).

PRODUCTION EXAMPLE 46-2

N-[2-(hydroxymethyl)-3-methylimidazo[1,2-a]pyridin-6-yl]acetamide

Lithiumaluminium hydride (250 mg) was added to a THF solution (150 mL) of the compound (850 mg) obtained in Production Example 46-1 in a nitrogen atmosphere at 0° C. This was stirred for 5 hours at that temperature, then sodium sulfate 10-hydrate was added thereto, and stirred at room temperature for 1 hour. The insoluble matter was removed through filtration, and the filtrate was concentrated under reduced pressure. The residue was purified through silica el column chromatography (methanol/chloroform=1/10 to 1/8) to obtain the entitled compound (309 mg).

PRODUCTION EXAMPLE 46-3

N-[3-methyl-2-(pyrrolidin-1-ylmethyl)imidazo[1,2-a]pyridin-6-yl]acetamide

Triethylamine (0.307 mL) and methanesulfonyl chloride (85.1 µL) were added to a dichloromethane suspension (5 mL) of the compound (120 mg) obtained in Production Example 46-2, at room temperature. After stirred for 1 hour, the reaction solution was dropwise added to pyrrolidine (2.0 mL) at room temperature. After stirred for 2 hours, the reaction solution was concentrated under reduced pressure. The residue was purified through silica gel chromatography (methanol/chloroform=1/100 to 1/30) to obtain the entitled compound (94.6 mg).

PRODUCTION EXAMPLE 47-1

4-Oxohexanoic acid

A diethyl ether solution (66 mL) of 3.0 M ethylmagnesium bromide was dropwise added to a benzene (50 mL) solution of succinyl chloride (15.5 g) at 0° C. After stirred for 3 hours, the reaction liquid was poured into a mixture of concentrated sulfuric acid and ice. The resulting mixture was extracted with diethyl ether, the organic layer was washed with water, and aqueous saturated sodium hydrogencarbonate solution was added thereto. After this was stirred for 3 hours, the organic layer was separated. The aqueous layer was made acidic with concentrated sulfuric acid, and then saturated with salt. The resulting mixture was extracted with diethyl ether, and the organic layer was dried with sodium sulfate. This was concentrated under reduced pressure to obtain a crude product of the entitled compound (4.2 g).

PRODUCTION EXAMPLE 47-2

Ethyl 4-oxohexanoate

Concentrated sulfuric acid (1.0 mL) was added to an ethanol solution (10 mL) of the compound (4.2 g) obtained in Production Example 47-1 at room temperature. After stirred with heating under reflux for 6 hours, the reaction liquid was poured into aqueous saturated sodium hydrogencarbonate solution. The resulting mixture was extracted with diethyl ether, and then the organic layer was dried with sodium sulfate. This was concentrated under reduced pressure, and the residue was purified through reduced-pressure distillation (9 Torr, 89° C.) to obtain the entitled compound (2.4 g).

PRODUCTION EXAMPLE 47-3

Ethyl 5-bromo-4-oxohexanoate

Bromine (0.323 mL) was dropwise added to a diethyl ether solution (2 mL) of the compound (1.0 g) obtained in Production Example 47-2, at 0° C. After stirred for 1 hour, the reaction liquid was poured into aqueous saturated sodium hydrogencarbonate solution. The resulting mixture was extracted with diethyl ether, and the organic layer was washed with aqueous saturated sodium sulfite solution and saturated saline water. The organic layer was dried with sodium sulfate, and concentrated under reduced pressure to obtain a crude product of the entitled compound (1.5 g).

PRODUCTION EXAMPLE 47-4

Ethyl 5-[2-{[(4-methylphenyl)sulfonyl]imino}-5-nitropyridin-1(2H)-yl]-4-oxohexanoate, and ethyl (2E)-5-[2-{[(4-methylphenyl)sulfonyl]imino}-5-nitropyridin-1(2H)-yl]-4-oxohexen-2-oate Diisopropylethylamine (0.838 mL) was added to a DMF solution (10 mL) of the crude product (1.5 g) obtained in Production Example 47-3 and the compound (1.32 g) obtained in Production Example 38-3, at room temperature. After stirred at that temperature for 12 hours, the reaction liquid was poured into water. The resulting mixture was extracted with ethyl acetate, the organic layer was washed with saturated saline water, and dried with sodium sulfate. This was concentrated under reduced pressure, and the residue was purified through silica gel column chromatography (ethyl acetate/chloroform/hexane=1/1/1 to 2/2/1) to obtain ethyl 5-[2-{[(4-methylphenyl)sulfonyl]imino}-5-nitropyridin-1(2H)-yl]-4-oxohexanoate (635 mg) and ethyl(2E)-5-[2-

{[(4-methylphenyl)sulfonyl]imino}-5-nitropyridin-1(2H)-yl]-4-oxohexen-2-oate (550 mg).

PRODUCTION EXAMPLE 47-5

Ethyl 3-(3-methyl-6-nitroimidazo[1,2-a]pyridin-2-yl)propionate

Trifluoroacetic anhydride (3 mL) was added to a dichloromethane solution (6 mL) of ethyl 5-[2-{[(4-methylphenyl)sulfonyl]imino}-5-nitropyridin-1(2H)-yl]-4-oxohexanoate (635 mg) obtained in Production Example 47-4, at room temperature. The reaction liquid was heated up to 40° C., stirred for 6 hours, and then concentrated under reduced pressure. Aqueous saturated sodium hydrogencarbonate solution was added to the residue, and extracted with ethyl acetate. The organic layer was dried with sodium sulfate, concentrated under reduced pressure, and the residue was purified through silica gel column chromatography (ethyl acetate/chloroform/hexane=1/1/1) to obtain the entitled compound (328 mg).

PRODUCTION EXAMPLE 47-6

Ethyl 3-(3-methyl-6-{[4-(pyridin-2-ylmethoxy)benzoyl]amino}imidazo[1,2-a]pyridin-2-yl)propionate 10% palladium-carbon (20 mg) was added to a methanol/THF mixed solution (1/1, 6 mL) of the compound (50 mg) obtained in Production Example 47-5, in a nitrogen atmosphere at room temperature. This was stirred in a hydrogen atmosphere (1 atm) at room temperature for 1 hour, and then the catalyst was removed through filtration. The filtrate was concentrated under reduced pressure, and dried under reduced pressure. Thus obtained, ethyl 3-(6-amino-3-methylimidazo[1,2-a]pyridin-2-yl)propionate dihydrochloride and the compound (41.3 mg) obtained in Production Example 3-2 were processed in the same manner as in Example 1 to obtain the entitled compound (46.3 mg).

PRODUCTION EXAMPLE 47-7

Ethyl(2E)-3-[3-methyl-6-nitroimidazo[1,2-a]pyridin-2-yl]acrylate

Ethyl(2E)-5-[2-{[(4-methylphenyl)sulfonyl]imino}-5-nitropyridin-1(2H)-yl]-4-oxohexen-2-oate (550 mg) obtained in Production Example 47-4 was processed in the same manner as in Production Example 47-5 to obtain the entitled compound (231 mg).

PRODUCTION EXAMPLE 47-8

Ethyl(2E)-3-[3-methyl-6-{[4-(pyridin-2-ylmethoxy)benzoyl]amino}imidazo[1,2-a]pyridin-2-yl]acrylate The compound (70 mg) obtained in Production Example 47-7 was suspended in methanol/water mixed solvent (1/1, 4 mL), and iron powder (83.8 mg) and ammonium chloride (160 mg) were added thereto at room temperature. This was heated up to 90° C. and stirred for 4 hours, the insoluble matter was removed through filtration, and the filtrate was concentrated under reduced pressure. Aqueous saturated sodium hydrogencarbonate solution was added to the residue, and extracted with chloroform. The organic layer was dried with sodium sulfate, and then concentrated under reduced pressure. Thus obtained, (2E)-3-(6-amino-3-methylimidazo[1,2-a]pyridin-2-yl)prop-2-en-1-ol hydrochloride and the compound (83.8 mg) obtained in Production Example 3-2 were processed in the same manner as in Example 1 to obtain the entitled compound (94.5 mg).

PRODUCTION EXAMPLE 48-1

N-(2-formyl-3-methylimidazo[1,2-a]pyridin-6-yl)acetamide

Sulfur trioxide/pyridine complex (1.97 g) was added to a mixture of the compound (906 mg) obtained in Production Example 46-2, triethylamine (3.45 mL) and DMSO (10 mL) at room temperature and stirred for 15 hours. The reaction liquid was poured into water, and extracted with chloroform. The organic layer was dried with sodium sulfate, and concentrated under reduced pressure. The residue was purified through silica gel chromatography (methanol/chloroform=1/50 to 1/20) to obtain the entitled compound (262 mg).

PRODUCTION EXAMPLE 48-2

Ethyl(2E)-3-[6-(acetylamino)-3-methylimidazo[1,2-a]pyridin-2-yl]acrylate

Ethyl diethylphosphonoacetate was dropwise added to a THF suspension (8 mL) of 60% sodium hydride (960 mg) at 0° C. This was stirred at that temperature for 30 minutes, and a DMF solution (2 mL) of the compound (262 mg) obtained in Production Example 48-1 was dropwise added to the reaction liquid at 0° C. After stirred for 4 hours, the reaction liquid was poured into water, and extracted with chloroform. The organic layer was dried with sodium sulfate, and concentrated under reduced pressure. The residue was purified through silica gel chromatography (methanol/chloroform/ethyl acetate=1/20/20 to 1/5/5) to obtain the entitled compound (153 mg).

PRODUCTION EXAMPLE 48-3

Ethyl 3-[6-(acetylamino)-3-methylimidazo[1,2-a]pyridin-2-yl]propionate

Sodium borohydride (54.5 mg) and nickel chloride 6-hydrate (25.2 mg) were added in that order to a methanol solution (4 mL) of the compound (153 mg) obtained in Production Example 48-2, at 0° C. The ice bath was removed, and this was stirred for 6 hours, and water was added to the reaction liquid. This was extracted with chloroform, and the organic layer was dried with sodium sulfate. This was concentrated under reduced pressure to obtain a crude product of the entitled compound (150 mg).

PRODUCTION EXAMPLE 48-4

N-[2-(3-hydoxypropyl)-3-methylimidazo[1,2-a]pyridin-6-yl]acetamide

A toluene solution (2.65 mL) of 1.0 M diisobutylaluminium hydride was dropwise added to a THF solution (4 mL) of the crude product (150 mg) obtained in Production Example 48-3, at 0° C. The ice bath was removed, and this was stirred for 8 hours, then sodium sulfate 10-hydrate was added thereto and further stirred for 1 hour. The insoluble matter was removed through filtration, and the filtrate was concentrated under reduced pressure. The residue was purified through silica gel chromatography (methanol/chloroform=1/100 to 1/30) to obtain the entitled compound (38.5 mg).

PRODUCTION EXAMPLE 48-5

N-[3-methyl-2-(3-pyrrolidin-1-ylpropyl)imidazo[1,2-a]pyridin-6-yl]acetamide

The compound (38.5 mg) obtained in Production Example 48-4 was processed in the same manner as in Production Example 46-3 to obtain the entitled compound (13.4 mg).

PRODUCTION EXAMPLE 49-1

2-(Methoxymethyl)-3-methyl-6-nitroimidazo[1,2-a]pyridine 2,3-Dimethyl-6-nitroimidazo[1,2-a]pyridine (1.5 g) produced according to JP-A 2003-207632 was dissolved in chloroform (50 mL), and N-bromosuccinimide (hereafter abbreviated as "NBS") was added thereto and stirred at room temperature for 1 hour. The reaction liquid was concentrated, dissolved in methanol (50 mL), and at 0° C., a methanol solution (2.0 mL) of 25% sodium methoxide was added thereto, and stirred at room temperature for 30 minutes. The reaction liquid was concentrated, diluted with ethyl acetate, and washed with aqueous saturated ammonium chloride solution and saturated saline water in that order. This was dried with anhydrous sodium sulfate, and the solvent was evaporated off under reduced pressure. The resulting residue was purified through silica gel column chromatography (hexane/ethyl acetate=3/1 to 1/3) to obtain the entitled compound (696 mg) as a yellow solid.

PRODUCTION EXAMPLE 49-2

2-(Methoxymethyl)-3-methylimidazo[1,2-a]pyridin-6-ylamine dihydrochloride

The compound obtained in Production Example 49-1 was processed in the same manner as in Production Example 38-6 to obtain the entitled compound.

EXAMPLE 1

4-(6-Chloropyridin-3-ylmethoxy)-N-(2-cyclopropyl-3-methylimidazo[1,2-a]pyridin-6-yl)benzamide The compound (50 mg) obtained in Production Example 1-2, HATU (79 mg) and diisopropylethylamine (232 μL) were added to a DMF solution (1 mL) of the compound (50 mg) obtained in Production Example 41-1, and stirred at room temperature for 2 hours. Chloroform/methanol (10/1) mixed solution (15 mL) was added to the reaction solution, and the chloroform layer was washed with water and aqueous saturated sodium chloride solution in that order. The chloroform layer was dried with anhydrous magnesium sulfate, the solvent was evaporated off under reduced pressure, and the resulting residue was purified through silica gel column chromatography (chloroform/methanol=40/1 to 9/1) to obtain the entitled compound (30.8 mg).
$^1$H-NMR (400 MHz, DMSO-d$_6$, δ ppm): 0.87-0.89 (4H, m), 2.04-2.07 (1H, m), 2.46 (3H, s), 5.27 (2H, s), 7.19 (2H, d, J=8.8 Hz), 7.38-7.39 (2H, m), 7.59 (1H, d, J=8.3 Hz), 7.98-8.00 (3H, m), 8.56 (1H, d, J=2.4 Hz), 8.86 (1H, s), 10.18 (1H, s) ESI-MS Found: m/z 433 [M+H]$^+$

EXAMPLE 2

4-(5-Chloropyridin-2-ylmethoxy)-N-[3-methyl-2-(2-trans-methylcyclopropyl)imidazo[1,2-a]pyridin-6-yl]benzamide The compound (46 mg) obtained in Production Example 38-6 and the compound (52.5 mg) obtained in Production Example 2-4 were processed in the same manner as in Example 1 to obtain the entitled compound (37.4 mg) as a brown solid.
$^1$H-NMR (400 MHz, CD$_3$OD, δ ppm): 0.73-0.80 (m, 1H), 1.10-1.17 (m, 1H), 1.24 (d, J=6.3 Hz, 3H), 1.27-1.38 (m, 1H), 1.70-1.78 (m, 1H), 2.52 (s, 3H), 5.28 (s, 2H), 7.16 (d, 2H, J=9.2 Hz), 7.37 (dd, J=9.4, 1.7 Hz, 1H), 7.40 (dd, J=9.6, 1.2 Hz, 1H), 7.62 (d, J=8.6 Hz, 1H), 7.92 (dd, J=8.4, 2.3 Hz, 1H), 7.98 (d, J=8.9 Hz, 2H), 8.58 (d, J=1.8 Hz, 1H), 8.87 (s, 1H) ESI-MS Found: m/z 447 [M+H]$^+$

EXAMPLE 3

N-[2-(3-trans-methoxycyclobutyl)-3-methylimidazo[1,2-a]pyridin-6-yl]-4-(pyridin-2-ylmethoxy)benzamide The compound (57.1 mg) obtained in Production Example 43-9 and the compound (50.1 mg) obtained in Production Example 3-2 were processed in the same manner as in Example 1 to obtain the entitled compound (42.3 mg) as a white solid.
$^1$H-NMR (400 MHz, DMSO-d$_6$, δ ppm): 2.27-2.28 (2H, m), 2.34 (3H, s), 2.39-2.46 (2H, m), 3.19 (3H, s), 3.61-3.65 (1H, m), 4.27-4.31 (1H, m), 5.29 (2H, s), 7.19 (2H, d, J=9.1 Hz), 7.35-7.42 (2H, m), 7.51-7.56 (2H, m), 7.86 (1H, td, J=7.8, 1.8 Hz), 7.98 (2H, d, J=9.1 Hz), 8.60 (1H, ddd, J=4.0, 1.8, 1.0 Hz), 8.87 (1H, d, J=1.0 Hz), 10.20 (1H, s) ESI-MS Found: m/z 443 [M+H]$^+$

EXAMPLE 4

5-Benzyloxypyridine-2-carboxylic acid(2-cyclopropyl-3-methylimidazo[1,2-a]pyridin-6-yl)amide The compound (53 mg) obtained in Production Example 41-1 and the compound (46 mg) obtained in Production Example 4-3 were processed in the same manner as in Example 1 to obtain the entitled compound (67.7 mg).
$^1$H-NMR (400 MHz, DMSO-d$_6$, δ ppm): 0.88-0.89 (4H, m), 2.04-2.08 (1H, m), 2.46 (3H, s), 5.32 (2H, s), 7.41-7.43 (4H, m), 7.52-7.53 (2H, m), 7.59 (1H, dd, J=9.4, 2.0 Hz), 7.73 (1H, dd, J=8.8, 2.9 Hz), 8.15 (1H, d, J=8.6 Hz), 8.47 (1H, d, J=2.3 Hz), 8.98 (1H, d, J=1.2 Hz), 10.63 (1H, s).

EXAMPLE 5

4-Benzyloxy-N-(2-(cyclopropyl-3-methylimidazo[1,2-a]pyridin-6-yl)benzamide trifluoroacetate The compound (15 mg) obtained in Production Example 41-1 and 4-benzyloxybenzenecarboxylic acid (13.2 mg) were processed in the same manner as in Example 1, and the resulting product was purified through reversed-phase HPLC (YMC-Pack ODS-AQ, acetonitrile/water (0.1% TFA) (10/90 to 90/10)) to obtain the entitled compound (13.2 mg).
$^1$H-NMR (400 MHz, DMSO-d$_6$, δ ppm): 0.95-0.99 (2H, m), 1.10-1.15 (2H, m), 2.26 (1H, m), 2.56 (3H, s), 5.23 (2H, s), 7.20 (2H, d, J=9.3 Hz), 7.35-7.42 (3H, m), 7.49 (2H, d, J=7.3 Hz), 7.8 (1H, d, J=9.3 Hz), 8.00-8.03 (3H, m), 9.23 (1H, s), 10.59 (1H, s)

EXAMPLE 6

4-(5-Fluoropyridin-2-ylmethoxy)-N-(2-isopropyl-3-methylimidazo[1,2-a]pyridin-6-yl)benzamide The compound (68 mg) obtained in Production Example 40-4 and the compound (49 mg) obtained in Production Example 5-5 were processed in the same manner as in Example 1 to obtain the entitled compound (79 mg).
$^1$H-NMR (400 MHz, DMSO-$d_6$, δ ppm): 1.25 (6H, d, J=6.8 Hz), 2.39 (3H, s), 3.13-3.14 (1H, m), 5.29 (2H, s), 7.19 (2H, d, J=8.8 Hz), 7.38 (1H, dd, J=9.8, 2.0 Hz), 7.47-7.49 (1H, m), 7.65 (1H, dd, J=4.4, 2.2 Hz), 7.80 (1H, td, J=8.8, 2.9 Hz), 8.00 (2H, d, J=8.8 Hz), 8.61 (1H, d, J=2.9 Hz), 8.89 (1H, s), 10.19 (1H, s)

EXAMPLE 7

4-(3-Fluoropyridin-2-ylmethoxy)-N-[3-methyl-2-(tetrahydrofuran-3-yl)imidazo[1,2-a]pyridin-6-yl]benzamide The compound (35 mg) obtained in Production Example 42-1 and the compound (30 mg) obtained in Production Example 6-4 were processed in the same manner as in Example 1 to obtain the entitled compound (38.2 mg).
$^1$H-NMR (400 MHz, DMSO-$d_6$, δ ppm): 2.19-2.23 (2H, m), 2.42 (3H, s), 3.59-3.61 (1H, m), 3.69-3.71 (1H, m), 3.83-3.85 (1H, m), 3.92-3.96 (1H, m), 4.03-4.05 (1H, m), 5.35 (2H, brs), 7.20 (2H, d, J=8.8 Hz), 7.42 (1H, dd, J=9.3, 2.0 Hz), 7.49-7.57 (2H, m), 7.81-7.84 (1H, m), 7.99 (2H, d, J=9.3 Hz), 8.48-8.48 (1H, m), 8.91 (1H, s), 10.21 (1H, s)

EXAMPLE 8

N-(2-ethyl-3-methylimidazo[1,2-a]pyridin-6-yl)-4-(6-fluoropyridin-2-ylmethoxy)benzamide The compound (50 mg) obtained in Production Example 39-4 and the compound (55 mg) obtained in Production Example 7-5 were processed in the same manner as in Example 1 to obtain the entitled compound (35.4 mg).
$^1$H-NMR (400 MHz, DMSO-$d_6$, δ ppm): 1.22 (3H, t, J=7.6 Hz), 2.38 (3H, s), 2.68 (2H, q, J=7.5 Hz), 5.26 (2H, s), 7.17-7.19 (3H, m), 7.38-7.52 (3H, m), 7.99-8.07 (3H, m), 8.89 (1H, s), 10.21 (1H, s)

EXAMPLE 9

N-(2-ethyl-3-methylimidazo[1,2-a]pyridin-6-yl)-3-fluoro-4-(pyridin-2-ylmethoxy)benzamide The compound (64 mg) obtained in Production Example 39-4 and the compound (64 mg) obtained in Production Example 8-3 were processed in the same manner as in Example 1 to obtain the entitled compound (53 mg) as a white brown solid.
$^1$H-NMR (400 MHz, DMSO-$d_6$, δ ppm): 1.24 (3H, t, J=7.6 Hz), 2.40 (3H, s), 2.70 (2H, q, J=7.6 Hz), 5.39 (2H, s), 7.38-7.52 (4H, m), 7.58 (1H, d), 7.82-7.96 (3H, m), 8.60-8.66 (1H, m), 8.88-8.92 (1H, m), 10.27 (1H, s) ESI-MS Found: m/z 405 [M+H]$^+$

EXAMPLE 10

N-(2-cyclopropyl-3-methylimidazo[1,2-a]pyridin-6-yl)-2-fluoro-4-(pyridin-2-ylmethoxy)benzamide The compound (32 mg) obtained in Production Example 41-1 and the compound (30 mg) obtained in Production Example 9-2 were processed in the same manner as in Example 1 to obtain the entitled compound (23.1 mg).
$^1$H-NMR (400 MHz, CDCl$_3$, δ ppm): 0.94-1.06 (4H, m), 1.95-2.02 (1H, m), 2.51 (3H, s), 5.27 (2H, s), 6.81-6.86 (2H, m), 6.96 (1H, dd, J=8.8, 2.4 Hz), 7.27-7.29 (1H, m), 7.46-7.49 (2H, m), 7.74-7.76 (1H, m), 8.13 (1H, t, J=9.3 Hz), 8.31 (1H, d, J=17.1 Hz), 8.63 (1H, d, J=3.9 Hz), 8.95 (1H, s)

EXAMPLE 11

N-(2-ethyl-3-methylimidazo[1,2-a]pyridin-6-yl)-3-fluoro-4-[(5-fluoropyridin-2-yl)methoxy]benzamide The compound (64 mg) obtained in Production Example 39-4 and the compound (64 mg) obtained in Production Example T-2 were processed in the same manner as in Example 1 to obtain the entitled compound (53 mg) as a pale orange substance.
$^1$H-NMR (400 MHz, DMSO-$d_6$, δ ppm): 1.22 (3H, t, J=7.6 Hz), 2.38 (3H, s), 2.68 (2H, q, J=7.6 Hz), 5.36 (2H, s), 7.36-7.52 (3H, m), 7.62-7.70 (1H, m), 7.78-7.94 (3H, m), 8.60-8.64 (1H, m), 8.84-8.90 (1H, m), 10.3 (1H, s) ESI-MS Found: m/z 423 [M+H]$^+$

EXAMPLE 12

5-[(5-chloropyridin-2-yl)methoxy]-N-(2-cyclopropyl-3-methylimidazo[1,2-a]pyridin-6-yl)pyridine-2-carboxamide The compound (31.5 mg) obtained in Production Example 41-1 and the compound (30 mg) obtained in Production Example 10-2 were processed in the same manner as in Example 1 to obtain the entitled compound (48 mg).
$^1$H-NMR (400 MHz, CDCl$_3$, δ ppm): 0.94-1.07 (4H, m), 1.97-2.01 (1H, m), 2.52 (3H, s), 5.30 (2H, s), 6.99 (1H, dd, J=9.3, 2.0 Hz), 7.44-7.48 (3H, m), 7.74 (1H, dd, J=8.3, 2.4 Hz), 8.23 (1H, d, J=8.3 Hz), 8.37 (1H, d, J=2.4 Hz), 8.60 (1H, d, J=2.0 Hz), 9.03 (1H, brs), 9.72 (1H, s)

EXAMPLE 13

4-(Benzyloxy)-N-[3-methyl-2-(pyrrolidin-1-ylmethyl)imidazo[1,2-a]pyridin-6-yl)]benzamide The compound (30 mg) obtained in Production Example 46-3 was dissolved in hydrochloric acid-methanol solution (4 mL), stirred at 80° C. for 4 hours, and then concentrated under reduced pressure. Thus obtained, 3-methyl-2-(pyrrolidin-1-ylmethyl)imidazo[1,2-a]pyridin-6-ylamine dihydrochloride and 4-benzyloxybenzenecarboxylic acid (25.1 mg) were processed in the same manner as in Example 1 to obtain the entitled compound (36.1 mg).
$^1$H-NMR (400 MHz, CDCl$_3$, δ ppm): 1.78-1.75 (4H, m), 2.49 (3H, s), 2.61-2.60 (4H, m), 3.80 (2H, s), 6.92 (1H, d, J=9.6 Hz), 7.08-7.05 (4H, m), 7.20 (1H, t, J=7.4 Hz), 7.40 (2H, t, J=8.0 Hz), 7.50 (1H, d, J=9.6 Hz), 7.80 (1H, s), 7.86 (2H, d, J=8.6 Hz), 8.96 (1H, s) ESI-MS Found: m/z 441 [M+H]$^+$

EXAMPLE 14

N-[2-(3-hydroxypropyl)-3-methylimidazo[1,2-a]pyridin-6-yl]-4-(pyridin-2-ylmethoxy)benzamide Lithiumaluminium hydride (250 mg) was added to a THF suspension (10 mL) of the compound (46.3 mg) obtained in Production Example 47-6 in a nitrogen atmosphere at 0° C. This was stirred at 0° C. for 3 hours and then at room temperature for 2 hours, sodium sulfite 10-hydrate was added thereto, and further stirred for 1 hour. The insoluble matter was separated through filtration, and the filtrate was concentrated under reduced pressure. The residue was purified through silica gel chromatography (methanol/chloroform=1/30) to obtain the entitled compound (41.0 mg).

$^1$H-NMR (400 MHz, CD$_3$OD, δ ppm): 1.99-1.92 (2H, m), 2.49 (3H, s), 2.85 (2H, t, J=7.6 Hz), 3.61 (2H, t, J=6.4 Hz), 5.31 (2H, s), 7.19 (2H, dd, J=6.8, 2.1 Hz), 7.44-7.40 (2H, m), 7.47 (1H, dd, J=9.8, 1.0 Hz), 7.65 (1H, d, J=7.7 Hz), 7.92 (1H, td, J=7.7, 1.8 Hz), 8.00 (2H, dd, J=6.8, 2.1 Hz), 8.59 (1H, dq, J=4.3, 1.0 Hz), 8.91 (1H, s) ESI-MS Found: m/z 417 [M+H]$^+$

EXAMPLE 15

N-{2-[(1E)-3-hydroxyprop-1-en-1-yl]-3-methylimidazo[1,2-a]pyridin-6-yl}-4-(pyridin-2-ylmethoxy)benzamide A toluene solution (0.44 mL) of 1.0 M diisobutylaluminium hydride was dropwise added to a THF solution (4 mL) of the compound (40.0 mg) obtained in Production Example 47-8 at 0° C. This was stirred at room temperature for 1 hour, sodium sulfate 10-hydrate was added thereto, and further stirred for 1 hour. The insoluble matter was separated through filtration, and the filtrate was concentrated under reduced pressure. The residue was purified through silica gel chromatography (methanol/chloroform=1/20 to 1/8) to obtain the entitled compound (10.8 mg).

$^1$H-NMR (400 MHz, DMSO-d$_6$, δ ppm): 2.41 (3H, s), 4.12-4.11 (2H, m), 4.81 (1H, t, J=5.5 Hz), 5.26 (2H, s), 6.56-6.51 (1H, m), 6.66 (1H, d, J=15.5 Hz), 7.15 (2H, d, J=8.8 Hz), 7.34 (1H, t, J=5.5 Hz), 7.40 (1H, dt, J=9.8, 2.0 Hz), 7.45 (1H, d, J=9.8 Hz), 7.51 (1H, d, J=7.7 Hz), 7.82 (1H, td, J=7.7, 2.0 Hz), 7.95 (2H, d, J=8.8 Hz), 8.57 (1H, d, J=5.5 Hz), 8.88 (1H, s), 10.18 (1H, s) ESI-MS Found: m/z 415 [M+H]$^+$

EXAMPLE 16

N-[2-(3-hydroxy-3-methylbutyl)-3-methylimidazo[1,2-a]pyridin-6-yl]-4-(pyridin-2-ylmethoxy)benzamide A THF solution (1.3 mL) of 1.0 M methylmagnesium bromide was dropwise added to a THF solution (10 mL) of the compound (30.0 mg) obtained in Production Example 47-6 at 0° C. The ice bath was removed, and this was stirred for 2 hours, and then the reaction liquid was poured into aqueous saturated sodium hydrogencarbonate solution. The resulting mixture was extracted with chloroform, the organic layer was dried with sodium sulfate, and then concentrated under reduced pressure. The residue was purified through NH silica gel chromatography (methanol/chloroform=1/70 to 1/50) to obtain the entitled compound (3.3 mg).

$^1$H-NMR (400 MHz, CDCl$_3$, δ ppm): 1.30 (6H, s), 1.93 (2H, t, J=7.1 Hz), 2.41 (3H, s), 2.89 (2H, t, J=7.1 Hz), 5.27 (2H, s), 6.92 (1H, dd, J=9.4, 1.8 Hz), 7.07 (2H, d, J=9.0 Hz), 7.25 (1H, t, J=6.0 Hz), 7.40 (1H, d, J=9.4 Hz), 7.50 (1H, d, J=7.7 Hz), 7.73 (1H, td, J=7.7, 1.8 Hz), 7.86 (2H, d, J=9.0 Hz), 7.91 (1H, s), 8.61 (1H, d, J=6.0 Hz), 8.91 (1H, s) ESI-MS Found: m/z 445 [M+H]$^+$

EXAMPLE 17

4-(Benzyloxy)-N-[3-methyl-2-(3-pyrrolidin-1-ylpropyl)imidazo[1,2-a]pyridin-6-yl)]benzamide The compound (13.4 mg) obtained in Production Example 48-5 and 4-benzyloxybenzenecarboxylic acid (10.3 mg) were processed in the same manner as in Example 13 to obtain the entitled compound (8.8 mg).

$^1$H-NMR (400 MHz, CDCl$_3$, δ ppm): 1.81-1.78 (4H, m), 2.01-1.93 (2H, m), 2.44 (3H, s), 2.53-2.51 (6H, m), 2.81 (2H, t, J=7.8 Hz), 5.16 (2H, s), 6.93 (1H, dd, J=9.4, 2.0 Hz), 7.08 (2H, dt, J=9.4, 2.5 Hz), 7.50-7.35 (6H, m), 7.90-7.87 (3H, m), 8.94 (1H, d, J=1.2 Hz) ESI-MS Found: m/z 469 [M+H]$^+$

EXAMPLE 18

N-[3-methyl-2-(3-pyrrolidin-1-ylpropyl)imidazo[1,2-a]pyridin-6-yl]-4-(pyridin-2-ylmethoxy)benzamide The compound (26.3 mg) obtained in Example 14 was processed in the same manner as in Production Example 46-3 to obtain the entitled compound (4.7 mg).

$^1$H-NMR (400 MHz, CDCl$_3$, δ ppm): 2.03-1.80 (6H, m), 2.58-2.55 (6H, m), 2.44 (3H, s), 2.81 (2H, t, J=7.6 Hz), 5.30 (2H, s), 6.94 (1H, d, J=9.4 Hz), 7.11 (2H, dd, J=6.8, 2.4 Hz), 7.30-7.26 (1H, m), 7.54-7.49 (2H, m), 7.76 (1H, td, J=7.6, 1.6 Hz), 7.84 (1H, brs), 7.88 (2H, dt, J=9.4, 2.4 Hz), 8.64 (1H, d, J=4.7 Hz), 8.93 (1H, s). ESI-MS Found: m/z 470 [M+H]$^+$

EXAMPLE 19

N-(2-{3-[(3S)-3-fluoropyrrolidin-1-yl]propyl}-3-methylimidazo[1,2-a]pyridin-2-ylmethoxy)benzamide (1) Triethylamine (87.9 μL) and sulfur trioxide-pyridine complex (46.3 mg) were added to a DMSO solution (3 mL) of the compound (20.0 mg) obtained in Example 14, at room temperature. After stirred for 11 hours, the reaction liquid was poured into saturated saline water, and extracted with chloroform. The organic layer was dried with sodium sulfate, and concentrated under reduced pressure. The residue was purified through silica gel chromatography (methanol/chloroform=1/25 to 1/8) to obtain N-[3-methyl-2-(3-oxopropyl)imidazo[1,2-a]pyridin-6-yl]-4-(pyridin-2-ylmethoxy)benzamide (10.8 mg).

(2) Diisopropylethylamine (5.2 μL) was added to a methanol solution (2.0 mL) of (S)-2-fluoropyridine hydrochloride (3.9 mg) at room temperature. This was stirred for 30 minutes, and a methanol solution (4 mL) of the compound (10.8 mg) obtained in the above, zinc chloride (0.7 mg) and sodium cyanotrihydroborate (2.6 mg) were added thereto in that order at room temperature. After stirred for 24 hours, the reaction liquid was poured into water, and extracted with chloroform. The organic layer was dried with sodium sulfate, and concentrated under reduced pressure. The residue was purified through NH silica gel chromatography (methanol/chloroform=1/60) to obtain the entitled compound (7.2 mg).

$^1$H-NMR (400 MHz, CDCl$_3$, δ ppm): 2.15-1.91 (4H, m), 2.42-2.36 (4H, m), 2.52 (2H, t, J=7.4 Hz), 2.91-2.62 (5H, m), 5.23-5.06 (1H, m), 5.27 (2H, s), 6.91 (1H, dd, J=9.4, 1.7 Hz), 7.07 (2H, d, J=9.0 Hz), 7.27-7.23 (1H, m), 7.47 (1H, d, J=9.4

Hz), 7.50 (1H, d, J=7.8 Hz), 7.73 (1H, td, J=7.8, 1.7 Hz), 7.87-7.84 (3H, m), 8.61 (1H, d, J=4.3 Hz), 8.91 (1H, s) ESI-MS Found: m/z 488 [M+H]$^+$

EXAMPLE 20

N-{2-[3-(3,3-difluoropyrrolidin-1-yl)propyl]-3-methylimidazo[1,2-a]pyridin-6-yl}-4-(pyridin-2-ylmethoxy)benzamide The compound (25.0 mg) obtained in Example 14 and 3,3-difluoropyrrolidine (3.4 mg) were processed in the same manner as in Example 19 to obtain the entitled compound (5.9 mg).
$^1$H-NMR (400 MHz, CDCl$_3$, δ ppm): 1.95-1.88 (2H, m), 2.28-2.20 (2H, m), 2.41 (3H, s), 2.48 (2H, t, J=7.2 Hz), 2.70 (2H, t, J=7.0 Hz), 2.78 (2H, t, J=7.4 Hz), 2.86 (2H, t, J=13.3 Hz), 5.27 (2H, s), 6.92 (1H, d, J=9.4 Hz), 7.07 (2H, d, J=8.6 Hz), 7.27-7.24 (1H, m), 7.52-7.46 (2H, m), 7.73 (1H, td, J=7.7, 1.4 Hz), 7.87-7.85 (3H, m), 8.61 (1H, d, J=5.1 Hz), 8.92 (1H, s) ESI-MS Found: m/z 506 [M+H]$^+$

EXAMPLE 21

N-[3-methyl-2-(3-morpholin-4-ylpropyl)imidazo[1,2-a]pyridin-6-yl]-4-(pyridin-2-ylmethoxy)benzamide The compound (20.0 mg) obtained in Example 14 and morpholine (1 mL) were processed in the same manner as in Production Example 46-3 to obtain the entitled compound (13.0 mg).
$^1$H-NMR (400 MHz, solvent, δ ppm): 1.96-1.89 (2H, m), 2.49-2.36 (9H, m), 2.77 (2H, t, J=7.6 Hz), 3.71-3.67 (4H, m), 5.27 (2H, s), 6.90 (1H, d, J=9.8 Hz), 7.07 (2H, d, J=8.6 Hz), 7.26-7.25 (1H, m), 7.49 (2H, dd, J=12.1, 8.6 Hz), 7.73 (1H, td, J=7.6, 1.6 Hz), 7.87-7.80 (3H, m), 8.61 (1H, d, J=5.1 Hz), 8.92 (1H, s) ESI-MS Found: m/z 486 [M+H]$^+$

EXAMPLE 22

N-{3-methyl-2-[3-(1H-pyrazol-1-yl)propyl]imidazo[1,2-a]pyridin-6-yl}-4-(pyridin-2-ylmethoxy)benzamide Triethylamine (33.4 μL) and methanesulfonyl chloride (7.0 μL) were added to a THF solution (8 mL) of the compound (25 mg) obtained in Example 14, at room temperature. After stirred for 1 hour, the reaction liquid was poured into aqueous saturated sodium hydrogencarbonate solution. The resulting mixture was extracted with chloroform, and the organic layer was washed with saturated saline water and dried with sodium sulfate. This was concentrated under reduced pressure, and the residue was dissolved in THF (4 mL). The solution was dropwise added to a THF solution (2 mL) of pyrazole (5.3 mg) and 60% sodium hydride (3.1 mg) at 0° C. This was heated up to 60° C. and stirred for 10 hours, and then the reaction liquid was poured into water. The resulting mixture was extracted with chloroform, and the organic layer was washed with saturated saline water and dried with sodium sulfate. This was concentrated under reduced pressure, and the residue was purified through NH silica gel chromatography (methanol/chloroform=1/60) to obtain the entitled compound (3.4 mg).
$^1$H-NMR (400 MHz, CDCl$_3$, δ ppm): 2.40-2.33 (5H, m), 2.75 (2H, t, J=7.4 Hz), 4.21 (2H, t, J=6.8 Hz), 5.30 (2H, s), 6.25 (1H, t, J=2.0 Hz), 6.96 (1H, dd, J=9.8, 2.0 Hz), 7.11 (2H, dd, J=11.7, 3.1 Hz), 7.28 (1H, t, J=6.1 Hz), 7.41 (1H, d, J=2.0 Hz), 7.52 (3H, dd, J=7.9, 6.1 Hz), 7.76 (1H, td, J=7.9, 2.0 Hz), 7.84 (1H, s), 7.90-7.87 (2H, m), 8.64 (1H, dd, J=3.8, 0.8 Hz), 8.95 (1H, s) ESI-MS Found: m/z 467 [M+H]$^+$

EXAMPLE 23

N-[3-methyl-2-(tetrahydrofuran-3-yl)imidazo[1,2-a]pyridin-6-yl]-4-(1-pyridin-2-ylethoxy)benzamide The compound (54.7 mg) obtained in Production Example 42-1 and the compound (50 mg) obtained in Production Example 11-3 were processed in the same manner as in Example 1 to obtain the entitled compound (52 mg).
$^1$H-NMR (400 MHz, DMSO-d$_6$, δ ppm): 1.64 (3H, d, J=6.4 Hz), 2.17-2.21 (2H, m), 2.40 (3H, s), 3.59-3.61 (1H, m), 3.68-3.70 (1H, m), 3.82-3.84 (1H, m), 3.93-3.95 (1H, m), 4.02-4.04 (1H, m), 5.61 (1H, q, J=6.4 Hz), 7.05 (2H, d, J=8.8 Hz), 7.30-7.32 (1H, m), 7.38 (1H, dd, J=9.8, 2.0 Hz), 7.45-7.48 (2H, m), 7.79-7.80 (1H, m), 7.89 (2H, d, J=8.8 Hz), 8.57-8.59 (1H, m), 8.88 (1H, s), 10.14 (1H, s)

EXAMPLE 24

N-(2-isopropyl-3-methylimidazo[1,2-a]pyridin-6-yl)-4-(5-methyl-[1,3,4]thiadiazol-2-ylmethoxy)benzamide The compound (11 mg) obtained in Production Example 40-4 and the compound (10 mg) obtained in Production Example 12-4 were processed in the same manner as in Example 1 to obtain the entitled compound (8 mg) as a white brown solid.
$^1$H-NMR (400 MHz, DMSO-d$_6$, δ ppm): 1.27 (6H, d, J=6.4 Hz), 2.41 (3H, s), 2.76 (3H, s), 3.15 (1H, septet, J=6.4 Hz), 5.68 (2H, s), 7.24 (2H, d, J=8.8 Hz), 7.40 (1H, d, J=9.6 Hz), 7.50 (1H, d, J=9.6 Hz), 8.02 (2H, d, J=8.8 Hz), 8.90 (1H, s), 10.24 (1H, s) ESI-MS Found: m/z 422 [M+H]$^+$

EXAMPLE 25

N-(2-cyclohexyl-3-methylimidazo[1,2-a]pyridin-6-yl)-4-(pyridin-2-yloxymethyl)benzamide The compound (40 mg) obtained in Production Example 41-1 and the compound obtained in Production Example 13-2 were processed in the same manner as in Example 1 to obtain the entitled compound (47 mg).
$^1$H-NMR (400 MHz, DMSO-d$_6$, δ ppm): 0.86-0.92 (4H, m), 2.04-2.08 (1H, m), 2.46 (3H, s), 5.46 (2H, s), 6.93 (1H, d, J=8.3 Hz), 7.01-7.02 (1H, m), 7.37-7.41 (2H, m), 7.60 (2H, d, J=8.3 Hz), 7.73-7.77 (1H, m), 7.99 (2H, d, J=8.3 Hz), 8.18-8.18 (1H, m), 8.89 (1H, s), 10.33 (1H, s)

EXAMPLE 26

N-(2-ethyl-3-methylimidazo[1,2-a]pyridin-6-yl)-4-(5-fluoropyrimidin-2-yloxymethyl)benzamide The compound (50 mg) obtained in Production Example 39-4 and the compound (50 mg) obtained in Production Example 14-2 were processed in the same manner as in Example 1 to obtain the entitled compound (33 mg) as a yellow solid.
$^1$H-NMR (400 MHz, CD$_3$OD, δ ppm): 1.41 (3H, t, J=7.6 Hz), 2.61 (3H, s), 2.96 (2H, q, J=7.6 Hz), 5.57 (2H, s), 7.70 (2H, d, J=8.8 Hz), 7.86 (1H, d, J=9.6 Hz), 8.06 (2H, d, J=8.8

Hz), 8.08 (1H, dd, J=8.8 Hz, 2.0 Hz), 8.60 (2H, s), 9.41 (1H, d, J=2.0 Hz) ESI-MS Found: m/z 406 [M+H]$^+$

EXAMPLE 27

N-(2-ethyl-3-methylimidazo[1,2-a]pyridin-6-yl)-3-fluoro-4-(pyridin-2-yloxymethyl)benzamide The compound (26 mg) obtained in Production Example 39-4 and the compound (26 mg) obtained in Production Example 15-3 were processed in the same manner as in Example 1 to obtain the entitled compound (16 mg) as a white brown solid.
$^1$H-NMR (400 MHz, CD$_3$OD, δ ppm): 1.41 (3H, t, J=7.6 Hz), 2.61 (3H, s), 2.96 (2H, q, J=7.6 Hz), 5.56 (2H, s), 6.90-6.98 (1H, m), 6.98-7.60 (1H, m), 7.70-7.90 (5H, m), 8.04-8.10 (1H, m), 8.14-8.22 (1H, m), 9.42 (1H, s) ESI-MS Found: m/z 405 [M+H]$^+$

EXAMPLE 28

N-(2-ethyl-3-methylimidazo[1,2-a]pyridin-6-yl)-4-((E)-2-phenylvinyl)benzamide

The compound (100 mg) obtained in Production Example 39-4 and 4-styrylbenzenecarboxylic acid (100 mg) were processed in the same manner as in Example 1 to obtain the entitled compound (100 mg).
$^1$H-NMR (400 MHz, CDCl$_3$, δ ppm): 1.33 (3H, t, J=7.7 Hz), 2.40 (3H, s), 2.78 (2H, q, J=7.7 Hz), 6.95 (1H, dd, J=9.4, 2.0 Hz), 7.14 (1H, d, J=16.2 Hz), 7.23 (1H, d, J=16.2 Hz), 7.31-7.41 (3H, m), 7.50 (1H, d, J=9.6 Hz), 7.54 (2H, d, J=7.5 Hz), 7.62 (2H, d, J=8.4 Hz), 7.89 (2H, d, J=8.4 Hz), 8.01 (1H, s), 8.98 (1H, s) ESI-MS Found: m/z 382 [M+H]$^+$

EXAMPLE 29

N-[3-methyl-2-(3-oxocyclobutyl)imidazo[1,2-a]pyridin-6-yl]-4-((E)-2-pyridin-2-ylvinyl)benzamide The compound (368 mg) obtained in Production Example 44-7 and the compound (338 mg) obtained in Production Example 17-2 were processed in the same manner as in Example 1 to obtain the entitled compound (404 mg) as a white solid.
$^1$H-NMR (400 MHz, DMSO-d$_6$, δ ppm): 2.45 (3H, s), 3.35-3.37 (2H, m), 3.42-3.45 (2H, m), 3.83-3.88 (1H, m), 7.29-7.32 (1H, m), 7.45-7.61 (4H, m), 7.75-7.84 (2H, m), 7.86 (2H, d, J=8.2 Hz), 8.04 (2H, d, J=8.2 Hz), 8.61 (1H, d, J=3.7 Hz), 8.97 (1H, s), 10.40 (1H, s) ESI-MS Found: m/z 423 [M+H]$^+$

EXAMPLE 30

N-[2-(3-hydroxy-3-methylcyclobutyl)-3-methylimidazo[1,2-a]pyridin-6-yl]-4-((E)-2-pyridin-2-ylvinyl)benzamide The compound (52 mg) obtained in Example 29 was dissolved in tetrahydrofuran (30 mL), and with cooling with ice, a THF solution (1 mL) of 1.0 M methylmagnesium bromide was added thereto. After 10 minutes, water was added to it, extracted with ethyl acetate, washed with saturated saline water, dried with anhydrous magnesium sulfate, and the solvent was evaporated off under reduced pressure. The resulting residue was purified through silica gel column chromatography (chloroform/methanol=30/1 to 15/1) to obtain the entitled compound (17.3 mg).
$^1$H-NMR (400 MHz, DMSO-d$_6$, δ ppm): 1.35 (3H, s), 2.24-2.39 (4H, m), 2.37 (3H, s), 3.16-3.17 (1H, m), 5.07 (1H, s), 7.27-7.31 (1H, m), 7.41-7.52 (3H, m), 7.59 (1H, d, J=8.0 Hz), 7.73-7.82 (2H, m), 7.84 (2H, d, J=8.4 Hz), 8.02 (2H, d, J=8.4 Hz), 8.60 (1H, d, J=4.9 Hz), 8.89 (1H, s), 10.35 (1H, s) ESI-MS Found: m/z 439 [M+H]$^+$

EXAMPLE 31

N-(2-ethyl-3-methylimidazo[1,2-a]pyridin-6-yl)-4-[(E)-2-(6-methylpyridin-2-yl)vinyl]benzamide The compound (50 mg) obtained in Production Example 39-4 and the compound (62 mg) obtained in Production Example 16-2 were processed in the same manner as in Example 1 to obtain the entitled compound (60.4 mg).
$^1$H-NMR (400 MHz, DMSO-d$_6$, δ ppm): 1.23 (3H, t, J=7.6 Hz), 2.39 (3H, s), 2.50 (3H, s), 2.69 (2H, q, J=7.5 Hz), 7.17 (1H, d, J=7.8 Hz), 7.41-7.47 (4H, m), 7.70-7.73 (2H, m), 7.85 (2H, d, J=8.3 Hz), 8.03 (2H, d, J=8.3 Hz), 8.92 (1H, s), 10.36 (1H, s)

EXAMPLE 32

3-Fluoro-N-[3-methyl-2-(tetrahydrofuran-3-yl)imidazo[1,2-a]pyridin-6-yl]-4-((E)-2-pyridin-2-ylvinyl)benzamide The compound (64 mg) obtained in Production Example 42-1 and the compound (64 mg) obtained in Production Example 18-3 were processed in the same manner as in Example 1 to obtain the entitled compound (53 mg) as a white brown solid.
$^1$H-NMR (400 MHz, CD$_3$OD, δ ppm): 2.26-2.42 (2H, m), 2.53 (3H, s), 3.68-3.80 (1H, m), 3.84-3.92 (1H, m), 3.94-4.04 (1H, m), 4.10-4.20 (2H, m), 7.30-7.40 (1H, m), 7.40-7.56 (3H, m), 7.64-7.72 (1H, m), 7.78-7.92 (4H, m), 7.92-8.00 (1H, m), 8.58-8.62 (1H, m), 8.99 (1H, s) ESI-MS Found: m/z 443 [M+H]$^+$

EXAMPLE 33

4-[(E)-2-(6-chloropyridin-3-yl)vinyl]-N-(2-ethyl-3-methylimidazo[1,2-a]pyridin-6-yl)benzamide The compound (191 mg) obtained in Production Example 39-4 and the compound (200 mg) obtained in Production Example T-4 were processed in the same manner as in Example 1 to obtain the entitled compound (113 mg) as a pale brown solid.
$^1$H-NMR (400 MHz, DMSO-d$_6$, δ ppm): 1.25 (3H, t, J=7.6 Hz), 2.41 (3H, s), 2.70 (2H, q, J=7.6 Hz), 7.40 (1H, d, J=8.0 Hz), 7.45-7.65 (3H, m), 7.82 (2H, d, J=8.4 Hz), 8.06 (2H, d, J=8.4 Hz), 8.21 (1H, d, J=8.0 Hz), 8.34 (1H, s), 8.65-8.70 (1H, m), 8.90-9.00 (1H, m), 10.4 (1H, s) ESI-MS Found: m/z 417 [M+H]$^+$

EXAMPLE 34

4-[(E)-2-(6-fluoropyridin-2-yl)vinyl]-N-[3-methyl-2-(tetrahydrofuran-3-yl)imidazo[1,2-a]pyridin-6-yl]benzamide The compound (119 mg) obtained in Production Example 42-1 and the compound (100 mg) obtained in Production Example 19-3 were processed in the same manner as in Example 1 to obtain the entitled compound (29 mg) as a colorless solid.

¹H-NMR (400 MHz, DMSO-d₆, δ ppm): 2.12-2.24 (2H, m), 2.42 (3H, s), 3.54-3.72 (2H, m), 3.79-3.87 (1H, m), 3.90-4.08 (2H, m), 7.05-7.10 (1H, m), 7.42 (1H, dd, J=9.6 Hz, 2.0 Hz), 7.48-7.54 (3H, m), 7.71 (1H, d, J=16.0 Hz), 7.86 (2H, d, J=8.2 Hz), 7.97-8.06 (3H, m), 8.93 (1H, s), 10.38 (1H, s) ESI-MS Found: m/z 443 [M+H]⁺

EXAMPLE 35

4-[(E)-2-(6-fluoropyridin-2-yl)vinyl]-N-[2-(1-hydroxy-1-methylethyl)-3-methylimidazo[1,2-a]pyridin-6-yl]benzamide The compound (50 mg) obtained in Production Example 45-3 and the compound (44 mg) obtained in Production Example 19-3 were processed in the same manner as in Example 1 to obtain the entitled compound (48 mg) as a white solid.

¹H-NMR (400 MHz, DMSO-d₆, δ ppm): 1.51 (6H, s), 2.58 (3H, s), 5.00 (1H, s), 7.08 (1H, dd, J=8.2, 2.7 Hz), 7.39-7.53 (4H, m), 7.71 (1H, d, J=16.0 Hz), 7.86 (2H, d, J=8.2 Hz), 7.96-8.06 (3H, m), 8.93 (1H, s), 10.38 (1H, s) ESI-MS Found: m/z 421 [M+H]⁺

EXAMPLE 36

4-[(E)-2-(5-fluoropyridin-2-ylvinyl]-N-[3-methyl-2-(tetrahydrofuran-3-yl)imidazo[1,2-a]pyridin-6-yl]benzamide The compound (60 mg) obtained in Production Example 42-1 and the compound (50 mg) obtained in Production Example J-1 were processed in the same manner as in Example 1 to obtain the entitled compound (61 mg) as a colorless solid.

¹H-NMR (400 MHz, DMSO-d₆, δ ppm): 2.12-2.24 (2H, m), 2.42 (3H, s), 3.54-3.72 (2H, m), 3.79-4.06 (3H, m), 7.40-7.54 (3H, m), 7.64-7.86 (5H, m), 8.02 (2H, d, J=8.4 Hz), 8.59 (1H, d, J=2.9 Hz), 8.93 (1H, s), 10.37 (1H, s) ESI-MS Found: m/z 443 [M+H]⁺

EXAMPLE 37

4-[(E)-2-(5-fluoropyridin-2-yl)vinyl]-N-[2-(1-hydroxy-1-methylethyl)-3-methylimidazo[1,2-a]pyridin-6-yl]benzamide The compound (57 mg) obtained in Production Example 45-3 and the compound (50 mg) obtained in Production Example J-1 were processed in the same manner as in Example 1 to obtain the entitled compound (58 mg) as a colorless solid.

¹H-NMR (400 MHz, DMSO-d₆, δ ppm): 1.51 (6H, s), 2.58 (3H, s), 5.00 (1H, s), 7.48-7.54 (3H, m), 7.63-7.71 (2H, m), 7.74-7.80 (1H, m), 7.83 (2H, d, J=8.4 Hz), 8.03 (2H, d, J=8.4 Hz), 8.60 (1H, d, J=2.7 Hz), 8.93 (1H, s), 10.37 (1H, s) ESI-MS Found: m/z 431 [M+H]⁺

EXAMPLE 38

4-[(E)-2-(5-fluoropyridin-2-yl)vinyl]-N-[2-(methoxymethyl)-3-methylimidazo[1,2-a]pyridin-6-yl]benzamide The compound (55 mg) obtained in Production Example 49-2 and the compound (50 mg) obtained in Production Example J-1 were processed in the same manner as in Example 1 to obtain the entitled compound (28 mg) as a colorless solid.

¹H-NMR (400 MHz, DMSO-d₆, δ ppm): 2.46 (3H, s), 3.27 (3H, s), 4.50 (2H, s), 7.46-7.58 (3H, m), 7.63-7.72 (2H, m), 7.77 (1H, dt, J=2.9 Hz, 8.6 Hz), 7.83 (2H, d, J=8.4 Hz), 8.03 (2H, d, J=8.4 Hz), 8.59 (1H, d, J=2.9 Hz), 8.98 (1H, s), 10.41 (1H, s) ESI-MS Found: m/z 417 [M+H]⁺

EXAMPLE 39

N-(2-ethyl-3-methylimidazo[1,2-a]pyridin-6-yl)-4-[(E)-2-(1,3-thiazol-2-yl)vinyl]benzamide The compound (8 mg) obtained in Production Example 39-4 and the compound (7 mg) obtained in Production Example 20-1 were processed in the same manner as in Example 1 to obtain the entitled compound (3 mg) as an orange solid.

¹H-NMR (400 MHz, CD₃OD, δ ppm): 1.33 (3H, t, J=7.6 Hz), 2.50 (3H, s), 2.81 (2H, q, J=7.6 Hz), 7.00 (1H, d, J=12.4 Hz), 7.14 (1H, d, J=12.4 Hz), 7.44 (1H, dd, J=9.6 Hz, 2.0 Hz), 7.50 (1H, d, J=9.6 Hz), 7.51 (1H, d, J=3.2 Hz), 7.62 (2H, d, J=8.8 Hz), 7.81 (1H, d, J=3.2 Hz), 8.04 (2H, d, J=8.8 Hz), 9.41 (1H, d, J=2.0 Hz) ESI-MS Found: m/z 389 [M+H]⁺

EXAMPLE 40

N-(2-ethyl-3-methylimidazo[1,2-a]pyridin-6-yl)-4-((Z)-2-fluoro-2-pyridin-2-ylvinyl)benzamide Aqueous 4 N sodium hydroxide solution (300 μL) was added to a methanol solution (5 mL) of methyl 4-((Z)-2-fluoro-2-pyridin-2-ylvinyl)benzenecarboxylate (25 mg) obtained in Production Example 21-2, and stirred at room temperature for 3 hours. The reaction liquid was neutralized with aqueous 1 N hydrochloric acid solution, and extracted with ethyl acetate. The organic layer was concentrated under reduced pressure to obtain a crude product of 4-(2-fluoro-2-pyridyl-2-ylvinyl)benzenecarboxylic acid. Next, diisopropylethylamine (20 μL) was added to a DMF solution (5 mL) of the thus-obtained 4-(2-fluoro-2-pyridyl-2-ylvinyl)benzenecarboxylic acid, the compound (14 mg) obtained in Production Example 39-4 and HATU (22 mg), and stirred at room temperature for 4 hours. Water was added to the reaction liquid, and extracted with ethyl acetate. The organic layer was washed with water and saturated saline water, and dried with anhydrous sodium sulfate. The organic layer was concentrated under reduced pressure, and the residue was purified through silica gel column chromatography (chloroform/methanol=90/1) to obtain the entitled compound (3 mg) as a white solid.

¹H-NMR (400 MHz, CDCl₃, δ ppm): 1.34 (3H, t, J=7.6 Hz), 2.44 (3H, s), 2.78 (2H, q, J=7.6 Hz), 7.15 (1H, d, J=38.8 Hz), 7.25-7.32 (1H, m), 7.60 (1H, d, J=9.2 Hz), 7.63-7.70 (2H, m), 7.78-7.85 (4H, m), 7.98 (2H, d, J=8.4 Hz), 8.64 (1H, d, J=4.8 Hz), 9.08 (1H, s)

EXAMPLE 41

N-(2-ethyl-3-methylimidazo[1,2-a]pyridin-6-yl)-4-[(Z)-1-fluoro-2-pyridin-2-ylvinyl]benzamide The compound (70 mg) obtained in Production Example 39-4 and the compound (69 mg) obtained in Production Example K-4 were processed in the same manner as in Example 1 to obtain the entitled compound (43 mg) as a colorless solid.

¹H-NMR (400 MHz, CDCl₃, δ ppm): 1.33 (3H, t, J=7.6 Hz), 2.44 (3H, s), 2.77 (2H, q, J=7.6 Hz), 6.72 (1H, d, J=39.2 Hz), 6.97 (1H, dd, J=9.6, 2.0 Hz), 7.18-7.22 (1H, m), 7.50 (1H, d, J=9.6 Hz), 7.74-7.78 (1H, m), 7.80 (2H, d, J=8.0 Hz), 7.95 (2H, d, J=8.0 Hz), 8.19 (1H, s), 8.60-8.63 (1H, m), 8.96 (1H, s) ESI-MS Found: m/z 401 [M+H]⁺

EXAMPLE 42

4-[(Z)-1-fluoro-2-pyridin-2-ylvinyl]-N-[3-methyl-2-(tetrahydrofuran-3-yl)imidazo[1,2-a]pyridin-6-yl)]benzamide The compound (25 mg) obtained in Production Example 42-1 and the compound (21 mg) obtained in Production Example K-4 were processed in the same manner as in Example 1 to obtain the entitled compound (22 mg) as a colorless solid.
¹H-NMR (400 MHz, CDCl₃, δ ppm): 2.30-2.42 (2H, m), 2.49 (3H, s), 3.60-3.68 (1H, m), 3.88-4.03 (2H, m), 4.10-4.20 (2H, m), 6.73 (1H, d, J=39.2 Hz), 6.98 (1H, d, J=9.6 Hz), 7.18-7.23 (1H, m), 7.55 (1H, d, J=9.6 Hz), 7.73-7.78 (1H, m), 7.82 (2H, d, J=8.0 Hz), 7.98 (2H, d, J=8.0 Hz), 8.01 (1H, s), 8.63 (1H, d, J=4.8 Hz), 9.00 (1H, s) ESI-MS Found: m/z 443 [M+H]⁺

EXAMPLE 43

4-((E)-1,2-difluoro-2-pyridin-2-ylvinyl)-N-(2-ethyl-3-methylimidazo[1,2-a]pyridin-6-yl)benzamide Aqueous 4 N sodium hydroxide solution (300 μL) was added to a methanol solution (5 mL) of methyl 4-((E)-1,2-difluoro-2-pyridin-2-ylvinyl)benzenecarboxylate (90 mg) obtained in Production Example 21-2, and stirred at room temperature for 3 hours. The reaction liquid was neutralized with aqueous 1 N hydrochloric acid solution, and extracted with ethyl acetate. The organic layer was concentrated under reduced pressure to obtain a crude product of 4-(1,2-difluoro-2-pyridyl-2-ylvinyl)benzenecarboxylic acid. Next, diisopropylethylamine (100 μL) was added to a DMF solution (5 mL) of the thus-obtained 4-(1,2-difluoro-2-pyridyl-2-ylvinyl)benzenecarboxylic acid, the compound (71 mg) obtained in Production Example 39-4 and HATU (109 mg), and stirred at room temperature for 4 hours. Water was added to the reaction liquid, and extracted with ethyl acetate. The organic layer was washed with water and saturated saline water, and dried with anhydrous sodium sulfate. The organic layer was concentrated under reduced pressure, and the residue was purified through silica gel column chromatography (chloroform/methanol=90/1) to obtain the entitled compound (43 mg) as a brown solid.
¹H-NMR (400 MHz, CDCl₃, δ ppm): 1.33 (3H, t, J=7.6 Hz), 2.44 (3H, s), 2.78 (2H, q, J=7.6 Hz), 6.97 (1H, dd, J=9.2, 2.0 Hz), 7.30-7.35 (1H, m), 7.49 (1H, d, J=9.2 Hz), 7.80-7.84 (2H, m), 7.93 (2H, d, J=8.8 Hz), 7.99 (2H, d, J=8.8 Hz), 8.20 (1H, s), 8.78 (1H, d, J=4.4 Hz), 8.97 (1H, s)

EXAMPLE 44

N-(2-ethyl-3-methylimidazo[1,2-a]pyridin-6-yl)-4-[(E)-1-fluoro-2-pyridin-2-ylvinyl]benzamide The compound (60 mg) obtained in Production Example 39-4 and the compound (59 mg) obtained in Production Example K-5 were processed in the same manner as in Example 1 to obtain the entitled compound (23 mg) as a brown solid.
¹H-NMR (400 MHz, CDCl₃, δ ppm): 1.33 (3H, t, J=7.6 Hz), 2.44 (3H, s), 2.77 (2H, q, J=7.6 Hz), 6.66 (1H, d, J=21.2 Hz), 6.92 (1H, dd, J=9.6, 2.0 Hz), 7.11 (1H, d, J=7.6 Hz), 7.13-7.16 (1H, m), 7.49 (1H, d, J=9.6 Hz), 7.52-7.56 (1H, m), 7.61 (2H, d, J=8.0 Hz), 7.84 (2H, d, J=8.0 Hz), 8.05 (1H, brs), 8.54 (1H, d, J=4.8 Hz), 8.94 (1H, s) ESI-MS Found: m/z 401 [M+H]⁺

EXAMPLE 45

N-[2-(3-hydroxypropyl)-3-methylimidazo[1,2-a]pyridin-6-yl]-4-[(E)-2-pyridin-2-ylvinyl]benzamide (1) The compound (80.0 mg) obtained in Production Example 47-5 and the compound (65.3 mg) obtained in Production Example 17-2 were processed in the same manner as in production Example 47-6 to obtain ethyl 3-[3-methyl-6-({4-[(E)-2-pyridin-2-ylvinyl]benzoyl}amino)imidazo[1,2-a]pyridin-2-yl]propionate (83.1 mg).
(2) The compound (50.0 mg) obtained in the above was processed in the same manner as in Example 14 to obtain the entitled compound (27.6 mg).
¹H-NMR (400 MHz, CDCl₃, δ ppm): 2.00 (2H, dd, J=7.0, 5.5 Hz), 2.46 (3H, s), 2.95 (2H, t, J=6.6 Hz), 3.80 (2H, t, J=5.7 Hz), 6.97 (1H, dd, J=9.4, 2.0 Hz), 7.22 (1H, dd, J=7.4, 4.7 Hz), 7.44 (1H, d, J=7.8 Hz), 7.48 (1H, d, J=9.4 Hz), 7.74-7.70 (4H, m), 7.94-7.92 (3H, m), 8.65 (1H, d, J=3.9 Hz), 9.00 (1H, s) ESI-MS Found: m/z 413 [M+H]⁺

EXAMPLE 46

N-[2-(3-hydroxy-3-methylbutyl)-3-methylimidazo[1,2-a]pyridin-6-yl]-4-[(E)-2-pyridin-2-ylvinyl]benzamide The compound (33.1 mg) obtained in Example 45(1) was processed in the same manner as in Example 16 to obtain the entitled compound (16.3 mg).
¹H-NMR (400 MHz, CDCl₃, δ ppm): 1.30 (6H, s), 1.93 (2H, t, J=7.1 Hz), 2.40 (3H, s), 2.89 (2H, t, J=7.1 Hz), 6.99-6.97 (1H, m), 7.20-7.17 (1H, m), 7.26-7.22 (1H, m), 7.35 (1H, d, J=9.4 Hz), 7.40 (1H, d, J=7.8 Hz), 7.70-7.62 (4H, m), 7.90 (2H, d, J=8.2 Hz), 8.34 (1H, brs), 8.61 (1H, d, J=4.7 Hz), 8.90 (1H, s) ESI-MS Found: m/z 441 [M+H]⁺

EXAMPLE 47

N-[3-methyl-2-(pyrrolidin-1-ylmethyl)imidazo[1,2-a]pyridin-6-yl]-4-[(E)-2-phenylvinyl]benzamide The compound (34.0 mg) obtained in Production Example 46-3 and 4-styrylbenzenecarboxylic acid (26.9 mg) were processed in the same manner as in Example 13 to obtain the entitled compound (30.8 mg).
¹H-NMR (400 MHz, CDCl₃, δ ppm): 1.81-1.78 (4H, m), 2.54 (3H, s), 2.65-2.62 (4H, brm), 3.83 (2H, s), 6.96 (1H, dd, J=9.6, 2.1 Hz), 7.17 (1H, d, J=16.4 Hz), 7.26 (1H, d, J=16.4 Hz), 7.35-7.31 (1H, m), 7.41 (2H, t, J=7.4 Hz), 7.59-7.54 (3H, m), 7.66 (2H, d, J=8.2 Hz), 7.81 (1H, s), 7.91 (2H, d, J=8.2 Hz), 9.03 (1H, s) ESI-MS Found: m/z 437 [M+H]⁺

EXAMPLE 48

N-[3-methyl-2-(3-pyrrolidin-1-ylpropyl)imidazo[1,2-a]pyridin-6-yl]-4-[(E)-2-pyridin-2-ylvinyl]benzamide The compound (20.0 mg) obtained in Example 45(2) was processed in the same manner as in Production Example 46-3 to obtain the entitled compound (10.2 mg).

$^1$H-NMR (400 MHz, CDCl$_3$, δ ppm): 1.79 (4H, s), 2.02-1.95 (2H, m), 2.45 (3H, s), 2.57-2.54 (6H, m), 2.81 (2H, t, J=7.6 Hz), 6.98 (1H, dd, J=9.4, 2.0 Hz), 7.21 (1H, dd, J=7.4, 4.7 Hz), 7.30-7.26 (1H, m), 7.43 (1H, d, J=7.8 Hz), 7.51-7.48 (1H, m), 7.74-7.68 (4H, m), 7.92 (2H, d, J=8.6 Hz), 8.15 (1H, brs), 8.65 (1H, d, J=4.3 Hz), 8.96 (1H, s) ESI-MS Found: m/z 466 [M+H]$^+$

EXAMPLE 49

N-(2-isopropyl-3-methylimidazo[1,2-a]pyridin-6-yl)-4-(2-pyridin-2-ylethyl)benzamide The compound (150 mg) obtained in Production Example 40-4 and the compound (129 mg) obtained in Production Example 17-2 were processed in the same manner as in Example 1 to obtain N-(2-isopropyl-3-methylimidazo[1,2-a]pyridin-6-yl)-4-(2-pyridin-2-ylvinyl)benzamide (36.2 mg). Next, 10% palladium-carbon (30 mg) was added to a methanol/THF mixed solution (1/1, 5 mL) of the obtained compound (190 mg), and stirred in a hydrogen atmosphere (1 atm) at room temperature for 1 hour. The reaction liquid was filtered through Celite, and the solvent was evaporated off from the filtrate under reduced pressure. The resulting residue was purified through reversed-phase HPLC (YMC-Pack ODS-AQ, acetonitrile/water (0.1% TFA) (10/90 to 90/10) and then desalted to obtain the entitled compound (11.0 mg).

$^1$H-NMR (400 MHz, DMSO-d$_6$, δ ppm): 1.25 (6H, d, J=6.8 Hz), 2.39 (3H, s), 3.11-3.13 (5H, m), 7.20-7.21 (1H, m), 7.26 (1H, d, J=7.8 Hz), 7.38-7.39 (3H, m), 7.48 (1H, d, J=9.8 Hz), 7.67-7.69 (1H, m), 7.90 (2H, d, J=8.3 Hz), 8.50-8.52 (1H, m), 8.89 (1H, s), 10.26 (1H, s)

EXAMPLE 50

N-(2-ethyl-3-methylimidazo[1,2-a]pyridin-6-yl)-3-fluoro-4-(2-pyridin-2-ylethyl)benzamide The compound (17 mg) obtained in Production Example 39-4 and the compound (17 mg) obtained in Production Example T-5 were processed in the same manner as in Example 1 to obtain the entitled compound (7 mg) as a pale yellow solid.

$^1$H-NMR (400 MHz, CD$_3$OD, δ ppm): 1.39 (3H, t, J=7.6 Hz), 2.58 (3H, s), 2.94 (2H, q, J=7.6 Hz), 3.20-3.40 (4H, m), 7.50-7.80 (5H, m), 7.85 (1H, dd, J=0.8 Hz, 5.6 Hz), 8.05 (1H, dd, J=2.0, 5.6 Hz), 8.10-8.20 (1H, m), 8.58-8.62 (1H, m), 9.38 (1H, dd, J=0.8 Hz, 2.0 Hz) ESI-MS Found: m/z 403 [M+H]$^+$

EXAMPLE 51

N-(2-ethyl-3-methylimidazo[1,2-a]pyridin-6-yl)-4-phenethylbenzamide

The compound (52 mg) obtained in Example 28 was reduced in the same manner as in Example 49 to obtain the entitled compound (36 mg).

$^1$H-NMR (400 MHz, CDCl$_3$, δ ppm): 1.34 (3H, t, J=7.4 Hz), 2.44 (3H, s), 2.78 (2H, q, J=7.4 Hz), 2.95-3.03 (4H, m), 6.90 (1H, dd, J=9.2, 1.9 Hz), 7.16 (2H, d, J=7.0 Hz), 7.20-7.31 (5H, m), 7.51 (1H, d, J=9.4 Hz), 7.78 (1H, s), 7.80 (2H, d, J=8.2 Hz), 8.97 (1H, s) ESI-MS Found: m/z 384 [M+H]$^+$

EXAMPLE 52

5-Phenethyl-[1,3,4]thiadiazole-3-carboxylic acid(2-ethyl-3-methylimidazo[1,2-a]pyridin-6-yl)amide The compound (92 mg) obtained in Production Example 39-4 and the compound obtained in Production Example 22-4 were processed in the same manner as in Example 1 to obtain the entitled compound (68 mg) as a yellow solid.

$^1$H-NMR (400 MHz, CD$_3$OD, δ ppm): 1.38 (3H, t, J=7.6 Hz), 2.58 (3H, s), 2.94 (2H, q, J=7.6 Hz), 3.19 (2H, t, J=9.6 Hz), 3.58 (2H, d, J=9.6 Hz), 7.19-7.36 (5H, m), 7.87 (1H, dd, J=9.6 Hz, 0.8 Hz), 8.18 (1H, dd, J=9.6 Hz, 1.0 Hz), 9.30 (1H, dd, J=1.0 Hz, 0.8 Hz) ESI-MS Found: m/z 392 [M+H]$^+$

EXAMPLE 53

N-(2-ethyl-3-methylimidazo[1,2-a]pyridin-6-yl)-4-(2-oxo-2-pyridin-2-ylethyl)benzamide Diisopropylethylamine (270 μL) was added to a DMF solution (5 mL) of the compound (96 mg) obtained in Production Example 39-4, the compound (94 mg) obtained in Production Example 23-1 and HATU (148 mg), and stirred at room temperature for 4 hours. Water was added to the reaction liquid, and extracted with ethyl acetate. The organic layer was washed with water and saturated saline water, and dried with anhydrous sodium sulfate. The organic layer was concentrated under reduced pressure, and the residue was purified through silica gel column chromatography (chloroform/methanol 90/1) to obtain the entitled compound (110 mg) as a brown solid.

$^1$H-NMR (400 MHz, CDCl$_3$, δ ppm): 1.33 (3H, t, J=7.6 Hz), 2.43 (3H, s), 2.77 (2H, q, J=7.6 Hz), 4.65 (2H, s), 6.91 (1H, dd, J=9.6, 2.0 Hz), 7.45-7.54 (3H, m), 7.83-7.90 (3H, m), 8.07 (1H, d, J=8.0 Hz), 8.73-8.75 (1H, m), 8.96 (1H, s)

EXAMPLE 54

N-(2-ethyl-3-methylimidazo[1,2-a]pyridin-6-yl)-4-(2-hydroxy-2-pyridin-2-ylethyl)benzamide A methanol solution (6 mL) of the compound (80 mg) obtained in Production Example 53 was cooled to 0° C., and sodium borohydride (30 mg) was added thereto and stirred at that temperature for 2 hours. Water was added to the reaction liquid, and extracted with ethyl acetate. The organic layer was washed with water and saturated saline water, and dried with anhydrous sodium sulfate. The organic layer was concentrated under reduced pressure, and the residue was purified through silica gel column chromatography (chloroform/methanol=90/1) to obtain the entitled compound (46 mg) as a white solid.

$^1$H-NMR (400 MHz, CDCl$_3$, δ ppm): 1.32 (3H, t, J=7.6 Hz), 2.42 (3H, s), 2.75 (2H, q, J=7.6 Hz), 3.06 (1H, dd, J=13.6, 7.2 Hz), 3.21 (1H, dd, J=13.6, 7.2 Hz), 4.98-5.03 (1H, m), 6.91 (1H, dd, J=9.2, 2.0 Hz), 7.19-7.29 (4H, m), 7.47 (1H, d, J=9.2 Hz), 7.66-7.70 (1H, m), 7.77 (2H, d, J=8.4 Hz), 7.92 (1H, s), 8.54 (1H, d, J=4.4 Hz), 8.94 (1H, s)

EXAMPLE 55

N-(2-ethyl-3-methylimidazo[1,2-a]pyridin-6-yl)-4-(2-fluoro-2-pyridin-2-ylethyl)benzamide DAST (20 μL) was added to a chloroform solution (6 mL) of the compound (16 mg) obtained in Example 54, and stirred at room temperature for 5 hours. Aqueous saturated sodium hydrogencarbonate solution was added to the reaction liquid, and extracted with ethyl acetate. The organic layer was washed with water and saturated saline water, and dried with anhydrous sodium sulfate. The organic layer was concentrated under reduced pressure, and the residue was purified through silica gel column chromatography (chloroform/methanol=90/1) to obtain the entitled compound (10 mg) as a brown solid.
$^1$H-NMR (400 MHz, CDCl$_3$, δ ppm): 1.33 (3H, t, J=7.6 Hz), 2.44 (3H, s), 2.78 (2H, q, J=7.6 Hz), 3.29-3.36 (1H, m), 3.43-3.55 (1H, m), 5.70-5.86 (1H, m), 6.95 (1H, dd, J=9.2, 2.0 Hz), 7.32-7.38 (3H, m), 7.52 (1H, d, J=9.2 Hz), 7.68-7.75 (2H, m), 7.81 (2H, d, J=8.4 Hz), 7.93 (1H, s), 8.61 (1H, d, J=4.4 Hz), 8.98 (1H, s)

EXAMPLE 56

4-(2,2-Difluoro-2-pyridin-2-ylethyl)-N-(2-ethyl-3-methylimidazo[1,2-a]pyridin-6-yl)benzamide Aqueous 4 N sodium hydroxide solution (300 μL) was added to a methanol solution (5 mL) of methyl 4-(2,2-difluoro-2-pyridin-2-ylethyl)benzenecarboxylate (90 mg) obtained in Production Example 21-2, and stirred at room temperature for 3 hours. The reaction liquid was neutralized with aqueous 1 N hydrochloric acid, and extracted with ethyl acetate. The organic layer was concentrated under reduced pressure to obtain a crude product of 4-(2,2-difluoro-2-pyridin-2-ylethyl)benzenecarboxylic acid. Next, diisopropylethylamine (86 μL) was added to a DMF (5 mL) solution of the obtained carboxylic acid, the compound (61 mg) obtained in Production Example 39-4 and HATU (94 mg), and stirred at room temperature for 4 hours. Water was added to the reaction liquid, and extracted with ethyl acetate. The organic layer was washed with water and saturated saline water, and then dried with anhydrous sodium sulfate. The organic layer was concentrated under reduced pressure, and the residue was purified through silica gel column chromatography (chloroform/methanol=90/1) to obtain the entitled compound (20 mg) as a white solid.
$^1$H-NMR (400 MHz, CDCl$_3$, δ ppm): 1.30 (3H, t, J=7.6 Hz), 2.43 (3H, s), 2.78 (2H, q, J=7.6 Hz), 3.75 (2H, t, J=16.4 Hz), 6.88 (1H, dd, J=9.2, 2.0 Hz), 7.36-7.47 (3H, m), 7.49-7.52 (2H, m), 7.72-7.78 (4H, m), 8.72 (1H, d, J=4.4 Hz), 8.93 (1H, s)

EXAMPLE 57

N-(2-ethyl-3-methylimidazo[1,2-a]pyridin-6-yl)-4-(1-hydroxy-2-pyridin-2-ylethyl)benzamide The compound (117 mg) obtained in Production Example 39-4 and the compound (114 mg) obtained in Production Example K-7 were processed in the same manner as in Example 1 to obtain the entitled compound (64 mg) as a brown solid.
$^1$H-NMR (400 MHz, CDCl$_3$, δ ppm): 1.33 (3H, t, J=7.6 Hz), 2.43 (3H, s), 2.77 (2H, q, J=7.6 Hz), 3.13-3.19 (2H, m), 5.22-5.26 (1H, m), 6.96 (1H, dd, J=9.2, 2.0 Hz), 7.11 (1H, d, J=8.0 Hz), 7.19-7.23 (1H, m), 7.48 (1H, d, J=9.2 Hz), 7.53 (2H, d, J=8.4 Hz), 7.61-7.66 (1H, m), 7.85 (2H, d, J=8.4 Hz), 8.04 (1H, brs), 8.52-8.55 (1H, m), 8.96 (1H, s) ESI-MS Found: m/z 401 [M+H]$^+$

EXAMPLE 58

N-(2-ethyl-3-methylimidazo[1,2-a]pyridin-6-yl)-4-(1-fluoro-2-pyridin-2-ylethyl)benzamide DAST (100 μL) was added to a chloroform (4 mL) solution of the compound (20 mg) obtained in Example 57, and stirred at room temperature for 1 hour. Aqueous saturated sodium hydrogencarbonate solution was added to the reaction liquid, and extracted with ethyl acetate. The organic layer was washed with water and saturated saline water, and then dried with anhydrous sodium sulfate. The solvent was evaporated off under reduced pressure, and the resulting residue was purified through silica gel column chromatography (chloroform/methanol=80/1) to obtain the entitled compound (4 mg) as a brown solid.
$^1$H-NMR (400 MHz, CDCl$_3$, δ ppm): 1.35 (3H, t, J=7.6 Hz), 2.46 (3H, s), 2.80 (2H, q, J=7.6 Hz), 3.20-3.50 (2H, m), 5.94-6.10 (1H, m), 7.15-7.30 (3H, m), 7.50 (1H, d, J=8.0 Hz), 7.58-7.72 (3H, m), 7.97 (2H, d, J=8.0 Hz), 8.58-8.62 (1H, m), 9.05 (1H, s) ESI-MS Found: m/z 403 [M+H]$^+$

EXAMPLE 59

N-[3-methyl-2-(tetrahydrofuran-3-yl)imidazo[1,2-a]pyridin-6-yl]-4-(pyridin-2-ylmethylsulfanyl)benzamide The compound (30 mg) obtained in Production Example 42-1 and the compound (25.3 mg) obtained in Production Example 24-1 were processed in the same manner as in Example 1 to obtain the entitled compound (22.7 mg).
$^1$H-NMR (400 MHz, CDCl$_3$, δ ppm): 2.30-2.39 (2H, m), 2.44 (3H, s), 3.59-3.61 (1H, m), 3.88-3.90 (1H, m), 3.96-3.98 (1H, m), 4.09-4.17 (2H, m), 4.35 (2H, s), 6.92-6.95 (1H, m), 7.17-7.19 (1H, m), 7.39-7.42 (3H, m), 7.49 (1H, d, J=9.8 Hz), 7.64-7.65 (1H, m), 7.75 (2H, d, J=8.3 Hz), 8.08 (1H, s), 8.54-8.55 (1H, m), 8.94 (1H, s)

EXAMPLE 60

4-Benzylamino-N-(2-cyclopropyl-3-methylimidazo[1,2-a]pyridin-6-yl)benzamide

The compound (50 mg) obtained in Production Example 41-1 and the compound (62.8 mg) obtained in Production Example 25-3 were processed in the same manner as in Example 1 to obtain tert-butyl benzyl-[4-(2-cyclopropyl-3-methylimidazo[1,2-a]pyridin-6-ylcarbamoylphenyl)carbamate (79 mg). A trifluoroacetic acid solution (2 mL) of the obtained compound (75 mg) was stirred at room temperature for 10 minutes. The reaction solution was concentrated under reduced pressure, and chloroform/methanol (10/1, 20 mL) was added to the resulting residue, and washed with saturated sodium hydrogencarbonate. The organic layer was dried with anhydrous magnesium sulfate, and the solvent was evaporated off under reduced pressure to obtain the entitled compound (58.5 g).

¹H-NMR (400 MHz, DMSO-d₆, δ ppm): 0.86-0.88 (4H, m), 2.02-2.06 (1H, m), 2.44 (3H, s), 4.36 (2H, d, J=5.9 Hz), 6.97 (1H, t, J=6.1 Hz), 7.23-7.25 (1H, m), 7.31-7.38 (7H, m), 7.75 (2H, q, J=7.3 Hz), 8.85 (1H, s), 9.83 (1H, s)

EXAMPLE 61

Pyridine-2-carboxylic acid[4-(2-cyclopropyl-3-methylimidazo[1,2-a]pyridin-6-ylcarbamoyl)phenyl]amide The compound (30 mg) obtained in Production Example 41-1 and the compound (29 mg) obtained in Production Example 26-2 were processed in the same manner as in Example 1 to obtain the entitled compound (48.1 mg).

¹H-NMR (400 MHz, CDCl₃, δ ppm): 0.94-1.06 (4H, m), 1.95-2.02 (1H, m), 2.49 (3H, s), 6.99 (1H, d, J=9.3 Hz), 7.43 (1H, d, J=9.3 Hz), 7.51-7.52 (1H, m), 7.89-7.95 (5H, m), 8.28 (1H, d, J=7.8 Hz), 8.63-8.64 (1H, m), 8.92 (1H, s), 10.24 (1H, s)

EXAMPLE 62

N-[3-methyl-2-(2-trans-methylcyclopropyl)imidazo[1,2-a]pyridin-6-yl]-4-(pyridin-2-yloxy)benzamide The compound (38.4 mg) obtained in Production Example 38-6 and the compound (30.0 mg) obtained in Production Example 27-2 were processed in the same manner as in Example 1 to obtain the entitled compound (27.7 mg) as a pale brown solid.

¹H-NMR (400 MHz, CDCl₃, δ ppm): 0.72-0.77 (1H, m), 1.19-1.24 (3H, m), 1.22 (3H, d, J=6.3 Hz), 1.37-1.45 (1H, m), 1.62-1.65 (1H, m), 2.50 (3H, s), 6.86 (1H, dd, J=9.4, 2.3 Hz), 7.01 (1H, d, J=8.6 Hz), 7.06-7.08 (1H, m), 7.25-7.28 (2H, m), 7.46 (1H, d, J=9.4 Hz), 7.69 (1H, s), 7.73-7.77 (1H, m), 7.92 (2H, d, J=9.4 Hz), 8.21-2.22 (1H, m), 8.93 (1H, s) ESI-MS Found: m/z 399 [M+H]⁺

EXAMPLE 63

N-(2-cyclopropyl-3-methylimidazo[1,2-a]pyridin-6-yl)-4-(pyridin-3-yloxy)benzamide The compound (20 mg) obtained in Production Example 41-1 and 4-(pyridin-3-yloxy)benzenecarboxylic acid (19.3 mg) were processed in the same manner as in Example 1 to obtain the entitled compound (22.1 mg).

¹H-NMR (400 MHz, DMSO-d₆, δ ppm): 0.86-0.91 (4H, m), 2.04-2.08 (1H, m), 2.46 (3H, s), 7.19 (2H, d, J=8.8 Hz), 7.37-7.41 (2H, m), 7.49-7.51 (1H, m), 7.57-7.60 (1H, m), 8.05 (2H, d, J=8.8 Hz), 8.46-8.47 (2H, m), 8.87 (1H, s), 10.31 (1H, s)

EXAMPLE 64

N-(2-ethyl-3-methylimidazo[1,2-a]pyridin-6-yl)-4-(5-fluoropyridin-2-yloxy)benzamide The compound (53.2 mg) obtained in Production Example 39-4 and the compound (50.0 mg) obtained in Production Example 28-4 were processed in the same manner as in Example 1 to obtain the entitled compound (34.4 mg) as a pale yellow solid.

¹HNMR (400 MHz, CDCl₃, δ ppm): 1.34 (3H, t, J=7.7 Hz), 2.44 (3H, s), 2.79 (2H, q, J=7.7 Hz), 6.90 (1H, dd, J=9.6, 2.1 Hz), 7.01 (1H, dd, J=9.0, 3.5 Hz), 7.24 (2H, d, J=9.1 Hz), 7.79 (1H, s), 7.94 (2H, d, J=9.1 Hz), 8.06 (1H, d, J=3.1 Hz), 8.95 (1H, s) ESI-MS Found: m/z 391 [M+H]⁺

EXAMPLE 65

N-(2-ethyl-3-methylimidazo[1,2-a]pyridin-6-yl)-4-(6-fluoropyridin-2-yloxy)benzamide The compound (106.7 mg) obtained in Production Example 39-4 and the compound (100.0 mg) obtained in Production Example 29-2 were processed in the same manner as in Example 1 to obtain the entitled compound (117.7 mg) as a pale yellow solid.

¹HNMR (400 MHz, CDCl₃, δ ppm): 1.32 (3H, t, J=7.6 Hz), 2.42 (3H, s), 2.77 (2H, q, J=7.6 Hz), 6.68 (1H, dd, J=9.4, 2.7 Hz), 6.84 (1H, d, J=7.8 Hz), 6.93 (1H, dd, J=9.4, 2.3 Hz), 7.25 (2H, d, J=9.2 Hz), 7.48 (1H, d, J=9.4 Hz), 7.82 (1H, m), 7.93 (2H, d, J=9.2 Hz), 8.00 (1H, s), 8.94 (1H, s) CI-MS Found: m/z 391 [M+H]⁺

EXAMPLE 66

N-(2-ethyl-3-methylimidazo[1,2-a]pyridin-6-yl)-4-(3-fluoropyridin-2-yloxy)benzamide The compound (53.2 mg) obtained in Production Example 39-4 and the compound (50.0 mg) obtained in Production Example 30-1 were processed in the same manner as in Example 1 to obtain the entitled compound (47.6 mg) as a pale yellow solid.

¹HNMR (400 MHz, CDCl₃, δ ppm): 1.34 (3H, t, J=7.5 Hz), 2.45 (3H, s), 2.79 (2H, q, J=7.5 Hz), 7.07-7.11 (2H, m), 7.31 (2H, d, J=9.4 Hz), 7.53-7.57 (2H, m), 7.97-8.00 (3H, m), 8.19 (1H, s)

ESI-MS Found: m/z 391 [M+H]⁺

EXAMPLE 67

4-(4-Chloropyridin-2-yloxy)-N-(2-ethyl-3-methylimidazo[1,2-a]pyridin-6-yl)benzamide The compound (50.8 mg) obtained in Production Example 39-4 and the compound (50.3 mg) obtained in Production Example 31-4 were processed in the same manner as in Example 1 to obtain the entitled compound (48.0 mg) as a pale yellow solid.

¹HNMR (400 MHz, CDCl₃, δ ppm): 1.34 (3H, t, J=7.6 Hz), 2.50 (3H, s), 2.78 (2H, q, J=7.6 Hz), 7.00 (1H, d, J=1.6 Hz), 7.07 (1H, dd, J=5.5, 2.0 Hz), 7.24 (2H, d, J=9.1 Hz), 7.99 (1H, d, J=9.8 Hz), 8.11 (1H, d, J=5.5 Hz), 8.18 (2H, d, J=9.1 Hz), 9.44 (1H, s), 10.31 (1H, s)

ESI-MS Found: m/z 402 [M+H]⁺

EXAMPLE 68

N-(2-ethyl-3-methylimidazo[1,2-a]pyridin-6-yl)-4-(4-methylsulfanylpyridin-2-yloxy)benzamide The compound (90.5 mg) obtained in Production Example 39-4 and the compound (87.5 mg) obtained in Production Example 32-2 were processed in the same manner as in Example 1 to obtain a crude amide (132.5 mg). A part (21.3 mg) of the thus-obtained crude amide was purified through reversed-phase HPLC to obtain the entitled compound (11.9 mg) as a colorless solid.

¹HNMR (400 MHz, CDCl₃, δ ppm): 1.34 (3H, t, J=7.6 Hz), 2.44 (3H, s), 2.52 (3H, s), 2.79 (2H, q, J=7.6 Hz), 6.79 (1H, d, J=1.6 Hz), 6.89-6.91 (2H, m), 7.26 (2H, d, J=9.1 Hz), 7.52 (1H, d, J=9.4 Hz), 7.93 (2H, d, J=9.1 Hz), 8.00 (1H, d, J=5.5 Hz), 8.96 (1H, s)

ESI-MS Found: m/z 419 [M+H]$^+$

EXAMPLE 69

N-(2-cyclopropyl-3-methylimidazo[1,2-a]pyridin-6-yl)-4-(5-trifluoromethylpyridin-2-yloxy)benzamide The compound (20 mg) obtained in Production Example 41-1 and the compound (21.8 mg) obtained in Production Example 33-2 were processed in the same manner as in Example 1 to obtain the entitled compound (23.6 mg).

$^1$H-NMR (400 MHz, DMSO-d$_6$, δ ppm): 0.88-0.89 (4H, m), 2.04-2.08 (1H, m), 2.47 (3H, s), 7.37-7.40 (5H, m), 8.07 (2H, d, J=8.8 Hz), 8.28-8.32 (1H, m), 8.61 (1H, s), 8.90 (1H, s), 10.38 (1H, s)

EXAMPLE 70

N-(2-ethyl-3-methylimidazo[1,2-a]pyridin-6-yl)-4-(3-trifluoromethylpyridin-2-yloxy)benzamide The compound (43.9 mg) obtained in Production Example 39-4 and the compound (50.0 mg) obtained in Production Example 34-2 were processed in the same manner as in Example 1 to obtain the entitled compound (45.6 mg) as a pale yellow solid.

$^1$HNMR (400 MHz, CDCl$_3$, δ ppm): 1.35 (3H, t, J=7.6 Hz), 2.46 (3H, s), 2.80 (2H, q, J=7.6 Hz), 6.93 (1H, dd, J=9.4, 2.0 Hz), 7.19 (1H, dd, J=7.4, 5.1 Hz), 7.34 (2H, d, J=9.2 Hz), 7.54 (1H, d, J=9.4 Hz), 7.83 (1H, s), 7.99 (2H, d, J=9.2 Hz), 8.06 (1H, dd, J=7.4, 1.6 Hz), 8.34 (1H, dd, J=4.7, 1.6 Hz), 8.98 (1H, s)

ESI-MS Found: m/z 441 [M+H]$^+$

EXAMPLE 71

N-(2-ethyl-3-methylimidazo[1,2-a]pyridin-6-yl)-4-(4-trifluoromethylpyridin-2-yloxy)benzamide The compound (43.9 mg) obtained in Production Example 39-4 and the compound (50.0 mg) obtained in Production Example 35-2 were processed in the same manner as in Example 1 to obtain the entitled compound (50.7 mg) as a pale brown solid.

$^1$HNMR (400 MHz, CDCl$_3$, δ ppm): 1.36 (3H, t, J=7.4 Hz), 2.47 (3H, s), 2.81 (2H, q, J=7.4 Hz), 6.92 (1H, dd, J=9.4, 2.0 Hz), 7.27-7.30 (2H, m), 7.33 (2H, d, J=9.2 Hz), 7.55 (1H, d, J=9.4 Hz), 7.72 (1H, s), 7.99 (2H, d, J=9.1 Hz), 8.37 (1H, d, J=5.1 Hz), 8.98 (1H, s)

CI-MS Found: m/z 441 [M+H]$^+$

EXAMPLE 72

4-(6-Chloropyridazin-3-yloxy)-N-(2-cyclopropyl-3-methylimidazo[1,2-a]pyridin-6-yl)benzamide The compound (20 mg) obtained in Production Example 41-1 and the compound (19.3 mg) obtained in Production Example 36-2 were processed in the same manner as in Example 1 to obtain the entitled compound (11.3 mg).

$^1$H-NMR (400 MHz, DMSO-d$_6$, δ ppm): 0.88-0.91 (4H, m), 2.05-2.07 (1H, m), 2.47 (3H, s), 7.37-7.45 (4H, m), 7.70 (1H, d, J=9.3 Hz), 8.02 (1H, d, J=9.3 Hz), 8.09 (2H, d, J=8.8 Hz), 8.90 (1H, s), 10.38 (1H, s)

EXAMPLE 73

N-(2-cyclopropyl-3-methylimidazo[1,2-a]pyridin-6-yl)-6-phenoxynicotinamide

The compound (20 mg) obtained in Production Example 41-1 and 6-phenoxynicotinic acid (16.5 mg) were processed in the same manner as in Example 1 to obtain the entitled compound (21.0 mg).

$^1$H-NMR (400 MHz, DMSO-d$_6$, δ ppm): 0.86-0.91 (4H, m), 2.05-2.08 (1H, m), 2.46 (3H, s), 7.18-7.22 (3H, m), 7.26-7.35 (2H, m), 7.42-7.47 (3H, m), 8.39 (1H, dd, J=8.8, 2.4 Hz), 8.74 (1H, d, J=2.0 Hz), 8.86 (1H, s), 10.41 (1H, s)

EXAMPLE 74

5-Phenoxypyrimidine-2-carboxylic acid(2-cyclopropyl-3-methylimidazo[1,2-a]pyridin-6-yl)amide The compound (20 mg) obtained in Production Example 41-1 and 5-phenoxypyrimidine-2-carboxylic acid (16.6 mg) were processed in the same manner as in Example 1 to obtain the entitled compound (25.9 mg).

$^1$H-NMR (400 MHz, DMSO-d$_6$, δ ppm): 0.88-0.91 (4H, m), 2.06-2.08 (1H, m), 2.48 (3H, s), 7.27-7.33 (3H, m), 7.45-7.51 (3H, m), 7.57-7.58 (1H, m), 8.78 (2H, s), 8.96 (1H, s), 10.88 (1H, s)

EXAMPLE 75

4-Benzenesulfonyl-N-(2-cyclopropyl-3-methylimidazo[1,2-a]pyridin-6-yl)benzamide

The compound (20 mg) obtained in Production Example 41-1 and 4-benzenesulfonylbenzenecarboxylic acid (18.2 mg) were processed in the same manner as in Example 1 to obtain the entitled compound (21.0 mg).

$^1$H-NMR (400 MHz, DMSO-d$_6$, δ ppm): 0.86-0.89 (4H, m), 2.05-2.08 (1H, m), 2.45 (3H, s), 7.32 (1H, dd, J=9.3, 2.0 Hz), 7.41-7.42 (1H, m), 7.66 (2H, m), 7.72-7.74 (1H, m), 8.01-8.03 (2H, m), 8.14 (4H, s), 8.85 (1H, s), 10.56 (1H, s)

EXAMPLE 76

N-(2-cyclopropyl-3-methylimidazo[1,2-a]pyridin-6-yl)-4-phenethyloxybenzamide trifluoroacetate The compound (50 mg) obtained in Production Example 41-1 and the compound (46.5 mg) obtained in Production Example 37-2 were processed in the same manner as in Example 1, and the resulting crude product was purified through reversed-phase HPLC (YMC-Pack ODS-AQ, acetonitrile/water (0.1% TFA) (10/90 to 90/10)) to obtain the entitled compound (58.6 mg).

$^1$H-NMR (400 MHz, DMSO-d$_6$, δ ppm): 0.95-0.99 (2H, m), 1.12-1.14 (2H, m), 2.24-2.29 (1H, m), 2.56 (3H, s), 3.08 (2H, t, J=6.8 Hz), 4.31 (2H, t, J=6.8 Hz), 7.12 (2H, d, J=8.8 Hz), 7.23-7.26 (1H, m), 7.31-7.36 (4H, m), 7.83 (1H, d, J=9.8 Hz), 8.01-8.05 (3H, m), 9.24 (1H, s), 10.60 (1H, s)

EXAMPLE 77

N-(2-cyclopropyl-3-methylimidazo[1,2-a]pyridin-6-yl)-4-(2-phenoxyethoxy)benzamide trifluoroacetate The compound (15 mg) obtained in Production Example 41-1 and 4-(2-phenoxyethoxy)benzenecarboxylic acid (15 mg) were processed in the same manner as in Example 1, and the resulting crude product was purified through reversed-phase HPLC (YMC-Pack ODS-AQ, acetonitrile/water (0.1% TFA) (10/90 to 90/10)) to obtain the entitled compound (13.9 mg).

$^1$H-NMR (400 MHz, DMSO-$d_6$, δ ppm): 0.96-1.00 (2H, m), 1.13-1.15 (2H, m), 2.25-2.29 (1H, m), 2.56 (3H, s), 4.35-4.36 (2H, m), 4.44-4.44 (2H, m), 6.97-6.99 (3H, m), 7.19 (2H, d, J=8.8 Hz), 7.31-7.33 (2H, m), 7.83 (1H, d, J=9.8 Hz), 8.02-8.05 (3H, m), 9.25 (1H, s), 10.62 (1H, s)

EXAMPLE 78

5-(Pyridin-2-ylmethoxy)-1H-indole-2-carboxylic acid(2-cyclopropyl-3-methylimidazo[1,2-a]pyridin-6-yl)amide ditrifluoroacetate The compound (30 mg) obtained in Production Example 41-1 and the compound (32 mg) obtained in Production Example 3-4 were processed in the same manner as in Example 1, and the resulting crude product was purified through reversed-phase HPLC (YMC-Pack ODS-AQ, acetonitrile/water (0.1% TFA) (10/90 to 90/10)) to obtain the entitled compound (26 mg).

$^1$H-NMR (400 MHz, DMSO-$d_6$, δ ppm): 0.99 (2H, m), 1.18 (2H, m), 2.30 (1H, m), 2.55 (3H, s), 5.25 (2H, s), 7.06 (1H, dd, J=9.0, 2.3 Hz), 7.31 (1H, d, J=2.3 Hz), 7.40-7.45 (3H, m), 7.63 (1H, d, J=7.8 Hz), 7.88-7.95 (2H, m), 8.16 (1H, dd, J=9.8, 2.0 Hz), 8.64 (1H, m), 9.25 (1H, s), 10.74 (1H, s), 11.77 (1H, s)

EXAMPLE 79

1-Benzylpyrrolidine-3-carboxylic acid(2-cyclopropyl-3-methylimidazo[1,2-a]pyridin-6-yl)amide The compound (62 mg) obtained in Production Example 41-1 and 1-benzylpyrrolidine-3-carboxylic acid (50 mg) were processed in the same manner as in Example 1 to obtain the entitled compound (12 mg).

$^1$H-NMR (400 MHz, DMSO-$d_6$, δ ppm): 0.80-0.90 (4H, m), 1.90-2.10 (3H, m), 2.40-2.50 (2H, m), 2.42 (3H, s), 2.60-2.80 (1H, m), 2.88 (1H, t, J=8.8 Hz), 3.00-3.10 (1H, m), 3.57 (1H, d, J=12.8 Hz), 3.62 (1H, d, J=12.8 Hz), 7.05 (1H, dd, J=2.0 Hz, 9.6 Hz), 7.20-7.30 (1H, m), 7.30-7.40 (5H, m), 8.77 (1H, d, J=0.8 Hz), 9.96 (1H, s)

INDUSTRIAL APPLICABILITY

The compounds of the invention have an MCH-1R antagonistic effect and are useful as preventing or treating agents for metabolic disorders represented by, for example, obesity, diabetes, hormone disorder, hyperlipidemia, gout, fatty liver, hepatitis, cirrhosis; cardiovascular disorders represented by, for example, stenocardia, acute or congestive heart failure, myocardial infarction, coronary atherosclerosis, hypertension, renal diseases, electrolyte abnormality; central nervous system or peripheral nervous system disorders represented by, for example, bulimia, emotional disturbance, depression, anxiety, epilepsy, delirium, dementia, schizophrenia, attention-deficit hyperactivity disorder, memory impairment, sleep disorders, cognitive failure, dyskinesia, paresthesias, smell disorders, morphine tolerance, drug dependence, alcoholism; reproductive disorders represented by infertility, preterm labor and sexual dysfunction; and other digestive disorders, respiratory disorders, cancer or pigmentation.

The invention claimed is:

1. A compound of formula I or its pharmaceutically-acceptable salt:

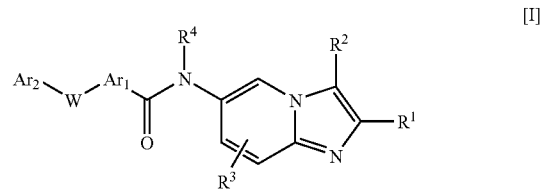

wherein:
$R^1$ $R^2$ are each independently selected from the group consisting of:
(1) a hydrogen atom,
(2) a halogen atom,
(3) a $C_{1-6}$ alkyl group,
(4) a $C_{2-6}$ alkenyl group,
(5) a $C_{3-8}$ cycloalkyl-$C_{0-4}$ alkyl group,
(6) a $C_{1-6}$ alkylamino group,
(7) a di-$C_{1-6}$ alkylamino group,
(8) a $C_{1-6}$ alkylcarbonylamino group,
(9) a $C_{1-6}$ alkylcarbonyl($C_{1-6}$ alkyl)amino group,
(10) a 3- to 8-membered heterocycloalkyl-$C_{0-4}$ alkyl group, and
(11) a pyrazolyl-$C_{1-4}$ alkyl group,
wherein any hydrogen atom in the alkyl moiety may be optionally substituted with $R^5$, any hydrogen atom in the cycloalkyl or heterocycloalkyl moiety may be optionally substituted with $R^6$, and $R^1$ and $R^2$ must not be hydrogen atoms at the same time, or
$R^1$ and $R^2$ together form, along with the carbon atom bonding thereto, a 5- to 8-membered carbon ring optionally substituted with $R^6$;
$R^3$ is a hydrogen atom, a halogen atom, a $C_{1-6}$ alkyl group, or a $C_{1-6}$ alkyloxy group;
$R^4$ is a hydrogen atom, or a $C_{1-6}$ alkyl group;
$R^5$ is selected from the group consisting of a halogen atom, a cyano group, a hydroxyl group, an amino group, a $C_{1-6}$ alkyl group optionally substituted with a fluorine atom or a hydroxyl group, a mono-$C_{1-6}$ alkylamino group, a di-$C_{1-6}$ alkylamino group, a $C_{1-6}$ alkyloxy group optionally substituted with a fluorine atom, a $C_{1-6}$ alkyloxy-$C_{1-6}$ alkyl group, a $C_{1-6}$ alkyloxycarbonyl group, a $C_{1-6}$ alkyloxycarbonylamino group, a $C_{1-6}$ alkyloxycarbonyl($C_{1-6}$ alkyl)amino group, a $C_{1-6}$ alkylcarbonyl group, a $C_{1-6}$ alkylcarbonyloxy group, a $C_{1-6}$ alkylcarbonylamino group, a $C_{1-6}$ alkylcarbonyl($C_{1-6}$ alkyl)amino group, a carbamoyl group, a mono-$C_{1-6}$ alkylcarbamoyl group, a di-$C_{1-6}$ alkylcarbamoyl group, a carbamoylamino group, a mono-$C_{1-6}$ alkylcarbamoylamino group, a di-$C_{1-6}$ alkylcarbamoylamino group, a mono-$C_{1-6}$ alkylcarbamoyl($C_{1-6}$ alkyl)amino group, a di-$C_{1-6}$ alkylcarbamoyl($C_{1-6}$ alkyl)amino group, a carbamoyloxy group, a mono-$C_{1-6}$ alkylcarbamoyloxy group, a di-$C_{1-6}$ alkylcarbamoyloxy group, a $C_{1-6}$ alkylsulfonyl group, a $C_{1-6}$ alkylsulfonylamino group, a $C_{1-6}$ alkylsulfonyl($C_{1-6}$ alkyl)amino group, a sulfamoyl group, a mono-$C_{1-6}$ alkylsulfamoyl group, a di-$C_{1-6}$ alkylsulfamoyl group, a sulfamoylamino group, a (mono-$C_{1-6}$ alkylsulfamoyl)amino group, a (di-$C_{1-6}$ alkylsulfamoyl)amino group, a mono-$C_{1-6}$ alkylsulfamoyl($C_{1-6}$ alkyl)amino group, and a di-$C_{1-6}$ alkylsulfamoyl($C_{1-6}$ alkyl)amino group;

$R^6$ is $R^5$ or an oxo group;

W is:
(a) —$(CH_2)_{m+1}$—,
(b) —$(CH_2)_m$—CH=CH—$(CH_2)_n$—,
(c) —$(CH_2)_m$—O—$(CH_2)_n$—,
(d) —O—$(CH_2)_{m+1}$—O—,
(e) —$(CH_2)_m$—S(O)$_{y1}$—$(CH_2)_n$—,
(f) —$(CH_2)_m$—C(O)—(O)$_{y2}$—$(CH_2)_n$—,
(g) —$(CH_2)_m$—C(O)—NH—$(CH_2)_n$—,
(h) —$(CH_2)_m$—NH—C(O)—$(CH_2)_n$—, or
(i) —$(CH_2)_m$—NH—$(CH_2)_n$—, wherein any hydrogen atom in the alkylene moiety of the substituent may be optionally substituted with $R^5$;

m and n are each independently an integer of from 0 to 10, satisfying $0 \leq m+n \leq 10$;

y1 is 0, 1 or 2; y2 is 0 or 1;

$Ar_1$ is a divalent substituent, selected from
(a) a monocyclic or bicyclic, 3- to 8-membered aromatic or aliphatic heterocyclic group optionally substituted with $R^5$, and
(b) a monocyclic or bicyclic, 3- to 8-membered aromatic or aliphatic carbocyclic group optionally substituted with $R^5$;

$Ar_2$ is a 5- or 6-membered aromatic carbocyclic group optionally having a substituent, or a 5- or 6-membered aromatic heterocyclic group optionally having a substituent selected from: a chlorine group, a fluorine group, a bromine group, a methyl group, an ethyl group, an isopropyl group, a 1-hydroxy-1-methylethyl group, a difluoromethyl group, a trifluoromethyl group, a methoxy group, an ethoxy group, an isopropyloxy group, a difluoromethoxy group, a trifluoromethoxy group, a cyclopropyl group, a cyclopropyloxy group, a methylsulfonyl group, a methylsulfinyl group, a methylsulfanyl group, an ethylsulfonyl group, a nitrile group, and a dimethylamino group.

2. The compound according to claim 1 or its pharmaceutically-acceptable salt, wherein $R^1$ is selected from a group consisting of a methyl group, an ethyl group, an isopropyl group, a t-butyl group, a hydroxymethyl group, a 1-methyl-1-hydroxyethyl group, a cyclopropyl group, a tetrahydrofuran-3-yl group, a 3-oxocyclobutyl group, a 3-methoxycyclobutyl group, a methoxymethyl group, a pyrrolidin-1-ylpropyl group, a 3-morpholin-4-ylpropyl group, a 3-hydroxypropyl group, a 3-hydroxy-3-methylbutyl group, a 3-(3-fluoropyrrolidin-1-yl)propyl group, a 3-(3,3-difluoropyrrolidin-1-yl)propyl group, and a 3-hydroxy-3-methylcyclobutyl group.

3. The compound according to claim 1 or its pharmaceutically-acceptable salt, wherein $R^2$ is selected from the group consisting of a hydrogen atom, a methyl group, an ethyl group, a hydroxymethyl group, a 1-hydroxyethyl group, a cyclopropyl group, a methoxymethyl group, a cyanomethyl group, and a pyrrolidin-1-ylmethyl group.

4. The compound according to claim 1 or its pharmaceutically-acceptable salt, wherein $R^3$ is a hydrogen atom, a methyl group, or a methoxy group.

5. The compound according to claim 1 or its pharmaceutically-acceptable salt, wherein $R^4$ is a hydrogen atom, or a methyl group.

6. The compound according to claim 1 or its pharmaceutically-acceptable salt, wherein W is selected from the group consisting of —CH=CH—, —O—, —O—$CH_2$—, —$CH_2$—O—, —$CH_2$—S—, —CF=CH—, —CH=CF—, —CHF—$CH_2$— and —$CH_2$—CHF—.

7. The compound according to claim 1 or its pharmaceutically-acceptable salt, wherein $Ar_1$ is selected from a group consisting of a 1,4-phenylenediyl group, a thiazole-2,4-diyl group, a 2-oxo-1,2-dihydropyridine-1,4-diyl group, a 2-methoxy-1,4-phenylenediyl group, a 2-methyl-1,4-phenylenediyl group, a piperidine-1,4-diyl group, an azetidine-1,3-diyl group, a 2-fluoro-1,4-phenylenediyl group, a 2-chloro-1,4-phenylenediyl group, a pyridine-2,5-diyl group, a 6-chloro-pyridine-2,5-diyl group, a pyrimidine-2,5-diyl group, a pyrazine-2,5-diyl group, a pyridazine-3,6-diyl group, a 1H-imidazole-1,4-diyl group, a [1,3,4]thiadiazole-2,5-diyl group, a [1,3,4]oxadiazole-2,5-diyl group, a 1H-indole-2,5-diyl group, a 1H-benzimidazole-2,5-diyl group, a benzoxazole-2,5-diyl group, a benzothiazole-2,6-diyl group, a benzothiazole-2,5-diyl group, a pyrrolidine-1,3-diyl group, a 1H-[1,2,4]triazole-1,3-diyl group, a 4-methyl-2H-[1,2,3]triazole-2,5-diyl group, a [1,2,4]oxadiazole-3,5-diyl group, a 2H-tetrazole-2,5-diyl group, a 5-methyl-1H-pyrazole-1,4-diyl group, and a 1,4-cyclohexylene group.

8. The compound according to claim 1 or its pharmaceutically-acceptable salt, wherein $Ar_2$ is selected from a phenyl group, a 6-chloropyridin-3-yl group, a 4-chloropyridin-2-yl group, a 5-fluoropyridin-2-yl group, a 3-fluoropyridin-2-yl group, a 6-fluoropyridin-2-yl group, a 5-methyl-1,3,4-thiadiazol-2-yl group, a 5-fluoro-pyrimidin-2-yl group, a 6-methylpyridin-2-yl group, a 1,3-thiazol-2-yl group, a 3-difluoromethoxypyridin-6-yl group, a 4-fluorophenyl group, a 4-chlorophenyl group, a 4-trifluoromethylphenyl group, a 4-methoxyphenyl group, a 4-(methylthio)pyridin-2-yl group, a 4-methylsulfonylphenyl group, a pyridin-2-yl group, a pyridin-3-yl group, a 2-fluoropyridin-5-yl group, a 3-fluoropyridin-6-yl group, a 3-chloropyridin-6-yl group, a 2-methoxypyridin-5-yl group, a 3-methoxypyridin-6-yl group, a 5-trifluoromethylpyridin-2-yl group, a 3-trifluoromethylpyridin-2-yl group, a 4-trifluoromethylpyridin-2-yl group, a 2-trifluoromethylpyridin-5-yl group, and a 6-chloropyridazin-3-yl group.

9. The compound according to claim 1, or its pharmaceutically-acceptable salt, wherein $R^1$ is selected from: the group consisting of a methyl group, an ethyl group, an isopropyl group, a t-butyl group, a hydroxymethyl group, a 1-methyl-1-hydroxyethyl group, a cyclopropyl group, a tetrahydrofuran-3-yl group, a 3-oxocyclobutyl group, a 3-methoxycyclobutyl group, a methoxymethyl group, a pyrrolidin-1-ylpropyl group, a 3-morpholin-4-ylpropyl group, a 3-hydroxypropyl group, a 3-hydroxy-3-methylbutyl group, a 3-(3-fluoropyrrolidin-1-yl)propyl group, a 3-(3,3-difluoropyrrolidin-1-yl)propyl group, and a 3-hydroxy-3-methylcyclobutyl group;

$R^2$ is selected from: the group consisting of a hydrogen atom, a methyl group, an ethyl group, a hydroxymethyl group, a 1-hydroxyethyl group, a cyclopropyl group, a methoxymethyl group, a cyanomethyl group, and a pyrrolidin-1-ylmethyl group;

$R^3$ is: a hydrogen atom, or a methyl group;

$R^4$ is: a hydrogen atom, or a methyl group;

W is selected from: the group consisting of —CH=CH—, —O—, —O—$CH_2$—, —$CH_2$—O—, —$CH_2$—S—, —CF=CH—, —CH=CF—, —CHF—$CH_2$— and —$CH_2$—CHF—;

Ar₁ is selected from a group consisting of a 1,4-phenylenediyl group, a thiazole-2,4-diyl group, a 2-oxo-1,2-dihydropyridine-1,4-diyl group, a 2-methoxy-1,4-phenylenediyl group, a 2-methyl-1,4-phenylenediyl group, a piperidine-1,4-diyl group, an azetidine-1,3-diyl group, a 2-fluoro-1,4-phenylenediyl group, a 2-chloro-1,4-phenylenediyl group, a pyridine-2,5-diyl group, a 6-chloropyridine-2,5-diyl group, a pyrimidine-2,5-diyl group, a pyrazine-2,5-diyl group, a pyridazine-3,6-diyl group, a 1H-imidazole-1,4-diyl group, a [1,3,4]thiadiazole-2,5-diyl group, a [1,3,4]oxadiazole-2,5-diyl group, a 1H-indole-2,5-diyl group, a 1H-benzimidazole-2,5-diyl group, a benzoxazole-2,5-diyl group, a benzothiazole-2,6-diyl group, a benzothiazole-2,5-diyl group, a pyrrolidine-1,3-diyl group, a 1H-[1,2,4]triazole-1,3-diyl group, a 4-methyl-2H-[1,2,3]triazole-2,5-diyl group, a [1,2,4]oxadiazole-3,5-diyl group, a 2H-tetrazole-2,5-diyl group, a 5-methyl-1H-pyrazole-1,4-diyl group, a 1,4-cyclohexylene group, and a 1,3-cyclopentylene group;

Ar₂ is selected from a phenyl group, a 6-chloropyridin-3-yl group, a 4-chloropyridin-2-yl group, a 5-fluoropyridin-2-yl group, a 3-fluoropyridin-2-yl group, a 6-fluoropyridin-2-yl group, a 5-methyl-1,3,4-thiadiazol-2-yl group, a 5-fluoro-pyrimidin-2-yl group, a 6-methylpyridin-2-yl group, a 1,3-thiazol-2-yl group, a 3-difluoromethoxypyridin-6-yl group, a 4-fluorophenyl group, a 4-chlorophenyl group, a 4-trifluoromethylphenyl group, a 4-methoxyphenyl group, a 4-(methylthio)pyridin-2-yl group, a 4-methylsulfonylphenyl group, a pyridin-2-yl group, a pyridin-3-yl group, a 2-fluoropyridin-5-yl group, a 3-fluoropyridin-6-yl group, a 3-chloropyridin-6-yl group, a 2-methoxypyridin-5-yl group, a 3-methoxypyridin-6-yl group, a 5-trifluoromethylpyridin-2-yl group, a 3-trifluoromethylpyridin-2-yl group, a 4-trifluoromethylpyridin-2-yl group, a 2-trifluoromethylpyridin-5-yl group, and a 6-chloropyridazin-3-yl group.

10. The compound or its pharmaceutically-acceptable salt as claimed in claim 1, wherein the compound of formula [I] is selected from the group consisting of:

N-[2-(3-trans-methoxycyclobutyl)-3-methylimidazo[1,2-a]pyridin-6-yl]-4-(pyridin-2-ylmethoxy)benzamide;
4-(5-fluoropyridin-2-ylmethoxy)-N-(2-isopropyl-3-methylimidazo[1,2-a]pyridin-6-yl)benzamide;
N-(2-ethyl-3-methylimidazo[1,2-a]pyridin-6-yl)-3-fluoro-4-(pyridin-2-ylmethoxy)benzamide;
N-(2-ethyl-3-methylimidazo[1,2-a]pyridin-6-yl)-3-fluoro-4-(pyridin-2-yloxymethyl)benzamide;
3-fluoro-N-[3-methyl-2-(tetrahydrofuran-3-yl)imidazo[1,2-a]pyridin-6-yl]-4-((E)-2-pyridin-2-ylvinyl)benzamide;
N-(2-ethyl-3-methylimidazo[1,2-a]pyridin-6-yl)-4-((Z)-2-fluoro-2-pyridin-2-ylvinyl)benzamide;
N-(2-ethyl-3-methylimidazo[1,2-a]pyridin-6-yl)-4-(2-fluoro-2-pyridin-2-ylethyl)benzamide;
N-[3-methyl-2-(tetrahydrofuran-3-yl)imidazo[1,2-a]pyridin-6-yl]-4-(pyridin-2-ylmethylsulfanyl)benzamide;
4-(4-chloropyridin-2-yloxy)-N-(2-ethyl-3-methylimidazo[1,2-a]pyridin-6-yl)benzamide;
N-(2-ethyl-3-methylimidazo[1,2-a]pyridin-6-yl)-4-(4-methylsulfanylpyridin-2-yloxy)benzamide;
N-[3-methyl-2-(3-oxocyclobutyl)imidazo[1,2-a]pyridin-6-yl]-4-((E)-2-pyridin-2-ylvinyl)benzamide;
4-(benzyloxy)-N-[3-methyl-2-(3-pyrrolidin-1-ylpropyl)imidazo[1,2-a]pyridin-6-yl)]benzamide;
N-[3-methyl-2-(3-pyrrolidin-1-ylpropyl)imidazo[1,2-a]pyridin-6-yl]-4-(pyridin-2-ylmethoxy)benzamide;
4-[(E)-2-(6-fluoropyridin-2-yl)vinyl]-N-[3-methyl-2-(tetrahydrofuran-3-yl)imidazo[1,2-a]pyridin-6-yl]benzamide;
4-[(E)-2-(5-fluoropyridin-2-yl)vinyl]-N-[2-(1-hydroxy-1-methylethyl)-3-methylimidazo[1,2-a]pyridin-6-yl]benzamide;
4-[(E)-2-(5-fluoropyridin-2-yl)vinyl]-N-[3-methyl-2-(tetrahydrofuran-3-yl)imidazo[1,2-a]pyridin-6-yl]benzamide;
N-(2-ethyl-3-methylimidazo[1,2-a]pyridin-6-yl)-4-[(Z)-1-fluoro-2-pyridin-2-ylvinyl]benzamide;
4-[(Z)-1-fluoro-2-pyridin-2-ylvinyl]-N-[3-methyl-2-(tetrahydrofuran-3-yl)imidazo[1,2-a]pyridin-6-yl]benzamide;
N-[3-methyl-2-(3-pyrrolidin-1-ylpropyl)imidazo[1,2-a]pyridin-6-yl]-4-[(E)-2-pyridin-2-ylvinyl]benzamide; and
N-[2-(3-hydroxy-3-methylcyclobutyl)-3-methylimidazo[1,2-a]pyridin-6-yl]-4-((E)-2-pyridin-2-ylvinyl)benzamide.

11. The compound or its pharmaceutically-acceptable salt as claimed in claim 1, wherein the compound of formula [I] is N-[2-(3-trans-methoxycyclobutyl)-3-methylimidazo[1,2-a]pyridin-6-yl]-4-(pyridin-2-ylmethoxy)benzamide.

12. The compound or its pharmaceutically-acceptable salt as claimed in claim 1, wherein the compound of formula [I] is N-[3-methyl-2-(3-pyrrolidin-1-ylpropyl)imidazo[1,2-a]pyridin-6-yl]-4-(pyridin-2-ylmethoxy)benzamide.

13. The compound or its pharmaceutically-acceptable salt as claimed in claim 1, wherein the compound of formula [I] is N-[3-methyl-2-(3-oxocyclobutyl)imidazo[1,2-a]pyridin-6-yl]-4-((E)-2-pyridin-2-ylvinyl)benzamide.

14. The compound or its pharmaceutically-acceptable salt as claimed in claim 1, wherein the compound of formula [I] is 4-[(E)-2-(5-fluoropyridin-2-yl)vinyl]-N-[3-methyl-2-(tetrahydrofuran-3-yl)imidazo[1,2-a]pyridin-6-yl]benzamide.

15. The compound or its pharmaceutically-acceptable salt as claimed in claim 1, wherein the compound of formula [I] is 4-[(Z)-1-fluoro-2-pyridin-2-ylvinyl]-N-[3-methyl-2-(tetrahydrofuran-3-yl)imidazo[1,2-a]pyridin-6-yl]benzamide.

16. A pharmaceutical composition comprising a compound according to claim 1, and a pharmaceutically-acceptable carrier.

17. A pharmaceutical composition comprising a compound according to claim 10 and a pharmaceutically acceptable carrier.

18. The compound or its pharmaceutically-acceptable salt as claimed in claim 1, wherein the compound of formula [I] is N-(2-ethyl-3-methylimidazo[1,2-a]pyridin-6-yl)-3-fluoro-4-(pyridin-2-ylmethoxy)benzamide.

* * * * *